United States Patent
Gambhir et al.

(10) Patent No.: US 10,712,277 B2
(45) Date of Patent: Jul. 14, 2020

(54) RAMAN IMAGING DEVICES AND METHODS OF MOLECULAR IMAGING

(75) Inventors: Sanjiv Sam Gambhir, Portola Valley, CA (US); Cristina Zavaleta, Palo Alto, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 506 days.

(21) Appl. No.: 12/932,912

(22) Filed: Mar. 9, 2011

(65) Prior Publication Data

US 2011/0230760 A1    Sep. 22, 2011

Related U.S. Application Data

(63) Continuation-in-part of application No. 12/598,780, filed as application No. PCT/US2008/062649 on May 5, 2008, now Pat. No. 8,795,628.

(Continued)

(51) Int. Cl.
     *G01N 21/65*      (2006.01)
     *A61B 5/00*      (2006.01)
(Continued)

(52) U.S. Cl.
CPC ......... *G01N 21/658* (2013.01); *A61B 5/0071* (2013.01); *A61B 5/0075* (2013.01); *A61K 49/00* (2013.01); *A61K 49/0002* (2013.01); *A61K 49/0065* (2013.01); *A61K 49/0093* (2013.01); *A61K 51/1244* (2013.01); *B82Y 5/00* (2013.01); *B82Y 15/00* (2013.01); *B82Y 30/00* (2013.01); *A61B 5/0073* (2013.01); *A61B 5/0084* (2013.01); *A61B 5/0088* (2013.01); *A61B 5/416* (2013.01)

(58) Field of Classification Search
CPC .. A61B 1/07; A61B 2017/00057; A61B 16/00
USPC ........................................................ 600/431
See application file for complete search history.

(56) References Cited

U.S. PATENT DOCUMENTS 5,421,337 A * 6/1995 Richards-Kortum ........................ A61B 5/0071
                                                600/477
7,720,526 B1 * 5/2010 Modell ................ A61B 5/0066
                                                356/407

(Continued)

FOREIGN PATENT DOCUMENTS

WO   WO 2009/0206680    *   2/2009 ............. G01N 21/65
WO   WO 2009020680 A2 *   2/2009

OTHER PUBLICATIONS

Le Ru et al, "Proof of Single-Molecule Sensitivity in Surface Enhanced Raman Scattering (SERS) by Means of a Two-Analyte Technique", J. Phys. Chem. B 2006, 110, pp. 1944-1948 (Year: 2006).*

(Continued)

*Primary Examiner* — James M Kish
(74) *Attorney, Agent, or Firm* — Thomas|Horstemeyer, LLP

(57) ABSTRACT

In accordance with the purpose(s) of the present disclosure, as embodied and broadly described herein, embodiments of the present disclosure, in one aspect, relate to Raman imaging devices (e.g., Raman endoscope probes), methods of using Raman agents and Raman imaging devices to image or detect a signal, and the like.

15 Claims, 24 Drawing Sheets

Specification includes a Sequence Listing.

Related U.S. Application Data

(60) Provisional application No. 60/927,574, filed on May 4, 2007.

(51) Int. Cl.
    *A61K 49/00*     (2006.01)
    *A61K 51/12*     (2006.01)
    *B82Y 5/00*     (2011.01)
    *B82Y 15/00*     (2011.01)
    *B82Y 30/00*     (2011.01)

(56) References Cited

U.S. PATENT DOCUMENTS

| | | | | |
|---|---|---|---|---|
| 2003/0231304 | A1* | 12/2003 | Chan | C12Q 1/6825 356/301 |
| 2004/0073120 | A1* | 4/2004 | Motz | A61B 5/0071 600/478 |
| 2004/0127778 | A1* | 7/2004 | Lambert | A61B 5/14532 600/318 |
| 2004/0152992 | A1* | 8/2004 | Zeng | 600/476 |
| 2005/0251116 | A1* | 11/2005 | Steinke | A61B 5/0066 606/8 |
| 2007/0081156 | A1* | 4/2007 | Treado et al. | 356/301 |
| 2007/0225579 | A1* | 9/2007 | Lucassen et al. | 600/310 |
| 2008/0167524 | A1* | 7/2008 | Goldwasser | A61B 1/01 600/115 |
| 2008/0262359 | A1* | 10/2008 | Tearney | A61B 1/00096 600/476 |
| 2010/0136609 | A1* | 6/2010 | Clay | C12Q 1/04 435/34 |
| 2010/0284917 | A1* | 11/2010 | Kustner | B82Y 15/00 424/9.1 |
| 2011/0152692 | A1* | 6/2011 | Nie | A61B 5/0071 600/473 |
| 2011/0165077 | A1* | 7/2011 | Qian | A61K 49/0023 424/9.1 |

OTHER PUBLICATIONS

Hsiung, et al. "Detection of colonic dysplasia in vivo using a targeted fluorescent septapeptide and confocal microendoscopy." Nat. Med. 2008; 14(4): 454-458.

* cited by examiner

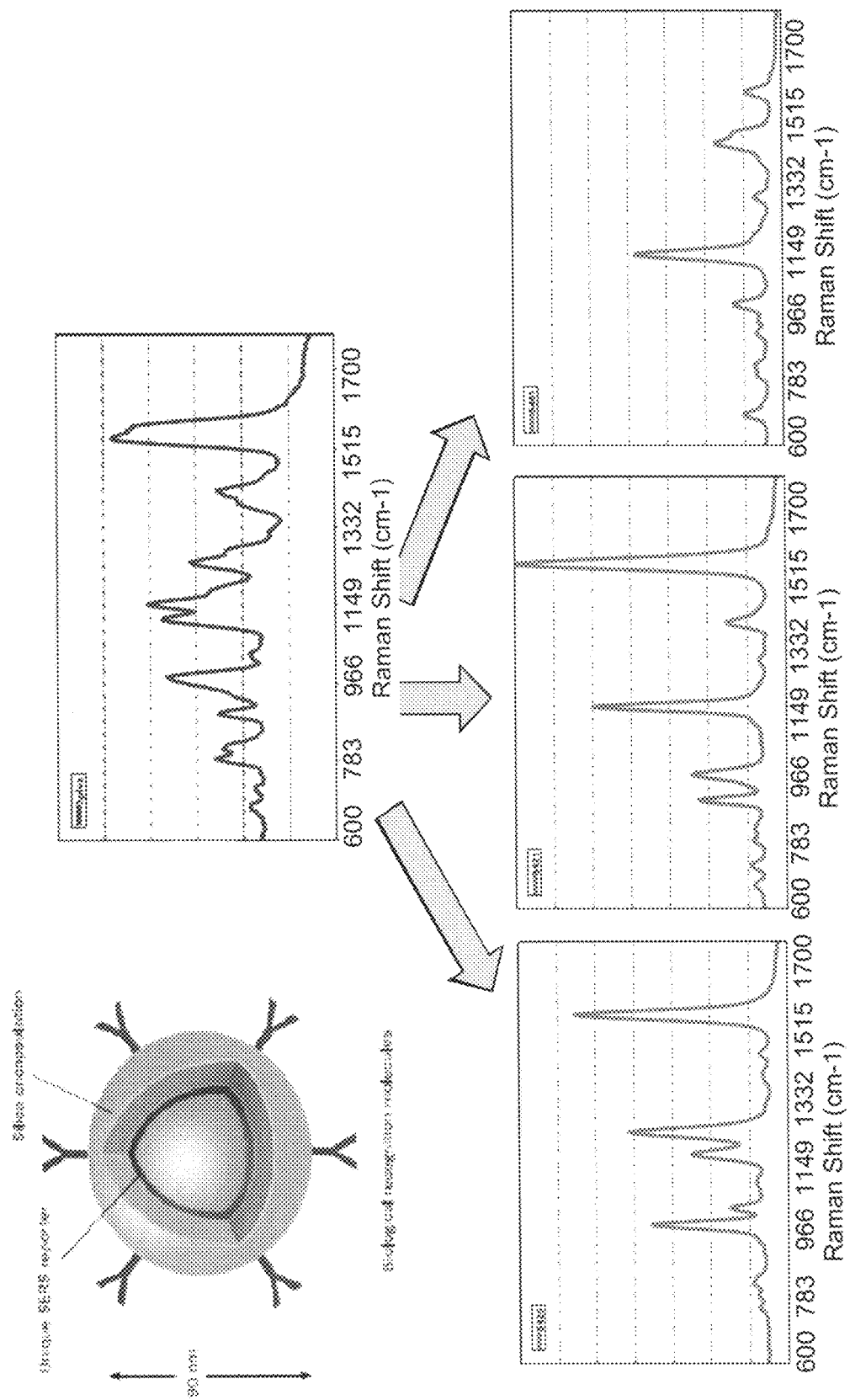
FIG. 1.1

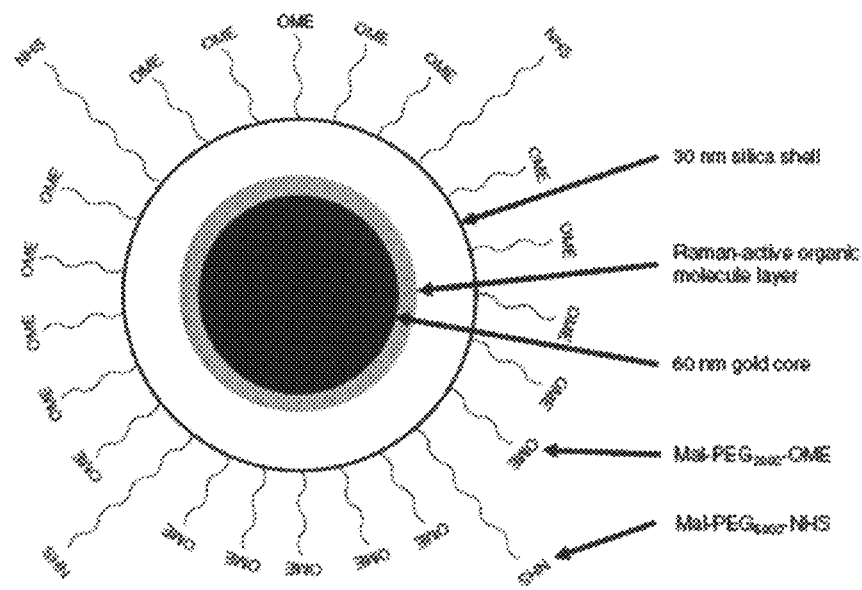
FIG. 2.1
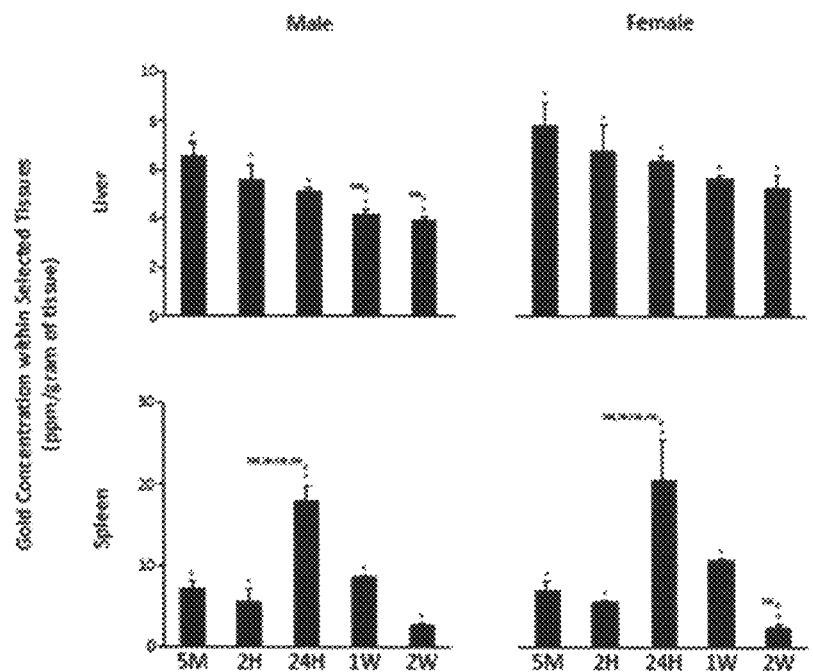
FIG. 2.2

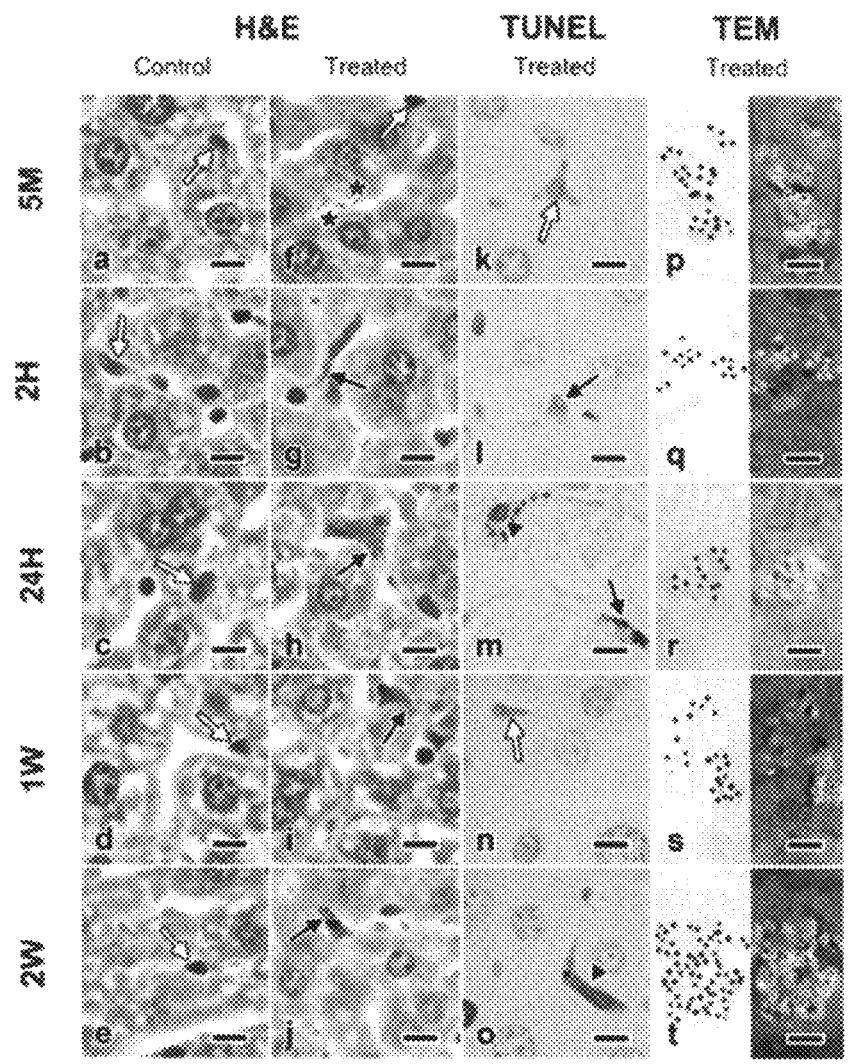
FIG. 2.3

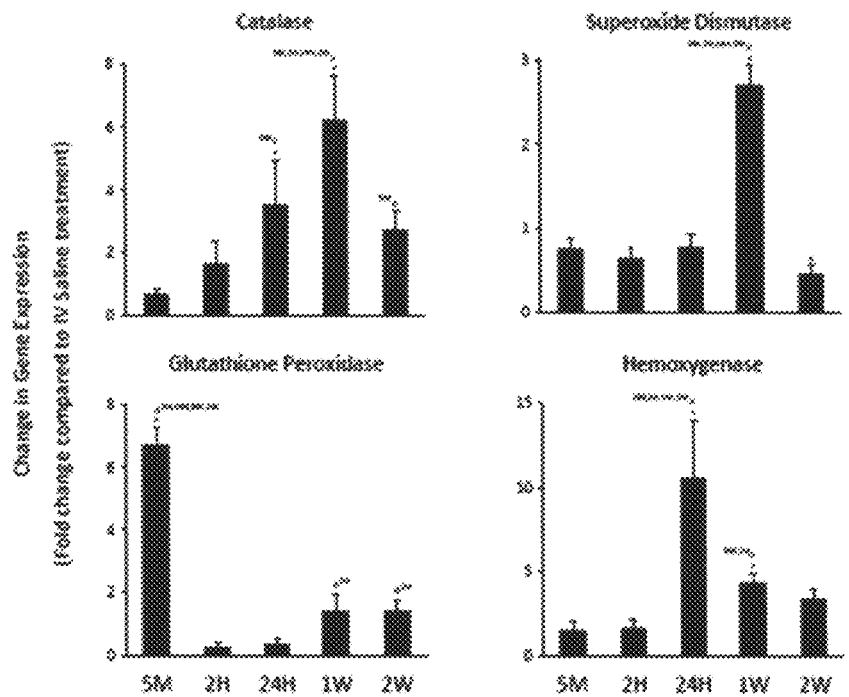
FIG. 2.4
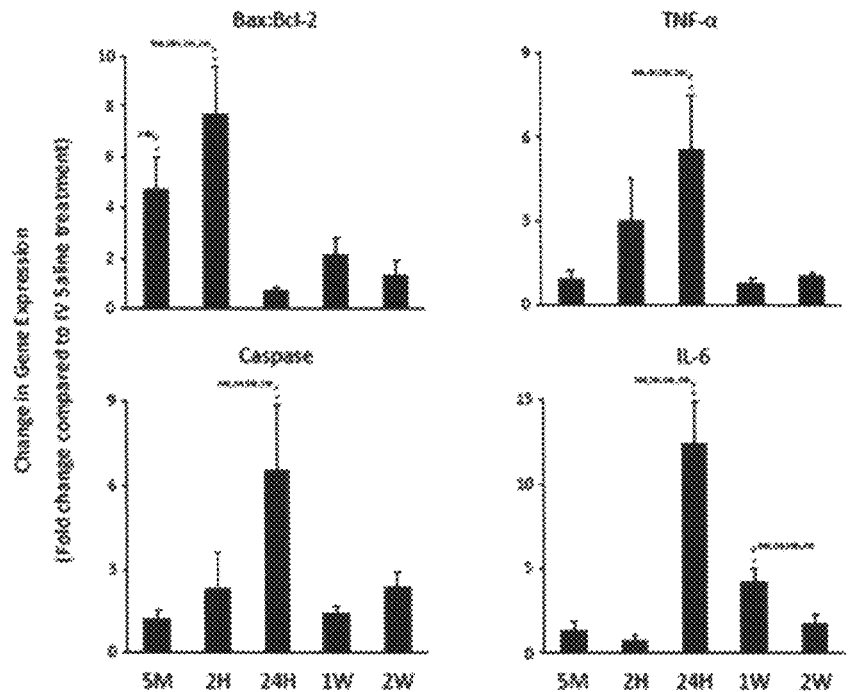
FIG. 2.5

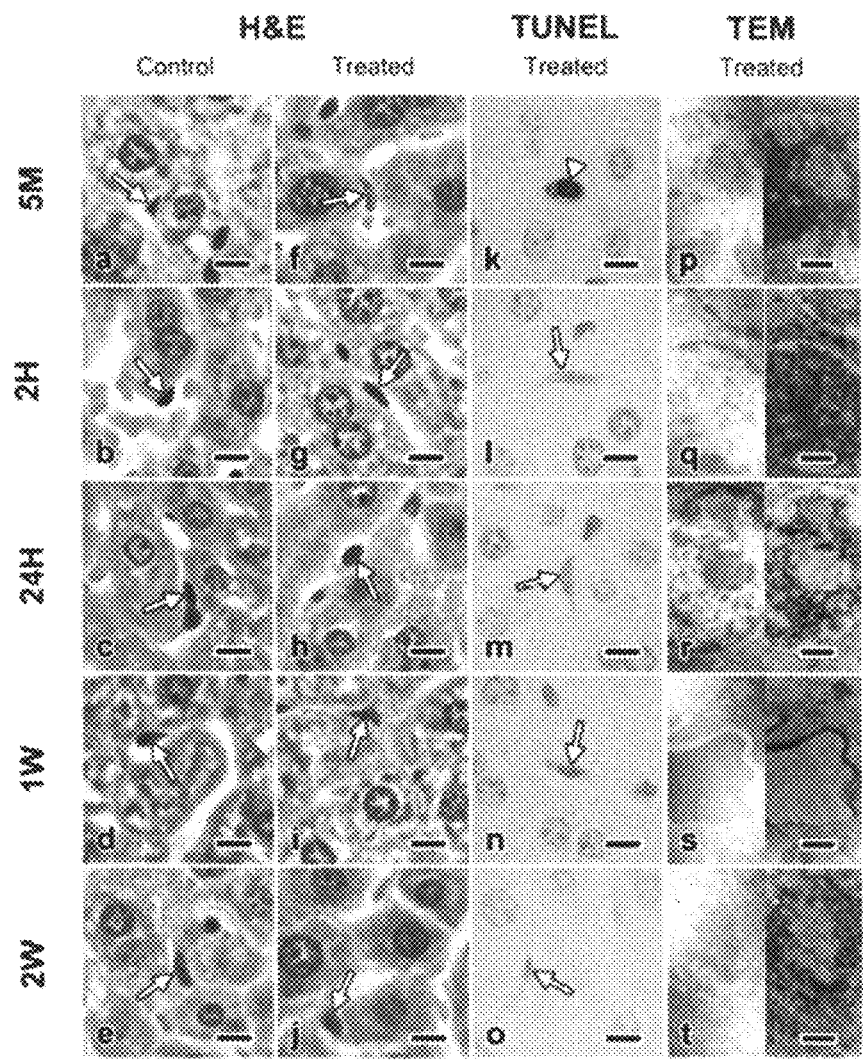
FIG. 2.6

FIG. 2.7

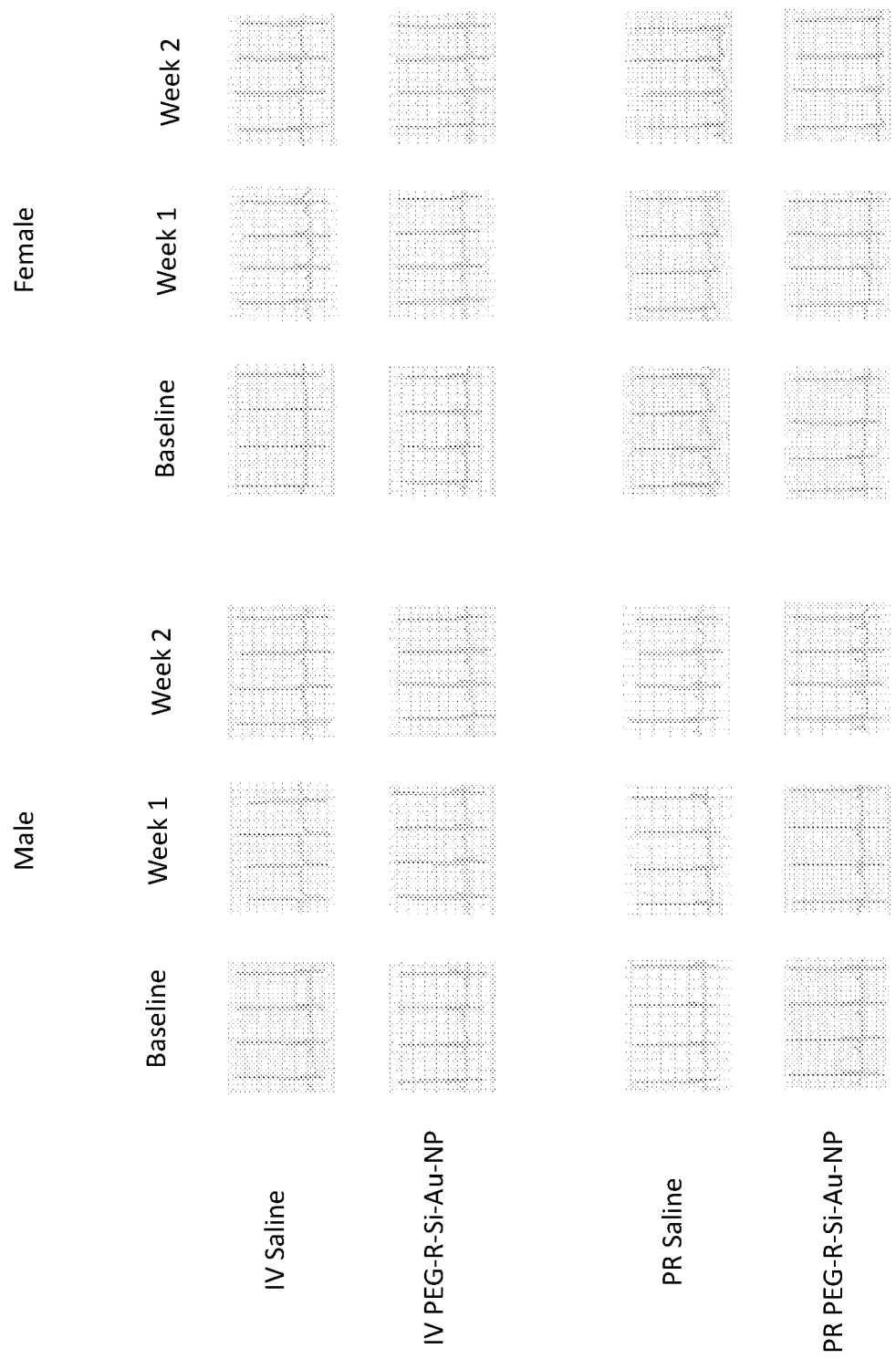
FIG. 2.8

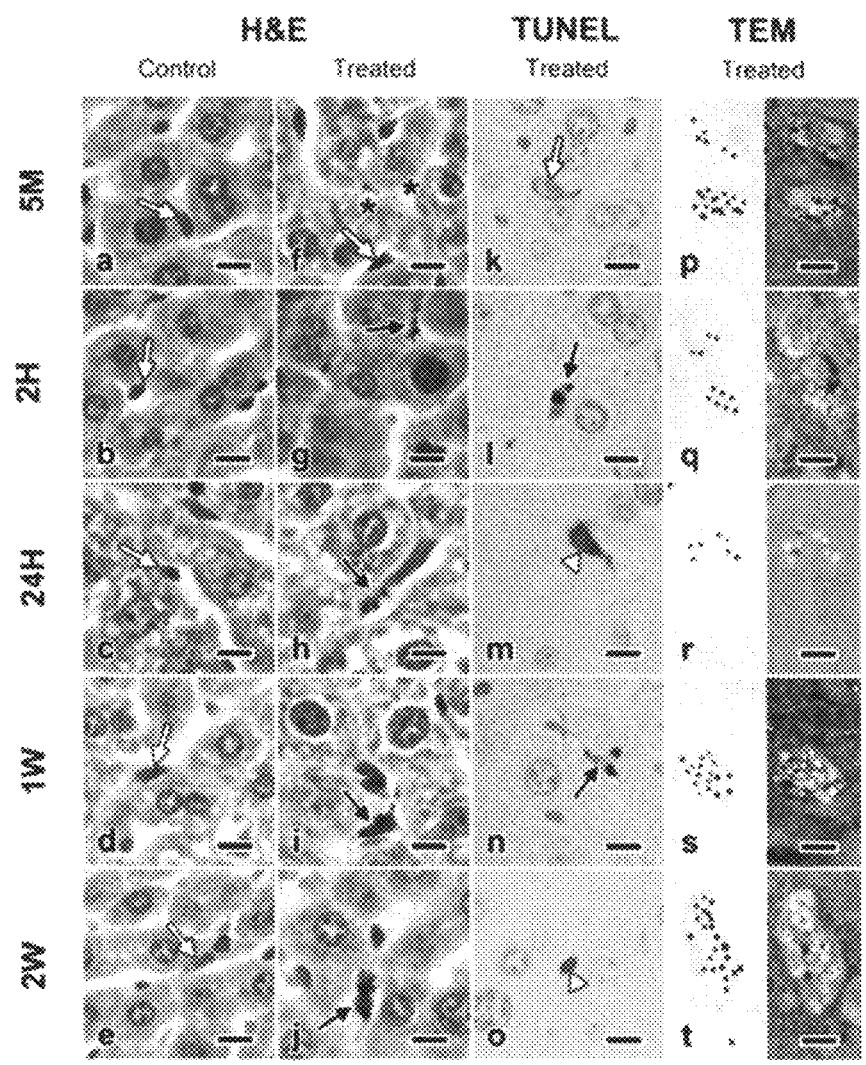
FIG. 2.9

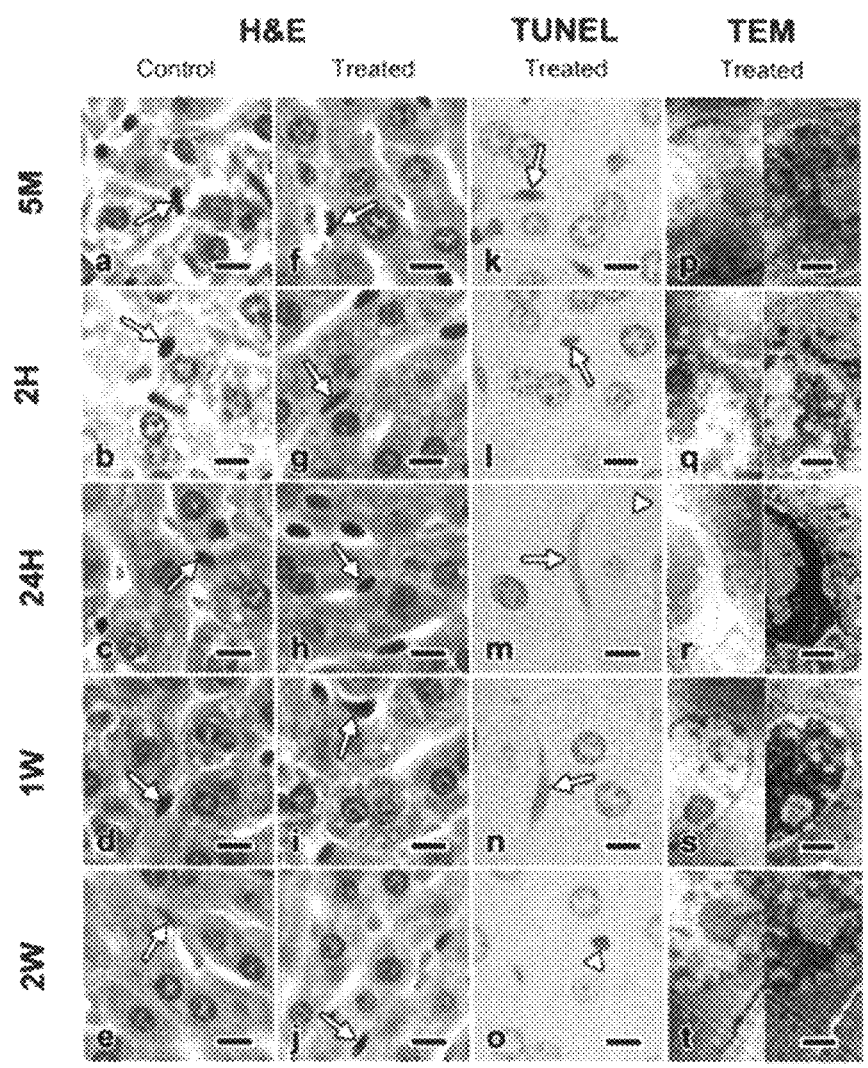
FIG. 2.10

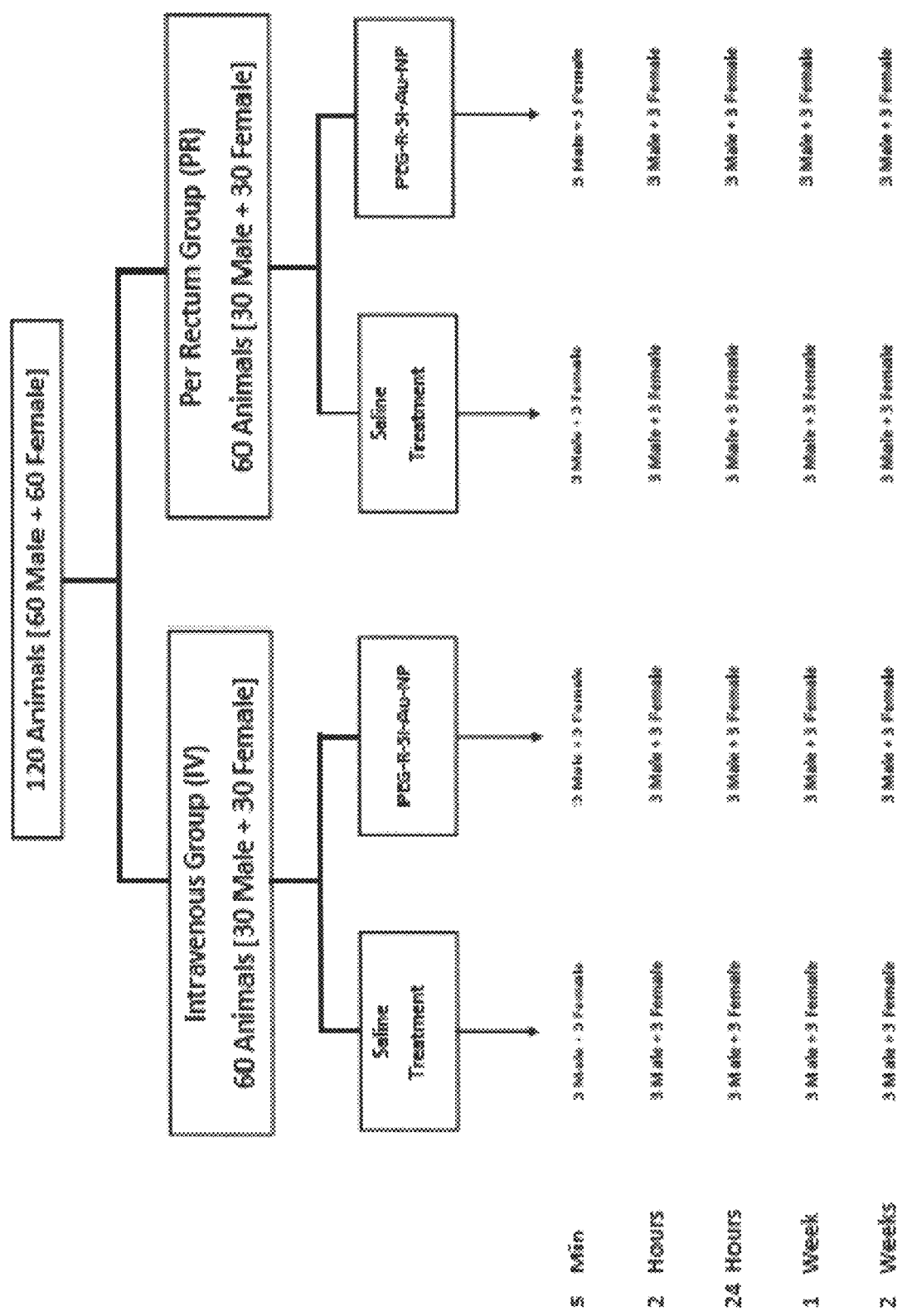
FIG. 2.11

| GENE NAME | PRIMER SEQUENCE |
|---|---|
| Hemoxygenase-1 | F: 5'-CTCGCATGCTTGCCATTG-3'<br>R: 5'-AGTGTAGGCTCCTTCATG-3' |
| Catalase | F: 5'-TATGACATTGCCAGTGA-3'<br>R: 5'-GTCTCAGGATAGCAAAG-3' |
| Interleukin-6 (IL-6) | F: 5'-CCAGTAGCCAGAAGA-3'<br>R: 5'-TTGTTTGTCAGCTC-3' |
| TNF-α | F: 5'-GGGCTTAGGGTCTGACC-3'<br>R: 5'-CAAACAAGTTCTGGCCTCC-3' |
| Superoxide Dismutase | F: 5'-CAAGCTGGAGGACATTC-3'<br>R: 5'-AGTGCAAGTCAACTGCAAC-3' |
| Glutathione Peroxidase | F: 5'-CTTCGAGAAGTGCGAGGT-3'<br>R: 5'-TCGATGCCATGGTCTGCAA-3' |
| Bcl-2 | F: 5'-GCTGAGCAGGAAGACTTTG-3'<br>R: 5'-ACCCCTGAAGAGTTCCTG-3' |
| Bax | F: 5'-AGGGTTGAGCAGGTCAGGAAG-3'<br>R: 5'-ATCTTTTGCAGGTGACCAC-3' |
| Caspase 3 | F: 5'-TGTTGTGTGCTTCTGAG-3'<br>R: 5'-ATTGTTGCCACCTTTCGC-3' |
| β-Actin | F: 5'-GCCGACATGGAAAAG-3'<br>R: 5'-AAGCAGCACTGTGTTGGCATAGAG-3' |

FIG. 2.15

IV PEG-R-Si-Au-NP Group

| | Male | Female |
|---|---|---|
| 5 Min | 0 | 0 |
| 2 Hours | 0 | 0 |
| 24 Hours | 0 | 1 |
| 1 Week | 0 | 0 |
| 2 Weeks | 2 | 0 |

IR PEG-R-Si-Au-NP Group

| | Male | Female |
|---|---|---|
| 5 Min | 0 | 0 |
| 2 Hours | 0 | 0 |
| 24 Hours | 0 | 0 |
| 1 Week | 0 | 0 |
| 2 Weeks | 0 | 0 |

FIG. 2.14

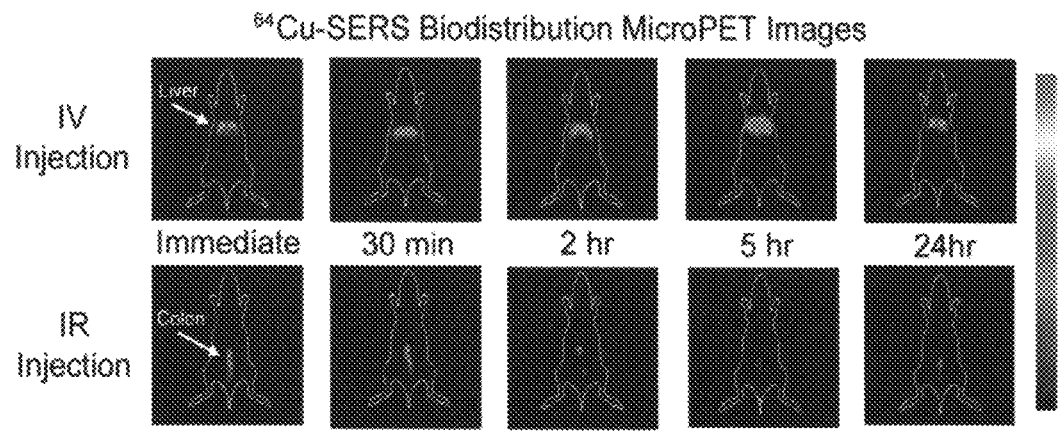
FIG. 3.1
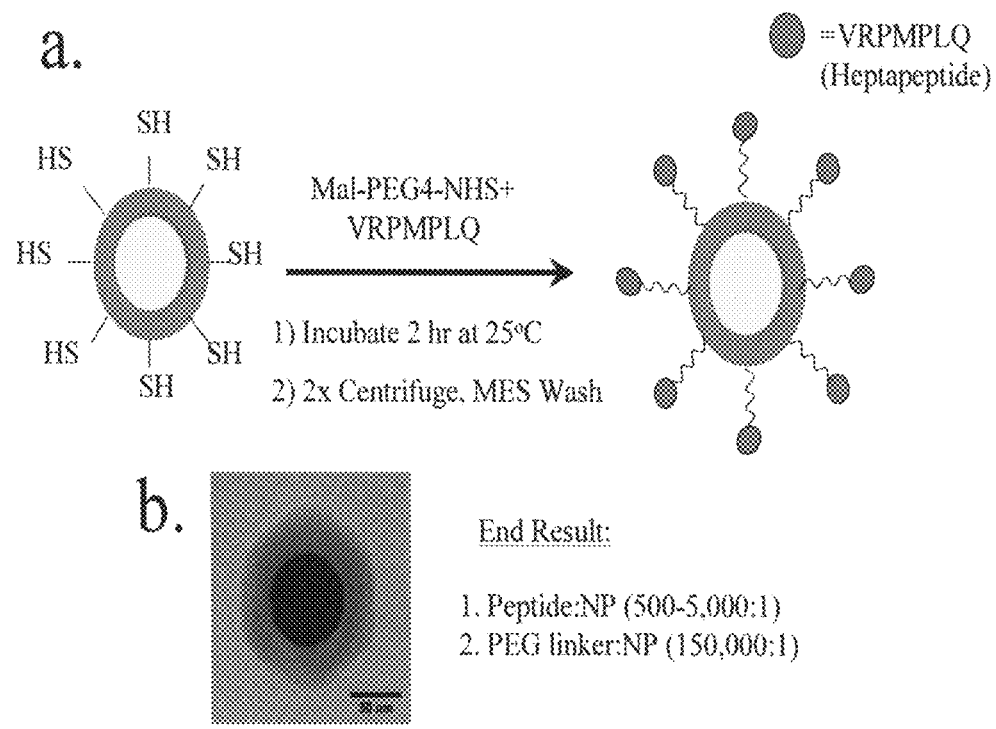
FIG. 3.2

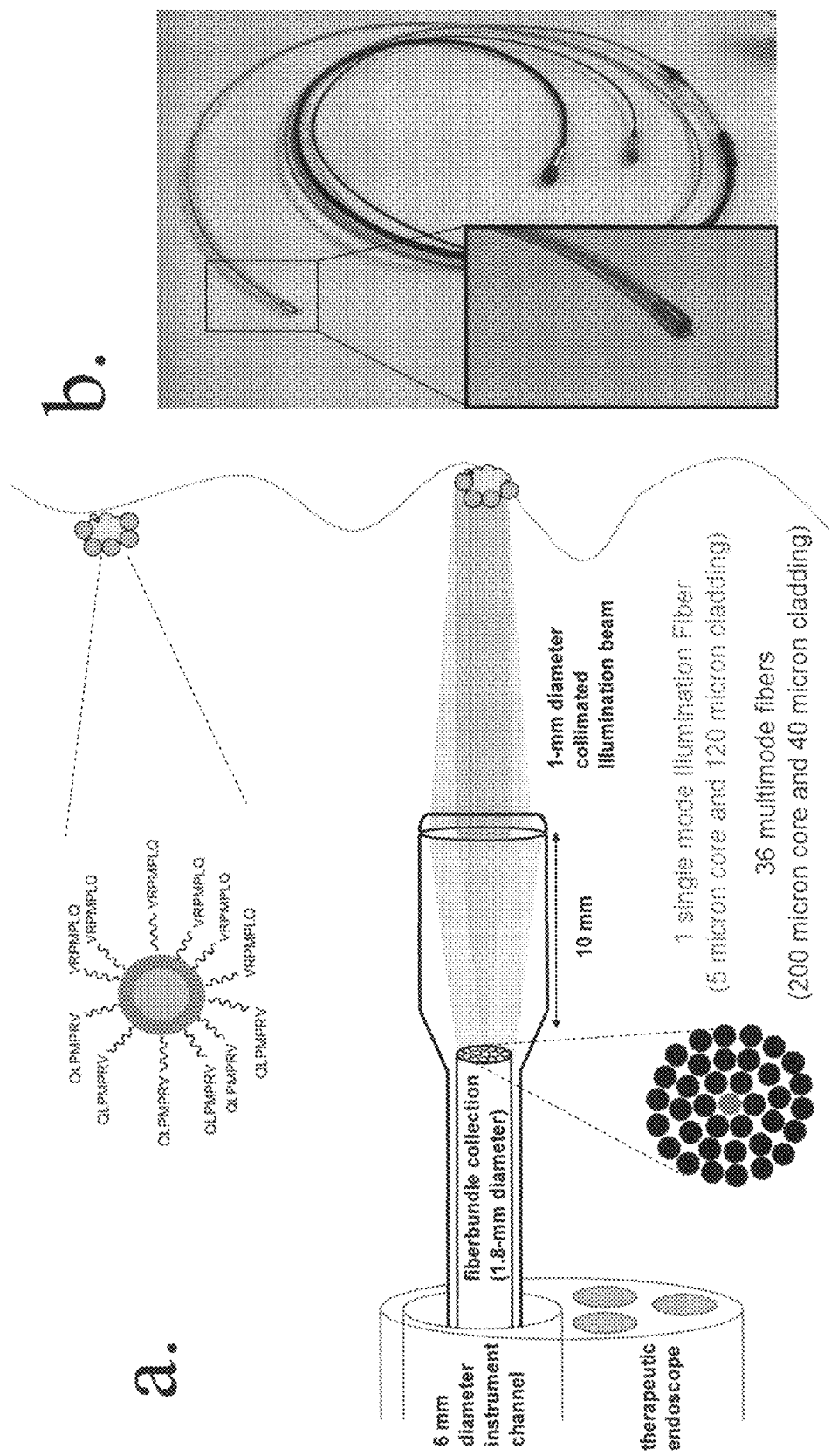
FIG. 3.3

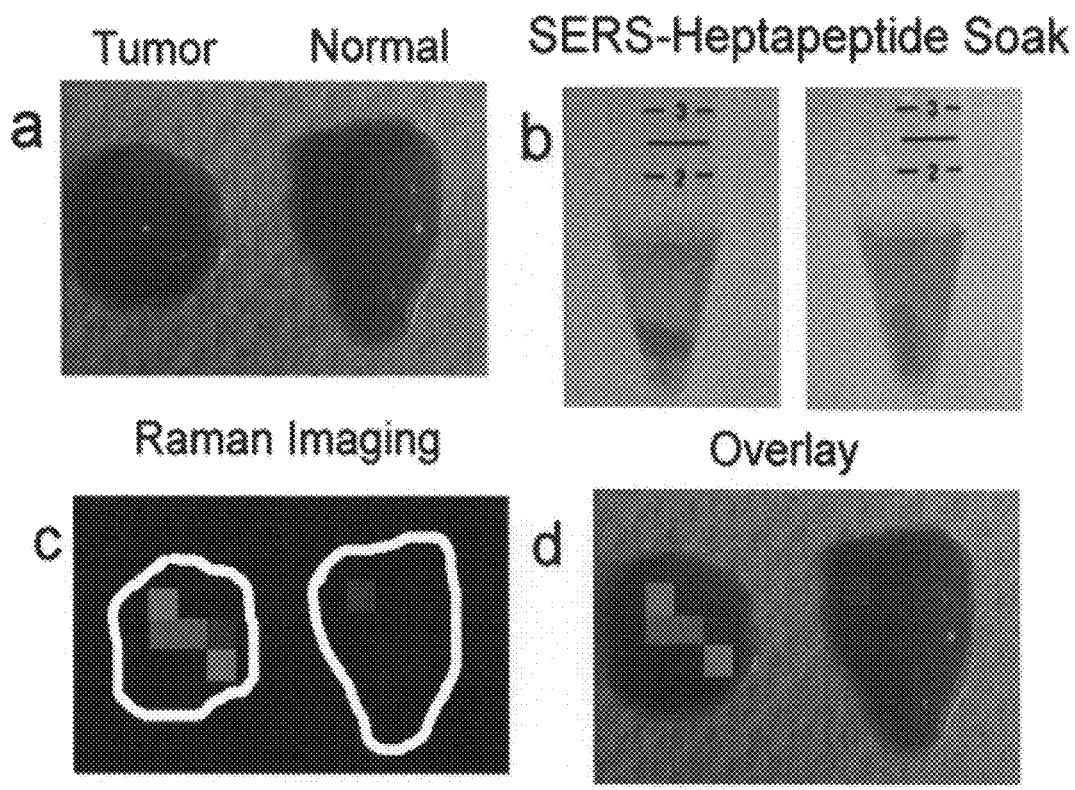
FIG. 3.4
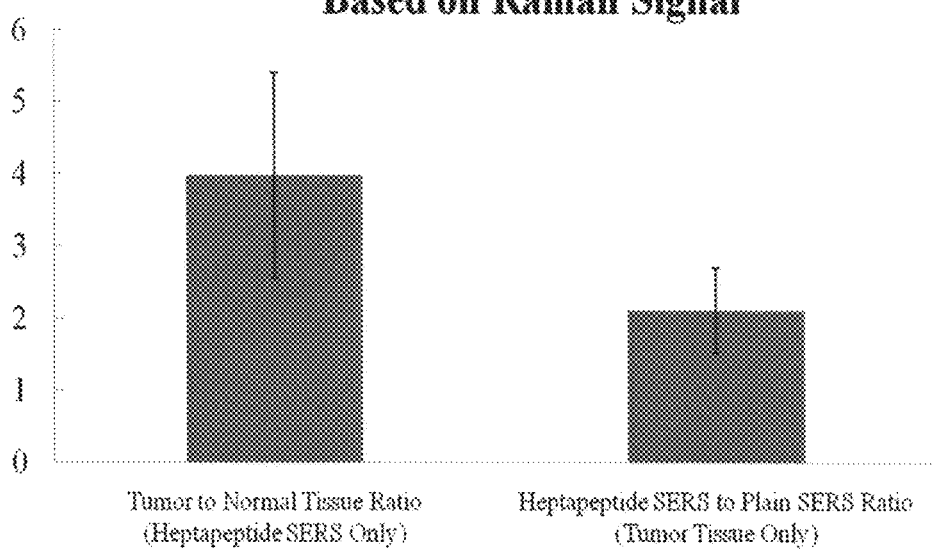
FIG. 3.5

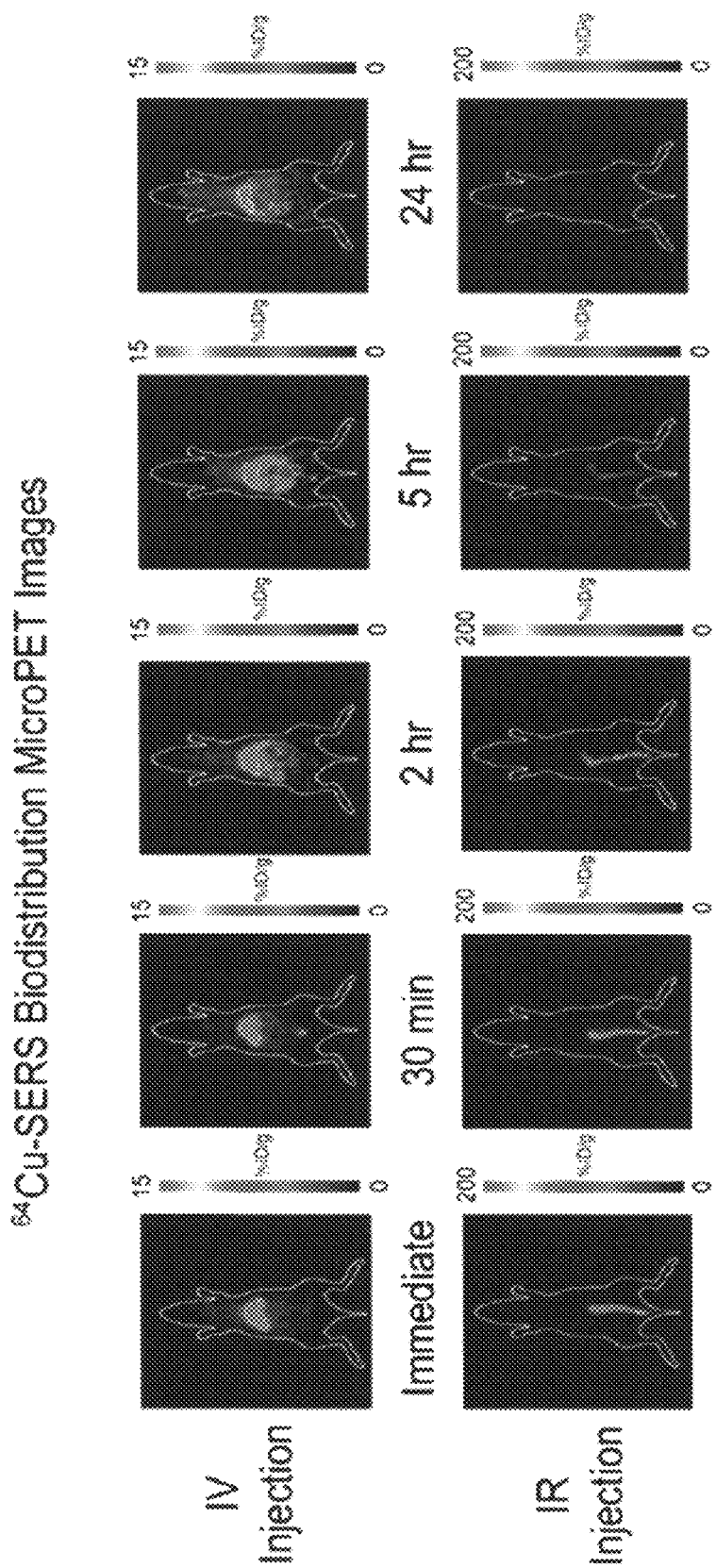
FIG. 4.1

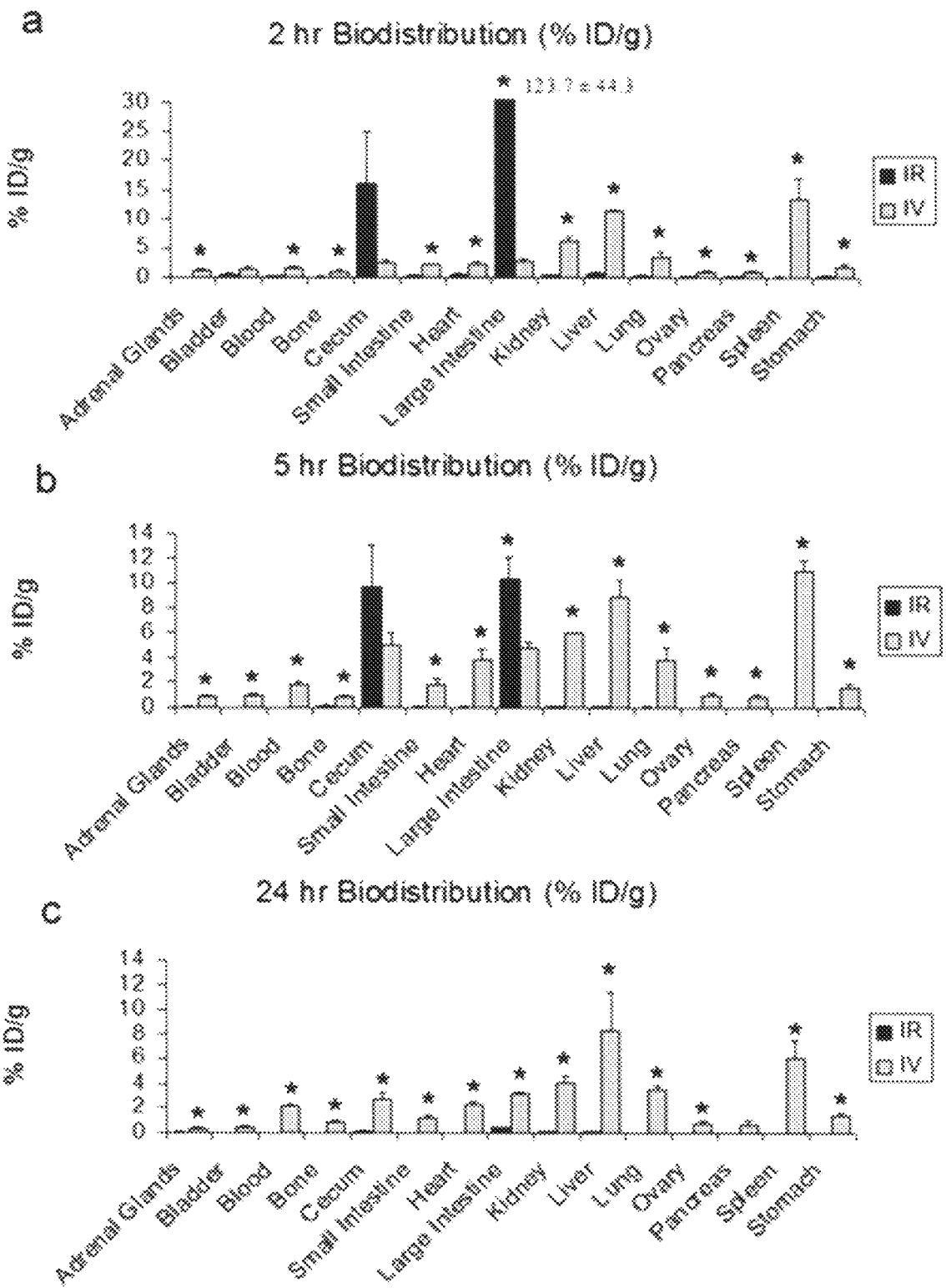
FIG. 4.2

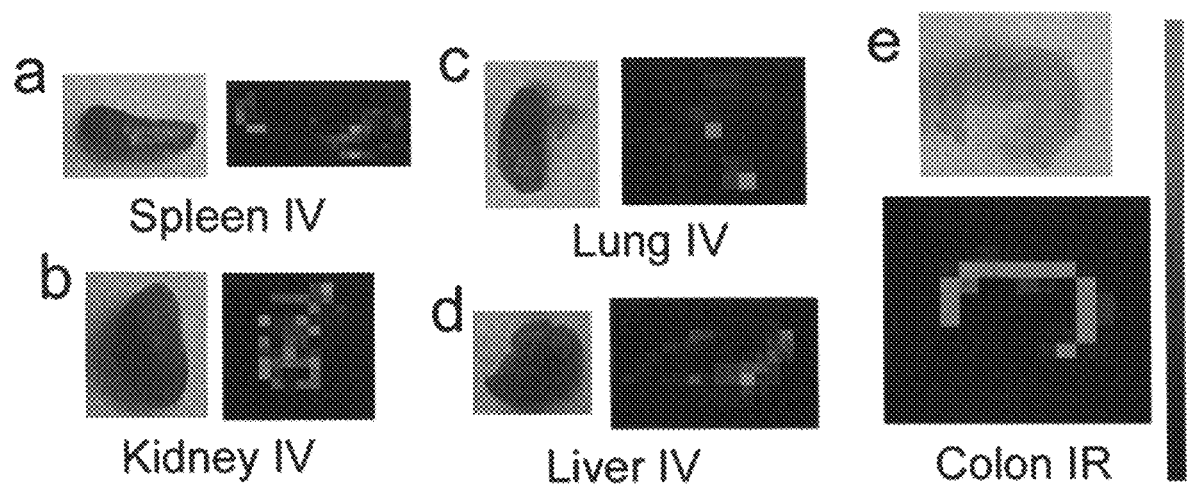
FIG. 4.3
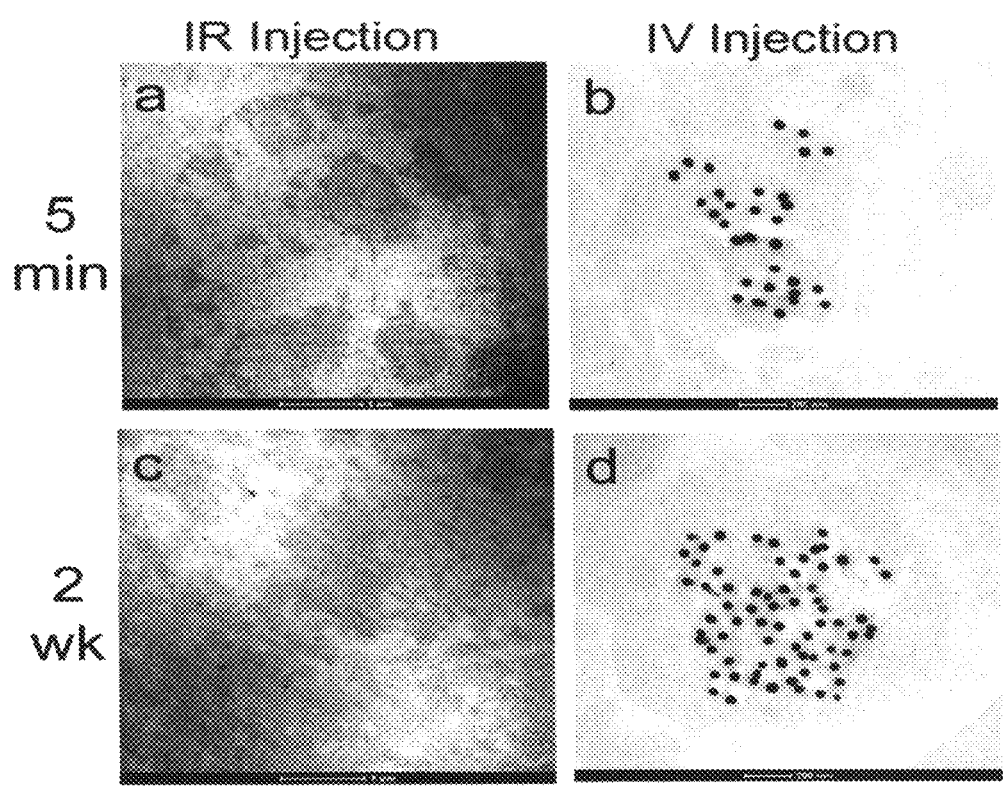
FIG. 4.4

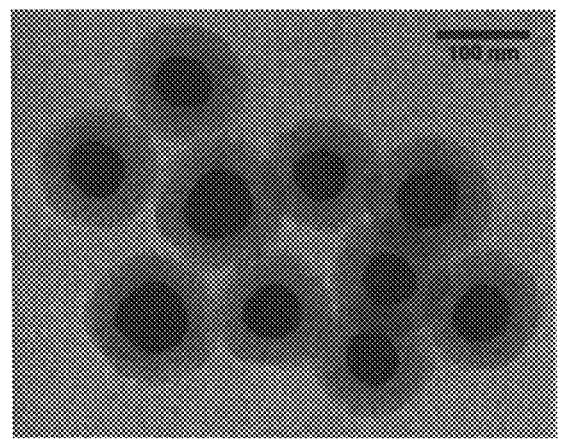
FIG. 4.5

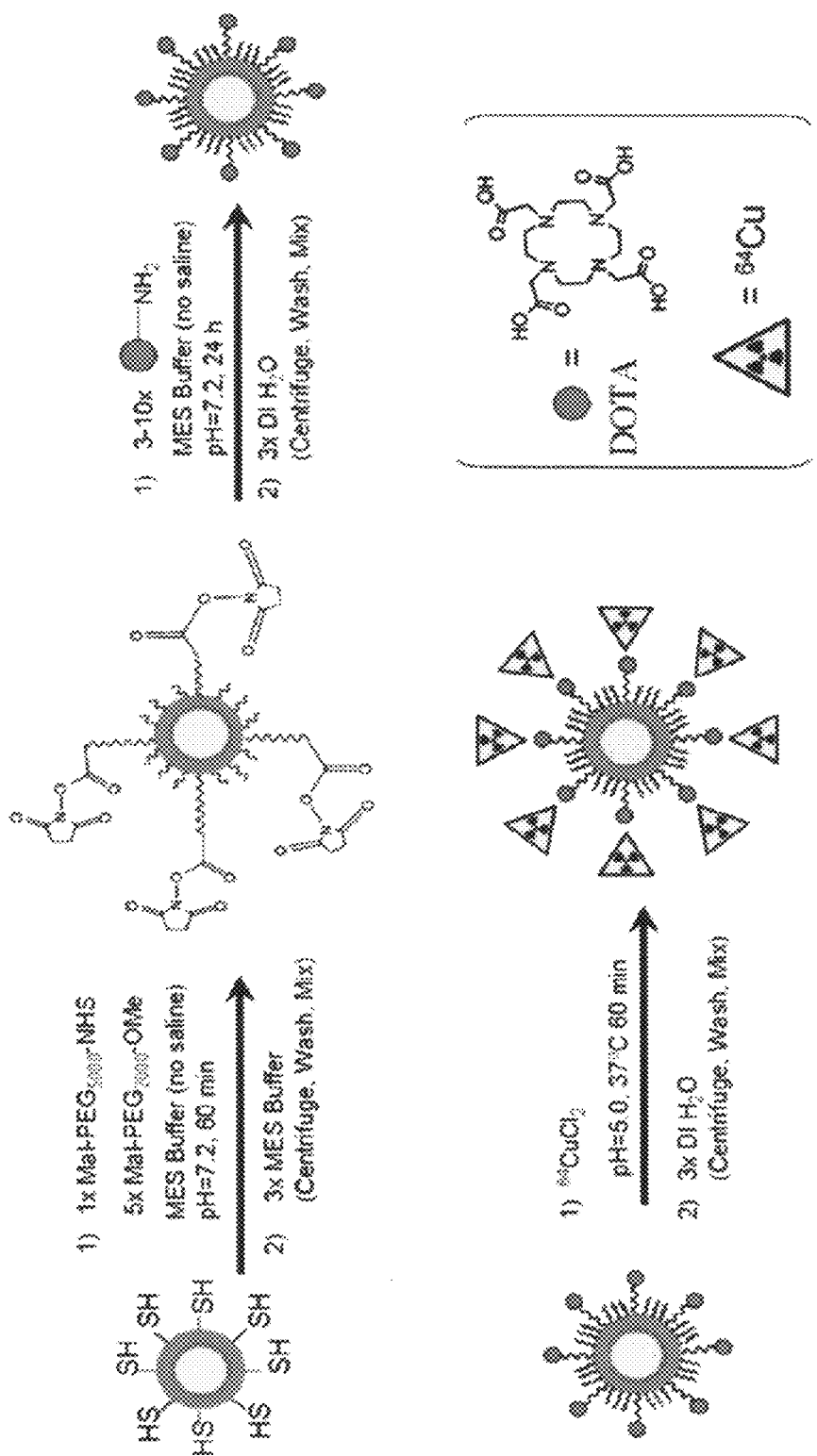
FIG. 4.6

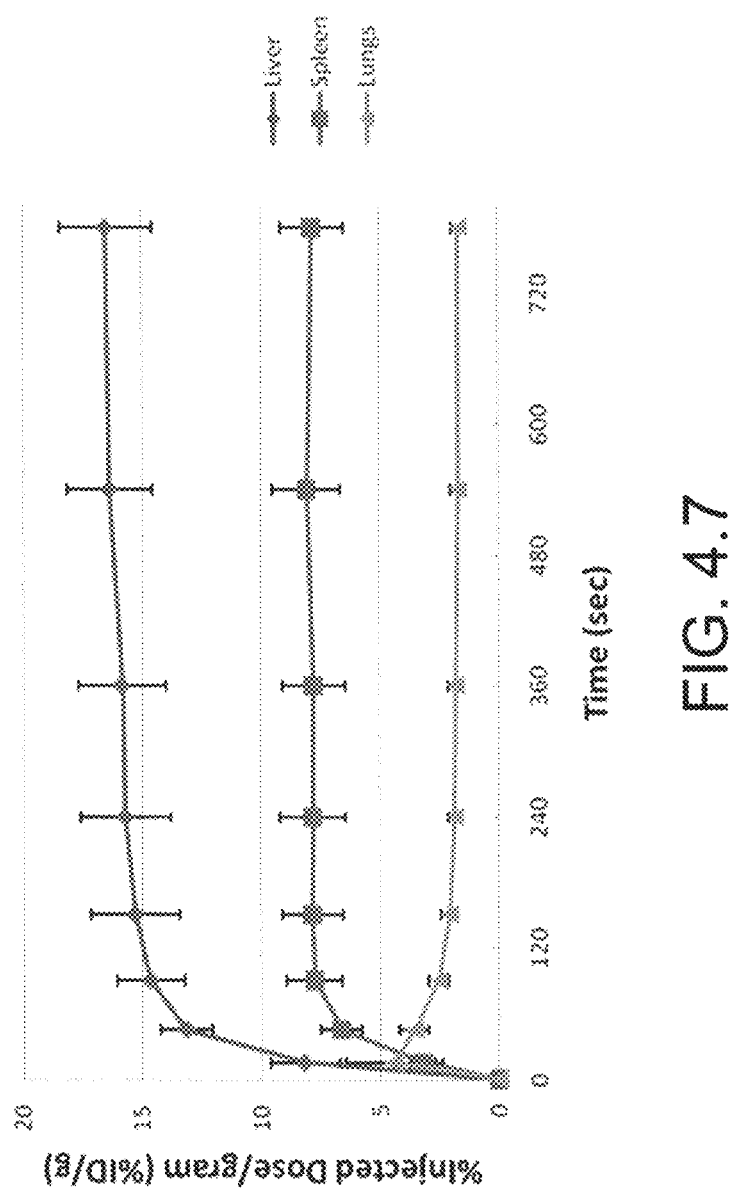
FIG. 4.7

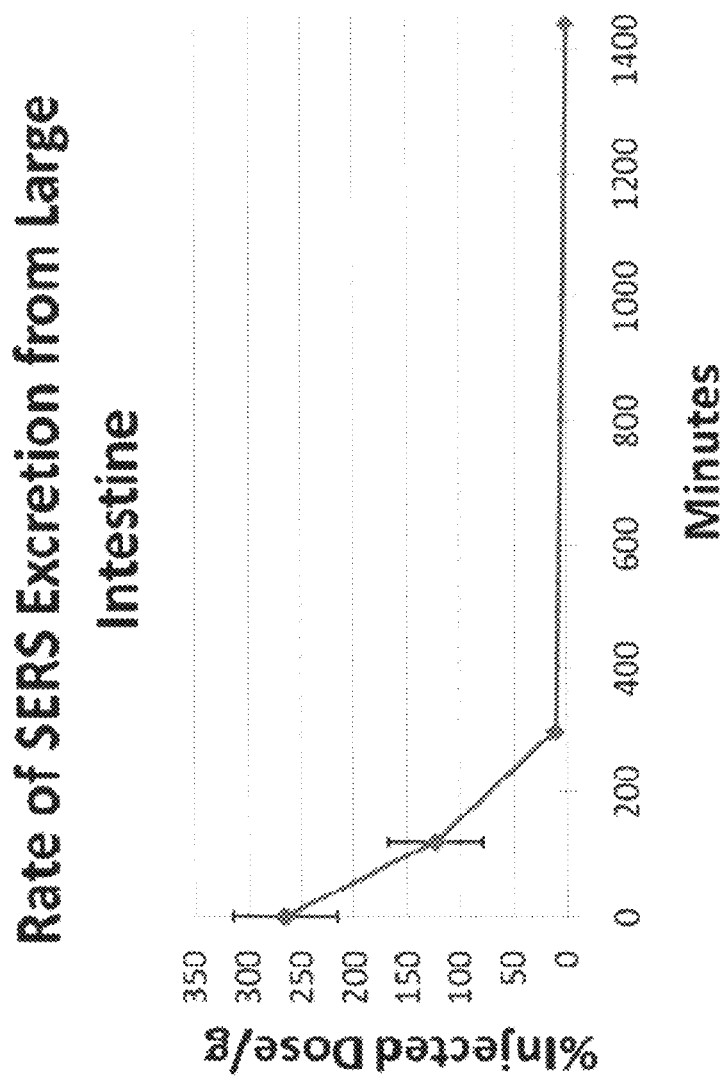
FIG. 4.8

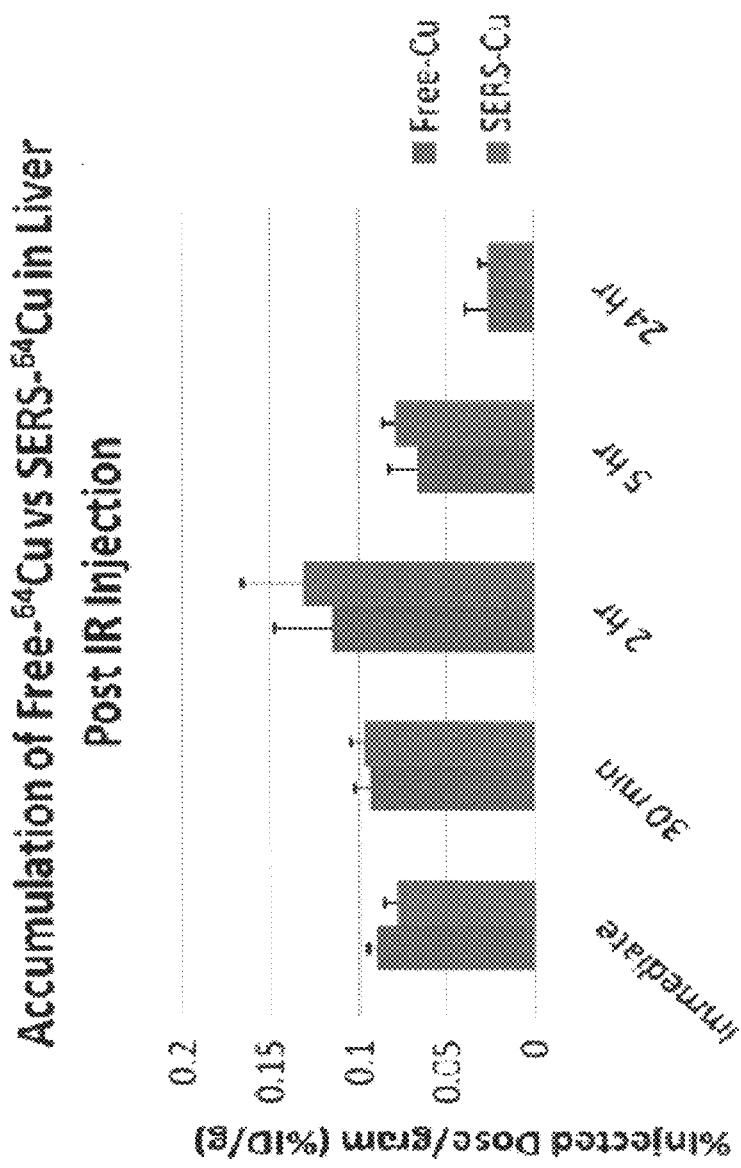
FIG. 4.9

```
                      SEQUENCE LISTING

<160> NUMBER OF SEQ ID NOS: 20

<210> SEQ ID NO 1
<211> LENGTH: 20
<212> TYPE: DNA
<213> ORGANISM: Artificial Sequence
<220> FEATURE:
<223> OTHER INFORMATION: Chemically synthesized forward primer sequence

<400> SEQUENCE: 1
ctctgaagtt taggccattg                                                   20

<210> SEQ ID NO 2
<211> LENGTH: 20
<212> TYPE: DNA
<213> ORGANISM: Artificial Sequence
<220> FEATURE:
<223> OTHER INFORMATION: Chemically synthesized reverse primer sequence

<400> SEQUENCE: 2
agttgctgta gggctttatg                                                   20

<210> SEQ ID NO 3
<211> LENGTH: 20
<212> TYPE: DNA
<213> ORGANISM: Artificial Sequence
<220> FEATURE:
<223> OTHER INFORMATION: Chemically synthesized forward primer sequence

<400> SEQUENCE: 3
tcatgacatt taatcaggca                                                   20

<210> SEQ ID NO 4
<211> LENGTH: 20
<212> TYPE: DNA
<213> ORGANISM: Artificial Sequence
<220> FEATURE:
<223> OTHER INFORMATION: Chemically synthesized reverse primer sequence

<400> SEQUENCE: 4
gtgtcaggat aggcaaaaag                                                   20

<210> SEQ ID NO 5
<211> LENGTH: 20
<212> TYPE: DNA
<213> ORGANISM: Artificial Sequence
<220> FEATURE:
<223> OTHER INFORMATION: Chemically synethsized forward primer sequence

<400> SEQUENCE: 5
ccagtacccc caggagaaga                                                   20
```

```
<210> SEQ ID NO 6
<211> LENGTH: 20
<212> TYPE: DNA
<213> ORGANISM: Artificial Sequence
<220> FEATURE:
<223> OTHER INFORMATION: Chemically synthesized reverse primer sequence

<400> SEQUENCE: 6
ttgttttctg ccagtgcctc                                                 20

<210> SEQ ID NO 7
<211> LENGTH: 20
<212> TYPE: DNA
<213> ORGANISM: Artificial Sequence
<220> FEATURE:
<223> OTHER INFORMATION: Chemically synthesized forward primer sequence

<400> SEQUENCE: 7
gggcttaagg gtgtctgagc                                                 20

<210> SEQ ID NO 8
<211> LENGTH: 20
<212> TYPE: DNA
<213> ORGANISM: Artificial Sequence
<220> FEATURE:
<223> OTHER INFORMATION: Chemically synthesized reverse primer sequence

<400> SEQUENCE: 8
caaagaagtt cctggcctcc                                                 20

<210> SEQ ID NO 9
<211> LENGTH: 20
<212> TYPE: DNA
<213> ORGANISM: Artificial Sequence
<220> FEATURE:
<223> OTHER INFORMATION: Chemically synthesized forward primer sequence

<400> SEQUENCE: 9
gaaggtgtgg ggaagcatta                                                 20

<210> SEQ ID NO 10
<211> LENGTH: 20
<212> TYPE: DNA
<213> ORGANISM: Artificial Sequence
<220> FEATURE:
<223> OTHER INFORMATION: Chemically synthesized reverse primer sequence

<400> SEQUENCE: 10
acattgccca agtctccaac                                                 20

<210> SEQ ID NO 11
<211> LENGTH: 20
<212> TYPE: DNA
<213> ORGANISM: Artificial Sequence
<220> FEATURE:
<223> OTHER INFORMATION: Chemically synthesized forward primer sequence

<400> SEQUENCE: 11
ctcttcgaga agtgcgaggt                                                 20

<210> SEQ ID NO 12
<211> LENGTH: 20
<212> TYPE: DNA
<213> ORGANISM: Artificial Sequence
<220> FEATURE:
<223> OTHER INFORMATION: Chemically synthesized reverse primer sequence
```

<400> SEQUENCE: 12
tcgatgtcaa tggtctggaa                                            20

<210> SEQ ID NO 13
<211> LENGTH: 20
<212> TYPE: DNA
<213> ORGANISM: Artificial Sequence
<220> FEATURE:
<223> OTHER INFORMATION: Chemically synthesized forward primer sequence

<400> SEQUENCE: 13
gctgaggcag aagggttatg                                            20

<210> SEQ ID NO 14
<211> LENGTH: 20
<212> TYPE: DNA
<213> ORGANISM: Artificial Sequence
<220> FEATURE:
<223> OTHER INFORMATION: Chemically synthesized reverse primer sequence

<400> SEQUENCE: 14
gcccccttga aaaagttcat                                            20

<210> SEQ ID NO 15
<211> LENGTH: 25
<212> TYPE: DNA
<213> ORGANISM: Artificial Sequence
<220> FEATURE:
<223> OTHER INFORMATION: Chemically synthesized forward primer sequence

<400> SEQUENCE: 15
agggtttcat cccaggatcg agcag                                      25

<210> SEQ ID NO 16
<211> LENGTH: 24
<212> TYPE: DNA
<213> ORGANISM: Artificial Sequence
<220> FEATURE:
<223> OTHER INFORMATION: Chemically synthesized reverse primer sequence

<400> SEQUENCE: 16
atcttcttcc agatggtgag cgag                                       24

<210> SEQ ID NO 17
<211> LENGTH: 22
<212> TYPE: DNA
<213> ORGANISM: Artificial Sequence
<220> FEATURE:
<223> OTHER INFORMATION: Chemically synthesized forward primer sequence

<400> SEQUENCE: 17
tttgtttgtg tgcttctgag cc                                         22

<210> SEQ ID NO 18
<211> LENGTH: 20
<212> TYPE: DNA
<213> ORGANISM: Artificial Sequence
<220> FEATURE:
<223> OTHER INFORMATION: Chemically synthesized reverse primer sequence

<400> SEQUENCE: 18
attctgttgc cacctttcgg                                            20

```
<210> SEQ ID NO 19
<211> LENGTH: 20
<212> TYPE: DNA
<213> ORGANISM: Artificial Sequence
<220> FEATURE:
<223> OTHER INFORMATION: Chemically synthesized forward primer sequence

<400> SEQUENCE: 19
ggcggactat gacttagttg                                              20

<210> SEQ ID NO 20
<211> LENGTH: 20
<212> TYPE: DNA
<213> ORGANISM: Artificial Sequence
<220> FEATURE:
<223> OTHER INFORMATION: Chemically synthesized reverse primer sequence

<400> SEQUENCE: 20
aaacaacaat gtgcaatcaa                                              20
```

RAMAN IMAGING DEVICES AND METHODS OF MOLECULAR IMAGING

CROSS-REFERENCE TO RELATED APPLICATION

This application claims priority to U.S. provisional application entitled, "RAMAN IMAGING DEVICES AND METHODS OF MOLECULAR IMAGING," having Ser. No. 61/311,840, filed on Mar. 9, 2010, which is entirely incorporated herein by reference.

This application is a continuation-in-part of U.S. patent application Ser. No. 12/598,780, filed on Nov. 4, 2009, now U.S. Pat. No. 8,795,628 which is a National Stage Entry of International Application No. PCT/US2008/062649, filed on May 5, 2008, which claims priority to and the benefit of U.S. Provisional Application No. 60/927,574 filed on May 4, 2007.

STATEMENT REGARDING FEDERALLY SPONSORED RESEARCH OR DEVELOPMENT

This invention(s) was made with government support under Grant Nos.: U54 CA119367 and U54 CA 136465-02, each were awarded by the National Institutes of Health. The government has certain rights in the invention(s).

BACKGROUND

Molecular imaging of living subjects provides the ability to study cellular and molecular processes that have the potential to impact many facets of biomedical research and clinical patient management. Imaging of small animal models is currently possible using positron emission tomography (PET), single photon emission computed tomography (SPECT), magnetic resonance imaging (MRI), computed tomography (CT), optical bioluminescence and fluorescence, high frequency ultrasound, as well as several other emerging modalities. However, no single modality currently meets the needs of high sensitivity, high spatial and temporal resolution, high multiplexing capacity, low cost, and high-throughput.

Raman spectroscopy can differentiate the spectral fingerprint of many molecules, resulting in very high multiplexing capabilities. Narrow spectral features are easily separated from the broadband autofluorescence since Raman is a scattering phenomenon, as opposed to absorption/emission in fluorescence, and Raman active molecules are more photostable compared with fluorophores that are rapidly photobleached. Unfortunately, the precise mechanism for photobleaching is not well understood. However, it has been linked to a transition from the excited singlet state to the excited triplet state. Photobleaching is significantly reduced for single molecules adsorbed onto metal particles due to the rapid quenching of excited electrons by the metal surface, thus preventing excited-state reactions and hence photobleaching. However, the inherently weak magnitude of the Raman effect (approximately one photon is inelastically scattered for every $10^7$ elastically scattered photons) limits the sensitivity, and as a result the biomedical applications of Raman spectroscopy.

The discovery of the surface enhanced Raman scattering (SERS) phenomenon offers an exciting opportunity to overcome this lack of sensitivity and introduce Raman spectroscopy into new fields. SERS is a plasmonic effect where molecules adsorbed onto nano-roughened noble metal surfaces (e.g., gold) experience a dramatic increase in the incident electromagnetic field resulting in high Raman intensities comparable to fluorescence.

SUMMARY

In accordance with the purpose(s) of the present disclosure, as embodied and broadly described herein, embodiments of the present disclosure, in one aspect, relate to Raman imaging devices (e.g., Raman endoscope probes), methods of using Raman agents and Raman imaging devices to image or detect a signal, and the like.

An embodiment of the present disclosure includes a method of imaging that includes: administering at least a first type of Raman agent to a subject, wherein the Raman agent has an affinity for a specific target; introducing a Raman imaging device to the subject; positioning the Raman imaging device adjacent the specific target; exposing the specific target to a light beam from the Raman imaging device, wherein the light beam is scattered by the first type of Raman agent that associated with the specific target, wherein the light beam that is scattered is referred to as a Raman scattered light energy; and detecting the Raman scattered light using the Raman imaging device, using the Raman scattered light energy to form an image.

An embodiment of the present disclosure includes a method of imaging that includes: administering a plurality of types of Raman agents to a subject, wherein at least two types of Raman agents have an affinity for a different target; positioning the Raman imaging device adjacent an area that includes one or more of the different targets; exposing the area to a light beam from the Raman imaging device, wherein if one or more of the plurality of Raman agents is present, the light beam is scattered, wherein the light beam that is scattered is referred to as a Raman scattered light energy, wherein each different type of Raman agent has a detectably different Raman scattered light energy; detecting the Raman scattered light using the Raman imaging device; and analyzing the scattered light to determine the type of Raman agent, wherein the type of Raman agent determines the target detected.

An embodiment of the present disclosure includes a method of monitoring a biological agent that includes: introducing a first type of biological agent that includes a first type of Raman agent to a sample or a subject; positioning the Raman imaging device adjacent to an area; exposing the area to a light beam, wherein if the biological agent including a Raman agent is present, the light beam is scattered, wherein the light beam that is scattered is referred to as a Raman scattered light energy; and detecting the Raman scattered light using the Raman imaging device, wherein the detection of the Raman scattered light indicates that the biological agent is present in the area.

An embodiment of the present disclosure includes a method of imaging cells that includes: administering a plurality of types of Raman agents to a subject, wherein at least one type of Raman agent has an affinity for a target, wherein at least one type of Raman agent is untargeted; positioning the Raman imaging device adjacent an area that includes one or more of the different targets; exposing the area to a light beam from the Raman imaging device, wherein if one or more of the plurality of Raman agents is present, the light beam is scattered, wherein the light beam that is scattered is referred to as a Raman scattered light energy, wherein each different type of Raman agent has a detectably different Raman scattered light energy; detecting the Raman scattered light using the Raman imaging device; analyzing the scattered light to determine the type of Raman agent, wherein the type of Raman agent determines the target detected; and analyzing the scattered light to determine the ratio of the specific binding Raman agent to non-specific binding Raman agent, wherein the ratio provides an estimate of the bound Raman agents.

BRIEF DESCRIPTION OF THE DRAWINGS

Many aspects of the disclosed devices and methods can be better understood with reference to the following drawings. The components in the drawings are not necessarily to scale, emphasis instead being placed upon clearly illustrating the relevant principles. Moreover, in the drawings, like reference numerals designate corresponding parts throughout the several views.

FIG. 1.1 describes a number of types of SERS nanoparticles (upper left schematic) where each unique SERS reporter can be interchanged and each produce a unique Raman spectral signature, as shown for example by the bottom three spectra.

FIG. 2.1 illustrates a diagrammatic representation of the PEG-R—Si—Au—NP.

FIG. 2.2 illustrates gold concentrations in the liver and spleen. The bars represent the mean±S.E.M. for the concentration of gold in the liver and spleen as determined by ICP-MS at 5 M (5 min), 2 H (2 hours), 24 H (24 hours), 1 W (1 week), 2 W (2 weeks) following IV PEG-R—Si—Au—NP administration. Significant differences: *$P<0.05$, difference from PR PEG-R—Si—Au—NP; $^aP<0.05$, difference between time-points within the same group and sex (superscript numbers represent the statistically significant time-point groups); and $^bP<0.05$, difference between sexes. Three-way RM ANOVA with post hoc Student-Newman-Keuls test FIG. 2.3 illustrates photomicrographs of liver from male mice following IV PEG-R—Si—Au—NP administration. FIGS. 2.3a to 2.3e illustrate H&E stained sections of control animals, showing resident macrophages/Kupffer cells (white arrow). 1000× magnification, bar=10 microns. FIGS. 2.3f to 2.3j illustrate H&E stained sections of animals following IV PEG-R—Si—Au—NP administration, showing resident macrophages/Kupffer cells (white arrow); free, fine, black pigment within sinusoids (black asterisk); and resident macrophages/Kupffer cells with intracytoplasmic, fine, black pigment (black arrow). 1000× magnification, bar=10 microns. FIGS. 2.3k to 2.3o illustrate TUNEL stained sections of animals following IV PEG-R—Si—Au—NP administration, showing resident macrophages/Kupffer cells (white arrow); resident macrophages/Kupffer cells with intracytoplasmic, fine, black pigment (black arrow); and resident macrophages/Kupffer cells with intracytoplasmic, fine, black pigment that demonstrated diffuse, brown, intranuclear staining with TUNEL (black arrowhead). 1000× magnification, bar=10 microns. FIGS. 2.3p to 2.3t illustrates bright (left) and dark (right) field TEM sections of animals following IV PEG-R—Si—Au—NP administration. 59,000× magnification, bar=200 nanometers.

FIG. 2.4 illustrates the change in antioxidant enzyme gene expression within the liver tissue following IV PEG-R—Si—Au—NP administration. The bars represent the mean±S.E.M. for the fold change in antioxidant enzyme gene expression compared to control cells at 5 M (5 min), 2 H (2 hours), 24 H (24 hours), 1 W (1 week), 2 W (2 weeks) following IV PEG-R—Si—Au—NP administration. Significant differences: *$P<0.05$, difference between control animals (IV saline) within the same sex and $^aP<0.05$, difference between time-points within the same group and sex (superscript numbers represent the statistically significant time-point groups). Two-way RM ANOVA with post hoc Student-Newman-Keuls test.

FIG. 2.5 illustrates the change in inflammatory gene expression within the liver following IV PEG-R—Si—Au—NP administration. The bars represent the mean±S.E.M. for the fold change in inflammatory gene expression compared to control cells at 5 M (5 min), 2 H (2 hours), 24 H (24 hours), 1 W (1 week), 2 W (2 weeks) following IV PEG-R—Si—Au—NP administration. Significant differences: *$P<0.05$, difference between control animals (IV saline) within the same sex and $^aP<0.05$, difference between time-points within the same group and sex (superscript numbers represent the statistically significant time-point groups). Two-way RM ANOVA with post hoc Student-Newman-Keuls test.

FIG. 2.6 illustrates photomicrographs of liver from male mice following PR PEG-R—Si—Au—NP administration. FIGS. 2.6a to 2.6e illustrate H&E stained sections of control animals, showing resident macrophages/Kupffer cells (white arrow). 1000× magnification, bar=10 microns. FIGS. 2.6f to 2.6j illustrate H&E stained sections of animals following PR PEG-R—Si—Au—NP administration, showing resident macrophages/Kupffer cells (white arrow). 1000× magnification, bar=10 microns. FIGS. 2.6k to 2.6o illustrates TUNEL stained sections of animals following PR PEG-R—Si—Au—NP administration, showing resident macrophages/Kupffer cells (white arrow); and resident macrophages/Kupffer cells that demonstrated diffuse, brown, intranuclear staining with TUNEL (white arrowhead). 1000× magnification, bar=10 microns. FIGS. 2.6p to 2.6t illustrate bright (left) and dark (right) field TEM sections of animals following PR PEG-R—Si—Au—NP administration. 21,000× magnification, bar=500 nanometers.

FIG. 2.7 illustrates Table 1. Table 1 shows the histological results from liver tissue following PEG-R—Si—Au—NP administration. The liver from each mouse is represented by a single number corresponding to the severity of the change observed. 0=Normal; 1=Minimal change; 2=Mild change; 3=Moderate change; 4=Severe change.

FIG. 2.8 illustrates serial ECG traces for a representative male and female mouse prior to (baseline) and following (1 and 2 weeks) either intravenous (IV) or per rectum (PR) administration of saline or PEG-R—Si—Au—NP.

FIG. 2.9 illustrates photomicrographs of liver from female mice following IV PEG-R—Si—Au—NP administration. FIGS. 2.9a to 2.9e illustrate H&E stained sections of control animals, showing resident macrophages/Kupffer cells (white arrow). 1000× magnification, bar=10 microns. FIGS. 2.9f to 2.9j illustrate H&E stained sections of animals following IV PEG-R—Si—Au—NP administration, showing resident macrophages/Kupffer cells (white arrow); free, fine, black pigment within sinusoids (black asterisk); and resident macrophages/Kupffer cells with intracytoplasmic, fine, black pigment (black arrow). 1000× magnification, bar=10 microns. FIGS. 2.9k to 2.9o illustrate TUNEL stained sections of animals following IV PEG-R—Si—Au—NP administration, showing resident macrophages/Kupffer cells (white arrow); resident macrophages/Kupffer cells with intracytoplasmic, fine, black pigment (black arrow); and resident macrophages/Kupffer cells that demonstrated diffuse, brown, intranuclear staining with TUNEL (white arrowhead). 1000× magnification, bar=10 microns. FIGS. 2.9p to 2.9t illustrate bright (left) and dark (right) field TEM sections of animals following IV PEG-R—Si—Au—NP administration. 59,000× magnification, bar=200 nanometers.

FIGS. 2.10 illustrate photomicrographs of liver from female mice following PR PEG-R—Si—Au—NP administration. FIGS. 2.10a to 2.10e illustrate H&E stained sections of control animals, showing resident macrophages/Kupffer cells (white arrow). 1000× magnification, bar=10 microns. FIGS. 2.10f to 2.10j illustrate H&E stained sections of animals following PR PEG-R—Si—Au—NP administration, showing resident macrophages/Kupffer cells (white arrow). 1000× magnification, bar=10 microns. FIGS. 2.10k to 2.10o illustrate TUNEL stained sections of animals following PR PEG-R—Si—Au—NP administration, showing resident macrophages/Kupffer cells (white arrow); and resident macrophages/Kupffer cells that demonstrated diffuse, brown, intranuclear staining with TUNEL (white arrowhead). 1000× magnification, bar=10 microns. FIGS. 2.10p to 2.10t illustrate bright (left) and dark (right) field TEM sections of animals following PR PEG-R—Si—Au—NP-administration. 21,000× magnification, bar=500 nanometers.

FIG. 2.11 illustrates an experimental protocol summary.

FIG. 2.12 illustrates a Table describing the cardiovascular and biometric measurements. The values represent the mean±S.E.M for male and female mice prior to (baseline) and following (1 and 2 weeks) either intravenous (IV) or per rectum (PR) administration of saline or PEG-R—Si—Au—NP. Significant differences: $^{a}$P<0.05, difference between time-points within the same group and sex (superscript numbers represent the statistically significant time-point groups. i: Baseline; ii: Week 1), and $^{b}$P<0.05, difference between sexes at baseline. Two-way RM ANOVA with post hoc Student-Newman-Keuls test.

FIG. 2.13 illustrates a Table describing hematological and biochemical measurements. The values represent the mean±S.E.M for male and female mice prior to (baseline) and following (1 week) either intravenous (IV) or per rectum (PR) administration of saline or PEG-R—Si—Au—NP. Significant differences: $^{a}$P<0.05, difference between time-points within the same group and sex; $^{b}$P<0.05, difference between control animals (IV or PR saline) within the same sex; and $^{c}$P<0.05, difference between sexes at baseline. Three-way RM ANOVA with post hoc Student-Newman-Keuls test.

FIG. 2.14 illustrates a Table describing TUNEL stain results from liver tissue following PEG-R—Si—Au—NP administration in a representative male and female mouse. The liver from a representative mouse from each group was examined using a TUNEL stain. Each number represents the average number of cells which were positive for the TUNEL stain per 100 cells examined.

FIG. 2.15 illustrates a Table describing primer sequences of antioxidant enzyme and inflammatory genes. WBC: White Blood Cells; RBC: Red Blood Cells; Hb: Hemoglobin; Hct: Hematocrit; MCV: Mean Cell Volume; MCH: Mean Corpuscular Hemoglobin; ALT: Alanine Aminotransferase; AST: Aspartate Aminotransferase; γ-GT: Gamma-Glutamyl Transpeptidase.

FIG. 3.1 illustrates microPET imaging in mice after either intravenous (IV) or intrarectal (IR) administration of Cu-64 labeled SERS nanoparticles at various time points post injection. Notice the differences in distribution between the mouse receiving IV injection (top panel) versus the mouse receiving IR injection (bottom panel) of $^{64}$Cu-SERS nanoparticles. The SERS nanoparticles appear to localize in the liver immediately after IV injection and remain in the liver over 24 hours whereas the SERS nanoparticles injected IR remain localized in the colon over 24 hours post IR injection. Colored scale bar to the right represents $^{64}$Cu-SERS uptake where red represents most uptake and black represents no uptake.

FIG. 3.2a illustrates the conjugation process of our SERS nanoparticles with tumor targeting heptapeptide. FIG. 3.2b illustrates TEM image of a derivatized SERS nanoparticle. Notice the dark 60 nm gold core encapsulated in glass making the total size of the SERS nanoparticle on the order of 120 nm.

FIG. 3.3a illustrates a schematic of our newly developed Raman endoscope. Notice how the Raman component would be inserted through the 6 mm accessory channel of a conventional clinical colonoscope. The endoscope would be comprised of a fiber optic bundle with a single excitation fiber and a bundle of collection fibers for maximum signal collection. Tumor targeted SERS nanoparticles would be locally administered to suspicious polyps and then rinsed with water. Light would then be shined on the polyp to determine specific binding to dysplastic lesions. FIG. 3.3b illustrates the newly developed prototype Raman endoscopic probe for early detection of colorectal cancer.

FIG. 3.4 illustrates the binding efficiency of (+) heptapeptide SERS nanoparticles on tumor vs normal colon tissue. In particular, FIG. 3.4a illustrates a digital photo of malignant tumor tissue and normal adjacent tissue. FIG. 3.4b illustrates each tissue exposed to (+) heptapeptide SERS nanoparticles for 10 min. FIG. 3.4c illustrates a Raman image of the tissues using our Raman mapping system. FIG. 3.4d illustrates an overlay of Raman intensity map over digital photo of fresh tissue samples. Notice the increased binding of the (+) heptapeptide SERS nanoparticles throughout the entire tumor tissue as opposed to the decreased localized non-specific binding seen in the normal adjacent tissue.

FIG. 3.5 illustrates the targeting efficiency ratios post-processed from Raman images. The left bar depicts the effective binding ratio of the (+) heptapeptide SERS to tumor tissue vs normal tissue. Whereas the right bar depicts the effective binding ratio of (+) SERS to (−) SERS in tumor tissue samples.

FIG. 4.1 illustrates MicroPET images of the accumulation of $^{64}$Cu-SERS nanoparticles post IV injection (top panel) versus post IR injection (bottom panel). The images represent a coronal slice of a single mouse taken at various time points (immediately, 30 min, 2 h, 5 h, and 24 h) after either IV or IR injection. Notice the significant difference in accumulation of $^{64}$Cu-SERS nanoparticles in mice receiving an IV injection where uptake is localized to the liver versus mice receiving and IR injection where uptake is localized in the colon. Colored scale bar to the right of each image represents $^{64}$Cu-SERS uptake where red represents most uptake and black represents no uptake in units of % ID/g.

FIG. 4.2 illustrates biodistribution data taken from various excised organs after either IV or IR injection of SERS nanoparticles at (FIG. 4.2a) 2 hr, (FIG. 4.2b) 5 hr, and (FIG. 4.2c) 24 hr post injection. Notice significant differences represented by *(p<0.05) between each of the injection groups particularly in the accumulation of SERS nanoparticles in almost all the tissues after IV injection as compared to those mice injected IR. This data shows that mice injected IR had localized accumulation of SERS nanoparticles to predominantly the large intestine and cecum out to 5 hours post injection. However, by 24 hours post injection most of the SERS nanoparticles had cleared, presumably via the feces, whereas the mice injected IV still showed uptake in most tissues as seen in the bottom graph.

FIG. 4.3 illustrates Raman images of various excised tissues at 2 hours post injection (FIG. 4.3a) spleen IV injected, (FIG. 4.3b) kidney IV injected, (FIG. 4.3c) lung IV injected, (FIG. 4.3d) liver IV injected, (FIG. 4.3e) colon IR injected. These organs were chosen to image with Raman mapping based on the increased accumulation of SERS nanoparticles seen from the biodistribution data. These Raman intensity maps confirm the presence of SERS nanoparticles within these tissues of interest. Scale bar to the right represents Raman intensity where bright red represents the highest Raman signal and black represents no associated Raman signal.

FIG. 4.4 illustrates TEM images of SERS nanoparticle accumulation in liver tissue at 5 min and 2 weeks post injection of SERS nanoparticles. (FIG. 4.4a) Bright field scanning transmission electron microscopy (STEM) image of liver tissue from mouse injected IR at 5 min. (FIG. 4.4b) Bright field STEM image of liver tissue from mouse injected IV at 5 min. (FIG. 4.4c) Bright field STEM image of liver tissue from mouse injected IR at 2 weeks. (FIG. 4.4d) Bright field STEM image of liver tissue from mouse injected IV at 2 weeks. Notice the absence of SERS nanoparticles in the liver tissue from the mice that received an IR injection in panels FIG. 4.4a and FIG. 4.4c.

FIG. 4.5 illustrates a TEM image of our plain SERS nanoparticles. Notice the 60 nm gold core (black) surrounded by a silica shell at roughly 30 nm, making the entire nanoparticle approximately 120 nm in diameter.

FIG. 4.6 illustrates the conjugation process of our SERS nanoparticles with DOTA chelator for radiolabeling with $^{64}Cu$ (see methods section for more details). Briefly, SERS nanoparticles were PEGylated with a 5:1 ratio of short ($PEG_{2000}$):long ($PEG_{5000}$) chains. Only the long $PEG_{5000}$ chains had a functional handle for DOTA chelator attachment. $^{64}Cu$ was then incubated with the DOTA-SERS nanoparticles for approximately 60 min at 37° C. for radiolabeling. The end product was then washed 3 times to remove any unbound radioactive $^{64}Cu$ from the final $^{64}Cu$-DOTA-SERS product. This method attaches ~60,000 $^{64}Cu$ molecules per nanoparticle (~1 $^{64}CU$ molecule per 3 $nm^2$ surface area).

FIG. 4.7 illustrates a time-activity curve demonstrating dynamic uptake of SERS nanoparticles over the first 13 minutes after IV administration within the liver (diamond), spleen (square) and lungs (triangle). Notice the immediate accumulation of SERS nanoparticles in both the liver and the spleen where the accumulation appears to plateau after approximately 2 minutes. Also notice the initial uptake of SERS nanoparticles in the lungs with a maximum accumulation at approximately 15 seconds followed by a relatively rapid clearance.

FIG. 4.8 illustrates a time activity curve demonstrating the rate at which the SERS nanoparticles are excreted from the large intestine after IR administration. Notice the rapid excretion of SERS nanoparticles after only 5 hours post injection. Less than 1% ID/g remains in the bowel after 24 hours post injection.

FIG. 4.9 illustrates a graph depicting the distribution patterns in the liver of either free $^{64}Cu$ after IR injection into mice or $^{64}Cu$-labeled SERS nanoparticles after IR injection into mice over 24 hours. Notice the similarirty between the groups, thus suggesting that the very little % ID/g that is actually detected in the liver after $^{64}Cu$-SERS injection is most likely due to the minimal dissociation of the $^{64}Cu$ and not the actual SERS nanoparticles themselves.

DETAILED DESCRIPTION

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of chemistry, biochemistry, biology, molecular biology, imaging, and the like, which are within the skill of the art.

The following examples are put forth so as to provide those of ordinary skill in the art with a complete disclosure and description of how to perform the methods and use the probes disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

Before the embodiments of the present disclosure are described in detail, it is to be understood that, unless otherwise indicated, the present disclosure is not limited to particular materials, reagents, reaction materials, manufacturing processes, or the like, as such can vary. It is also to be understood that the terminology used herein is for purposes of describing particular embodiments only, and is not intended to be limiting. It is also possible in the present disclosure that steps can be executed in different sequence where this is logically possible.

It must be noted that, as used in the specification and the appended claims, the singular forms "a," "an," and "the" include plural referents unless the context clearly dictates otherwise. Thus, for example, reference to "a compound" includes a plurality of compounds. In this specification and in the claims that follow, reference will be made to a number of terms that shall be defined to have the following meanings unless a contrary intention is apparent.

Definitions

In describing and claiming the disclosed subject matter, the following terminology will be used in accordance with the definitions set forth below.

The term "Surface-Enhanced Raman Scattering (SERS)" refers to the increase in Raman scattering exhibited by certain molecules in proximity to certain metal surfaces. (see, U.S. Pat. No. 5,567,628) The SERS effect can be enhanced through combination with the resonance Raman effect. The surface-enhanced Raman scattering effect is even more intense if the frequency of the excitation light is in resonance with a major absorption band of the molecule being illuminated. In short, a significant increase in the intensity of Raman light scattering can be observed when molecules are brought into close proximity to (but not necessarily in contact with) certain metal surfaces. In an embodiment, the metal surfaces can be "roughened" or coated with minute metal particles. Metal colloids also show this signal enhancement effect. The increase in intensity can be on the order of several million-fold or more.

The term "reporter compound" can refer to a Raman-active label. The term "Raman-active label" can refer to a substance that produces a detectable Raman spectrum, which is distinguishable from the Raman spectra of other components present, when illuminated with a radiation of the proper wavelength.

As used herein, the term "Raman agent" refers to the compounds or structures of the present disclosure that are capable of serving as imaging agents either alone or in combination with attached molecules (e.g., antibodies, proteins, peptides, small organic molecules, aptamers, and the like).

The term "administration" refers to introducing a Raman agent (or a compound, cell, or virus, including the Raman agent) of the present disclosure into a subject. The preferred route of administration of the compounds is intravenous. However, any route of administration, such as oral, topical, subcutaneous, peritoneal, intraarterial, inhalation, vaginal, rectal, nasal, introduction into the cerebrospinal fluid, or instillation into body compartments can be used. In an embodiment, the Raman agent is administered locally (e.g., colon) so that it is not systemically distributed throughout the body.

In accordance with the present disclosure, "a detectably effective amount" of the Raman agent (e.g., SERS nanoparticle) of the present disclosure is defined as an amount sufficient to yield an acceptable image using equipment that is available for pre-clinical or clinical use. In an embodiment, a detectably effective amount of the Raman agent of the present disclosure may be administered in more than one injection. The detectably effective amount of the Raman agent of the present disclosure can vary according to factors such as the degree of susceptibility of the individual, the age, sex, and weight of the individual, idiosyncratic responses of the individual, the dosimetry, and the like. Detectably effective amounts of the Raman agent of the present disclosure can also vary according to instrument and digital processing related factors. Optimization of such factors is well within the level of skill in the art.

As used herein, the term "subject" or "host" includes humans and mammals (e.g., mice, rats, pigs, cats, dogs, and horses,). Typical subjects to which compounds of the present disclosure may be administered will be mammals, particularly primates, especially humans. For veterinary applications, a wide variety of subjects will be suitable, e.g., livestock such as cattle, sheep, goats, cows, swine, and the like; poultry such as chickens, ducks, geese, turkeys, and the like; and domesticated animals particularly pets such as dogs and cats. For diagnostic or research applications, a wide variety of mammals will be suitable subjects, including rodents (e.g., mice, rats, hamsters), rabbits, primates, and swine such as inbred pigs and the like. The term "living subject" refers to host or organisms noted above that are alive. The term "living subject" refers to the entire host or organism and not just a part excised (e.g., a liver or other organ) from the living subject.

As used herein, the term "in vivo imaging" refers to imaging living subjects (e.g., human or mammals).

Discussion

In accordance with the purpose(s) of the present disclosure, as embodied and broadly described herein, embodiments of the present disclosure, in one aspect, relate to Raman imaging devices (e.g., Raman endoscope probes), methods of using Raman agents and Raman imaging devices to image or detect a signal, and the like.

Embodiments of the present disclosure seek to improve detection of a disease or condition during conventional endoscopic, laparoscopic, intraoperative, or surgical procedures. Embodiments of the present disclosure can accomplish this through molecular imaging using a Raman imaging device. In an embodiment, the Raman imaging device can be a Raman endoscope probe that can be used in an endoscope or a handheld Raman spectroscopy imaging device. The molecular imaging can be accomplished by using a Raman agent that produce a Raman light scattering signal and a Raman imaging device that can excite the Raman agents with light and sensitively detect Raman scattered light energy signals emitted from the Raman agent. Embodiments of the Raman imaging device can be used in conjunction with Raman agents that target a specific disease to detect it earlier and at its margins with greater sensitivity than what is currently used.

Embodiments of the present disclosure include a diagnostic tool (e.g., Raman imaging device such as a Raman endoscope probe or handheld device) and methods for identification of a disease or condition in subjects (e.g., human) who are undergoing a surgical, laparoscopic, intraoperative, or endoscopic procedure, where a device including the Raman imaging device (such an endoscope including the Raman endoscope probe or handheld device) is inserted into the body (e.g., cervix, bladder, bronchioles, esophagus, stomach, colon, rectum, skin, oral mucosa, and intraoperatively or laparoscopically into an organ, and the like) or placed over the region of interest (during surgical or intraoperative procedures). Raman agents can be conjugated with one or more disease targeting ligands and administered to the subject. The targeted Raman agents then sensitively and specifically bind to the cells, proteins, etc related to the disease of interest and their localization can be detected using the Raman imaging device. The technique acts as an in-vivo histopathological tool assisting the physician to immediately identify a diseased area and its margins without having to involve a third party pathologist.

The principle by which embodiments of the present disclosure operate is based on the Raman Effect. When light is scattered from a molecule most photons are elastically scattered. However, a small fraction of light is scattered at optical frequencies different from and usually lower than the frequency of the incident photons. The process leading to this inelastic scatter is termed the Raman Effect. However, this effect is very weak, only producing one inelastically scattered photon for every 10 million elastically scattered photons. Therefore surface enhanced Raman scattering (SERS) agents will be used. SERS is a plasmonic effect where small molecules adsorbed onto a nano-roughened noble metal surface, for example, experience a dramatic increase in the incident electromagnetic field resulting in several orders of magnitude higher Raman intensity. The increase in the Raman Effect allows embodiments of the present disclosure to detect pM concentrations of Raman agents with the Raman imaging device. The Raman agents can be selected so that they include unique Raman active molecules (that can be interchanged for multiplexing capabilities) adsorbed onto a metal core. In addition, the Raman agents can be conjugated to a disease targeting ligand that has an affinity for and a binding potential to the diseased area as opposed to normal tissue. Once the Raman agents have been conjugated to the appropriate disease targeting ligand, the Raman agents can be administered to the subject and the Raman agents are given an appropriate amount of time to bind to the targeted disease (e.g., diseased tissue or cells or compounds associated with the disease). Subsequently, using the Raman imaging device, a light beam can be directed onto the suspected diseased area to detect inelastic scattering (Raman scattering light energy) coming from disease targeted Raman agents.

Thus far, the use of Raman spectroscopy as a clinical tool has been limited to looking at the intrinsic molecular changes of diseased versus normal tissues that are often difficult to discern due to the weak effect of Raman scattering resulting in a low signal to noise ratio. As mentioned above, embodiments of the present disclosure include using Raman agents to detect a signal from the diseased area of interest. The Raman agents give a much more intense Raman signal than the intrinsic Raman scattering from the tissues themselves (about $10^7$ orders of magnitude greater) allowing us to achieve at least pM sensitivity.

Embodiments of the Raman imaging device can take the form of several instruments such as, but not limited to, an endoscope, a handheld Raman imaging device, or even a microscope. In general, the Raman imaging device includes a light source (e.g., a laser) or is adapted to direct a light source (e.g., uses a fiber to guide the light) that may be generated separately from the Raman imaging device, and a device or structure to receive or detect Raman scattered light energy (e.g., uses a fiber to collect light). Optionally the Raman imaging device includes one or more lenses to guide the light and the scattered Raman light energy and/or one or more filters to select certain wavelengths of light and/or scattered Raman light energy. The resulting light can then be measured by a device such as a spectrometer/CCD. In an embodiment, the Raman imaging device or a system including the Raman imaging device can include collection and measurement devices or instruments to collect and measure the scattered Raman light energy.

In an embodiment, the Raman imaging device can be a Raman endoscope probe. In an embodiment, the Raman endoscope probe can be used with an endoscope. Although a specific embodiment, a Raman endoscope probe, is discussed in detail below, embodiments of the present disclosure are not limited to Raman endoscope probes and portions of the discussion below describing the principles of operation and use can be applied to other Raman imaging devices such as those described herein.

In general, an endoscope includes one or more channels down the length of the endoscope. At least one channel can accept the Raman endoscope probe. The Raman endoscope probe can be inserted into the endoscope before or after the endoscope is introduced into the subject.

Embodiments of the Raman endoscope probe can include a fiber bundle, one or more lenses for collimating a light beam (e.g., a laser at a wavelength that the Raman agents scatter the light) and for focusing the Raman scattered light energy, and optionally filters for delivering and collecting the appropriate light signals. Other components of the Raman endoscope probe include a spectrometer and charge-coupled device (CCD) camera for collection and measurement of inelastically scattered light. The fiber bundle can be used to direct the light and collecting Raman scattered light energy.

The Raman agents can include Raman compounds and Raman nanoparticles. In an embodiment, the Raman compounds can include reporter compounds conjugated with one or more distinct targeting agents, both of which are described in more detail below. In an embodiment, the Raman nanoparticles include, but are not limited to, SERS nanoparticles, composite organic inorganic nanoparticles (COINS), Single walled nanotubes (SWNTs), methylene blue dye (other Raman active dyes), and the like. Each of the Raman nanoparticles can include targeting ligands (e.g., proteins) so that targeted areas (e.g., organs (e.g., colon), and the like) can be imaged.

In an embodiment, the SERS nanoparticle includes, but is not limited to, a core, a reporter compound, and an encapsulant material. The encapsulant material covers and protects the core and reporter compounds. The reporter compounds are attached to the core. The core can be made of materials such as, but not limited to, copper, silver, gold, and combinations thereof, as well as of other metals or metalloids. Different types of SERS nanoparticles can be selected, where each SERS nanoparticle has a different Raman signature. Thus, the use of different SERS nanoparticles enables multiplexing. Additional details regarding this particular type of SERS nanoparticle is provided in WO 2006/073439, U.S. Pat. No. 6,514,767, and U.S. Patent Application No. 60/557,729, each of which are incorporated herein by reference as they pertain to the detailed description of each application or patent and as they relate to SERS nanoparticles and SACNs.

In an embodiment, one type of SERS nanoparticle includes Surface Enhanced Spectroscopy-Active Composite Nanoparticles (SACNs). SACNs and methods of making SACNs are described in WO 2006/073439, U.S. Pat. No. 6,514,767, and U.S. Patent Application No. 60/557,729, each of which is incorporated herein by reference as they pertain to the detailed description of each application or patent and as they relate to SACNs. Embodiments of the SACNs can include a SERS nanoparticle, a submonolayer, monolayer, or multilayer of reporter molecules in close proximity to the metal surface, and an encapsulating shell (e.g., a polymer, glass (SiO:), or other dielectric material). In an embodiment, the reporter compound is disposed at the interface between the SERS nanoparticle and the encapsulant. In an embodiment, a SACN comprises (i) a metal nanoparticle core (e.g., Au or Ag), (ii) a Raman-active reporter (reporter compound), that gives a unique vibrational signature, and (iii) an SiO: encapsulant that "locks" the reporter molecules in place while also providing a highly compatible surface for subsequent immobilization of biomolecules. The glass coating can also stabilize the particles against aggregation and can prevent competitive adsorption of unwanted species. In an embodiment, the SERS nanoparticles are comprised of polymer coatings adjacent to the nanoparticle.

As used herein, the term "reporter compound" includes Raman-active compounds that produce a unique SERS signature in response to excitation by a laser. In certain embodiments, Raman-active organic compounds are polycyclic aromatic or heteroaromatic compounds. In an embodiment, the reporter compound can include, but is not limited to, 4-mercaptopyridine (4-MP); trans-4,4'bis (pyridyl)ethylene (BPE); quinolinethiol; 4,4'-dipyridyl, 1,4-phenyldiisocyanide; mercaptobenzamidazole; 4-cyanopyridine; 1',3,3,3',3'-hexamethylindotricarbocyanine iodide; 3,3'-diethyltiatricarbocyanine; malachite green isothiocyanate; bis-(pyridyl)acetylenes; Bodipy; TRIT (tetramethyl rhodamine isothiol); NBD (7-nitrobenz-2-oxa-1,3-diazole); Texas Red dye; phthalic acid; terephthalic acid; isophthalic acid; cresyl fast violet; cresyl blue violet; brilliant cresyl blue; para-aminobenzoic acid; erythrosine; biotin; digoxigenin; 5-carboxy-4',5'-dichloro-2',7'-dimethoxy fluorescein; 5-carboxy-2',4',5',7'-tetrachlorofluorescein; 5-carboxyfluorescein; 5-carboxy rhodamine; 6-carboxyrhodamine; 6-carboxyletramethyl amino phthalocyanines; azomethines; cyanines; xanthines; succinylfluoresceins; aminoacridine; fullerenes; organocyanides (e.g., isocyanide), methylene blue indigo carmine, and indocyanine green (ICG), and the like, and combinations thereof.

A COIN includes several fused or aggregated primary metal crystal particles with the Raman-active organic compounds (reporter compound) adsorbed on the surface, within the junctions of the primary particles, or embedded in the crystal lattice of the primary metal particles. The primary metal crystal particles are about 15 nm to 30 nm, while the fused or aggregated COIN is about 50 nm to about 200 nm. The primary metal crystal particle is made of materials such as, but not limited to, gold, silver, platinum copper aluminum, and the like. The Raman-active organic compound refers to an organic molecule that produces a unique SERS signature in response to excitation by a laser. Additional details regarding COINS are described in U.S. Patent Applications 20050142567, 20060234248, and 20070048746, each of which is incorporated herein by reference for the corresponding discussion.

COINs can also serve as Raman nanoparticles to provide imaging signals. The COINs can be functionalized so they have better solubility in blood and can target potential targets in a living subject. Multiple COINs can be used with other Raman nanoparticles in order to provide multiplexing of signals.

In an embodiment, the Raman agent can be incorporated (e.g., disposed inside and/or attached to the surface of) or encapsulated into a biological agent (e.g., a cell or a virus). In particular, the Raman agent can be incorporated into stem cells, t-cells, bacterial strains, Red blood cells, white blood cells, and the like. As the encapsulating virus, bacteria, or stem cell moves through the body or within an area, the Raman imaging system can be used to monitor/track the virus, bacteria, or cell. Studying cell motility and tracking its natural distribution in the body is an important biological process that can offer scientists important information on how to better design diagnostics and therapeutics. By encapsulating a stem cell, for instance, with a Raman agent (e.g. Raman active dyes or Raman nanoparticles) one could use the Raman signal to monitor its localization within the body after it has been administered for therapy for instance. One could also study the homing effects that bacteria, viruses, t-cells, or even macrophages have on tumor sites if these cells were to be previously encapsulated with Raman agents (e.g. Raman dyes or Raman nanoparticles). One could essentially use their Raman active signal as a reporter to track where exactly these cellular entities have localized after administration.

In an embodiment, the method of monitoring biological agent includes introducing a first type of biological agent that includes a first type of Raman agent to a sample or a subject. After an appropriate amount of time, a Raman imaging device can be positioned adjacent an area that may include the biological agent. Subsequently, the area is exposed to a light beam, where if the biological agent including a Raman agent is present, the light beam is scattered. The light beam that is scattered is referred to as a Raman scattered light energy. The Raman scattered light can be detected using the Raman imaging device. The detection of the Raman scattered light indicates that the biological agent is present in the area. If multiple biological agents or types of biological agents are introduced, each can include the same type of Raman agent or different types of Raman agents. If different type of Raman agents are used, then the type and/or amount of the biological agent can be determined based on the type of Raman agent detected.

In an embodiment, the Raman compounds can include a reporter compound as noted above conjugated to a targeting ligand, so that the Raman agent or compound can have an affinity for a targeting ligand.

In an embodiment, the Raman agent can include a targeting ligand that is a chemical or biological ligand or compound having an affinity for one or more targets (e.g., also referred to as a "specific target" or "targeted area"). In an embodiment, the targeting ligand can include, but is not limited to, a drug, a therapeutic agent, a radiological agent, a chemological agent, a small molecule drug, a biological agent (e.g., antibodies, peptides, proteins, apatamers, antigens, and the like) and combinations thereof, that has an affinity for a target or a related biological event corresponding to the target. It should be noted that Raman agent modified with conjugation to other molecules (e.g., antibodies, proteins, peptides, apatamers, small molecules, and the like) in order to target the Raman agent to a particular molecular target are intended to be covered by embodiments of the present disclosure. For example, a Raman agent can be modified with a peptide so that it can target new blood vessels in tumors or a chemical associated with a specific cancer, tumor, or precancerous tissue. In an embodiment, the targeting ligand can have an affinity for a target such as cancer, tumor, precancerous cells or tissue, atherosclerosis, fibrosis. In another embodiment, the targeting ligand can be used for trafficking (where the Raman agent is incorporated into viruses or cells (e.g., stem cells, t-cells, Red blood cells, white blood cells, and the like)) to look at distribution in the body.

Embodiments of the present disclosure include methods of using a Raman imaging device (e.g., Raman endoscope probe) in conjunction with Raman agents to image, detect, study, monitor, evaluate, and/or screen a subject (e.g., whole-body or a portion thereof (e.g., bronchioles, esophagus, colon, rectum, skin, oral mucosa, intraoperatively any organ, and the like)). The Raman agents are administered to the subject and then the subject (e.g., a portion such as the colon and the like) can be imaged using an endoscope including a Raman imaging device. The Raman imaging device in conjunction with an analysis system (e.g., computer, software, etc, are interfaced with the Raman imaging device) is capable of creating an image of a living host, which is in contrast to just measuring a signal in a host. In an embodiment, the Raman imaging system can just be used to measure a signal.

The following describes an embodiment using a Raman endoscope probe and a subject is administered one or more Raman agents. An endoscope including the Raman endoscope probe is introduced to the subject (e.g., endoscopically, laproscopically, intraoperatively, or surgically). The introduction can be via an orifice or through a surgical incision. The endoscope including the Raman endoscope probe can be moved to scan an area or if the specific target area is known, the endoscope can be moved adjacent the specific target area. Depending on the type of Raman endoscope probe (e.g., forward view or side view), the position of the endoscope can be varied to obtain the optimum scattered light energy from the Raman agent(s). The Raman endoscope can be used to scan an area and/or map an area in the subject.

A Raman image (e.g., the Raman scattered light energy) using embodiments of the present disclosure is different from a bulk signal in that the Raman image is a visual representation of signal as a function of location (e.g., a particular location in the host such as a part (e.g., a few millimeters, a centimeter or more) of the colon or the like).

Embodiments of the present disclosure can be used to map an area. The area can include a portion or the entire area of the: cervix, bladder, bronchioles, esophagus, stomach, colon, rectum, skin, oral mucosa, and intraoperatively or laparoscopically an organ. In an embodiment, the mapping can be conducted by exposing the area to the Raman imaging device by moving the Raman imaging device. An area can be mapped prior to and/or after introducing one or more types of Raman agents and/or one or more types of biological agents to the subject or sample. The Raman imaging device detects the Raman scattered light and this can be correlated to a position in the area so that a map can be obtained for the area. In an embodiment, the area can be monitored as a function of time and can be used to determine the impact of a particular treatment or the like.

Embodiments of the present disclosure include administering or otherwise introducing one or more types of Raman agents (e.g., have emissions at different wavelengths, or two different types of Raman agents) to a subject. In embodiments including two or more different types of Raman agents, each of the Raman agents has a different Raman signature and/or can be directed to different targets. Subsequently, the subject can be imaged using a Raman endoscope probe via the introduction of an endoscope to the subject. In an embodiment, the different Raman agents used in conjunction with the Raman endoscope probe could be used to image different portions (e.g., tissue, cells, organs, and the like) of the subject and/or detect different types of targets.

In another embodiment, each of the different Raman agents could be directed to different biological targets relating to the same disease, condition, or related biological event. In this embodiment, the different types of Raman agents could be used to determine the presence or absence of one or more features of the disease, condition, or related biological event, which is useful for certain cancers and their progression over time and even after treatment to look at their response to therapy (e.g., the type or severity of a cancer can be determined by the presence of one or two targets, and treatment is based on the type or severity of the cancer). Embodiments of the present disclosure include other ways in which a combination of Raman agents could be used in embodiments of the present disclosure.

In another embodiment of the present disclosure, the Raman endoscope probe and the Raman agents can be combined with an anatomical image and/or a functional image of the same subject generated from an anatomical imaging system. The anatomical imaging system can include, but is not limited to, bright field white light imaging, computer topography (CT), ultrasound, magnetic resonance imaging (MRI), and the like. The combination of multiple functional images or a functional image with an anatomical image would provide more useful information about the exact location of a specific molecular event. The anatomy would tell where, and the molecular image (functional image) would tell how much molecular signal from a given anatomical coordinate.

In each of the embodiments described above and herein, one or more types of untargeted Raman agents can be used in addition to the targeted Raman agent(s). The use of the untargeted Raman agents allows for an assessment of the ratio between or among specific binding to non-specific binding Raman agents, and thus providing a ratiometric estimate of truly bound Raman agent(s). The untargeted Raman agents can be used to compare areas where the targeted Raman agents are located (e.g., the targeted area or specific target) to the areas where the targeted Raman agents are not located. The use of the untargeted areas can provide a baseline that can be used in the analysis, evaluation, and/or mapping of an area or targeted area.

It should be noted that the amount effective to result in uptake of a Raman agent into the cells or tissue of the subject depends upon a variety of factors, including for example, the age, body weight, general health, sex, and diet of the host; the time of administration; the route of administration; the rate of excretion of the specific compound employed; the duration of the treatment; the existence of other drugs used in combination or coincidental with the specific composition employed; and like factors well known in the medical arts.

Embodiments of the present disclosure can also be used to identify the surgical margins for a tumor resection. In particular, a surgeon can use the imaging information provided by embodiments of the present disclosure to guide surgery. Embodiments of the present disclosure can be used in-situ morphological mapping, in particular, to map cancer tissue to guide therapy. Embodiments of the present disclosure can be used to develop an understanding of the morphological composition of a tumor at the molecular level and optimize their therapies accordingly. Embodiments of the present disclosure can also be used targeted thermal ablation. The therapy could take advantage of the energy-absorbing properties and the targeting properties of the nanoparticles to thermally ablate tumor cells.

Kits

The present disclosure also provides packaged pharmaceutical compositions comprising a pharmaceutically acceptable carrier and one or more Raman agents and a Raman imaging device such as a Raman endoscope probe or handheld Raman device. Other packaged pharmaceutical compositions provided by the present disclosure further include indicia including at least one of: instructions for using the Raman imaging device and the Raman agent to image a subject.

This disclosure encompasses kits that include, but are not limited to Raman agents and a Raman imaging device and directions (written instructions for their use). The Raman agent can be tailored to the particular biological event to be monitored as described herein. The kit can further include appropriate buffers and reagents known in the art for administering the Raman agent to the subject. The Raman agent and carrier may be provided in solution or in lyophilized form. When Raman agent and carrier of the kit are in lyophilized form, the kit may optionally contain a sterile and physiologically acceptable reconstitution medium such as water, saline, buffered saline, and the like.

EXAMPLES

Now having described the embodiments of the present disclosure, in general, example 1 describes some additional embodiments of the present disclosure. While embodiments of the present disclosure are described in connection with example 1 and the corresponding text and figures, there is no intent to limit embodiments of the present disclosure to these descriptions. On the contrary, the intent is to cover all alternatives, modifications, and equivalents included within the spirit and scope of embodiments of the present disclosure.

Example 1

Administration of targeted surface-enhanced Raman scattering (SERS) nanoparticles can be performed, followed by rinse- and suction-removal of unbound SERS nanoparticles if necessary. The image resolution of the Raman endoscope probe, for example, could be about 1 mm, which corresponds to the spot size of the collimated illumination beam (at about 785 nm). The Raman endoscope probe can perform spectral acquisitions of the area of interest and Raman signals from SERS nanoparticles, which can be dispersed through a spectrometer and imaged onto a sensitive CCD. Due to the unique fingerprint and narrow spectral composition associated with different SERS nanoparticles, multiplexing several targets simultaneously is possible. Software de-multiplexing can allow for the simultaneous visualization of multiple SERS nanoparticles that each targets a specific disease biomarker (see FIG. 1). Assessment of non-specific binding can also be evaluated by multiplexing by using targeted vs. non-targeted SERS nanoparticles (each containing a different spectral fingerprint) and administering them together to evaluate true binding events. One useful feature of the Raman imaging device would be that it is designed to image at a range of working distances. While signal intensities may vary as a function of working distance, relative signal intensities between various SERS tags will reveal the relative expression level of various biomarker targets.

As mentioned briefly above, FIG. 1.1 describes a number of types of SERS nanoparticles (upper left schematic) where each unique SERS reporter can be interchanged and each produce a unique Raman spectral signature, as shown for example by the bottom three spectra. If the SERS nanoparticles are multiplexed into the colon, the Raman endoscope probe can obtain spectra corresponding to the sum of all types of SERS nanoparticles. Software processing is used to de-multiplex the combined spectra (top spectrum) into the component spectra (below). The relative concentration of each type of SERS nanoparticle may then be quantified.

Another useful feature of the Raman imaging device would be for it to have mapping capabilities where a series of spectra could be acquired in two or even three dimensional space by using for example: mirrors and rotational components for spatial 2D imaging, and perhaps utilizing spatial offsetting to acquire depth information for 3D imaging. These additional components could move the light source/collection source to preset areas of interest in order to acquire a true image.

Example 2

Introduction

The clinical translation of Raman spectroscopy has been hindered by the inherently weak nature of the Raman effect. Raman active silica-gold nanoparticles (R—Si—Au—NPs; FIG. 2.1) overcome this limitation by producing high Raman signals via Surface Enhanced Raman Scattering[1]. Targeted polyethylene glycol (PEG)-ylated R—Si—Au—NPs are being designed to detect colorectal cancer after administration into the bowel lumen. With this approach, PEG-R—Si—Au—NPs are not expected to enter the systemic circulation and would be removed from the body via defecation. We examined the acute toxicity and biodistribution of PEG-R—Si—Au—NPs after different routes of administration in mice. Here we show that after intravenous administration (IV), PEG-R—Si—Au—NPs are removed from the circulation by the reticuloendothelial system. By 24 hours, PEG-R—Si—Au—NPs elicit a mild inflammatory response and an increase in oxidative stress in the liver which subsides by 2 weeks. No evidence of significant toxicity was observed using clinical, histological, biochemical or cardiovascular parameters over 2 weeks. Notably, after administration per rectum (PR), no significant bowel or systemic toxicity is observed and no PEG-R—Si—Au—NPs are detected systemically. Although additional studies are required to investigate the long-term effects of PEG-R—Si—Au—NPs, these initial results support their safe use in living subjects, especially when administered rectally.

Negligible toxicity is observed with the exposure of in vitro cultured human cells to PEG-R—Si—Au—NPs at low concentrations. Only at very high concentrations and prolonged exposure conditions, minimal amounts of cytotoxic and oxidative stress responses are observed in vitro. The health effects of PEG-R—Si—Au—NPs in living subjects remain unknown since little is understood about how the body reacts to nanoscale synthetic materials, especially in regards to their mode of uptake, biodistribution, intracellular trafficking, processing and fate. Furthermore, it is now becoming clear that the route of administration plays a crucial role in determining the outcome of nanoparticle toxicity. For example, modified single walled carbon nanotubes are extremely toxic when administered via the intratracheal route[2,3], causing dose-dependent inflammation and small nodule formation, but, show no significant toxicity when given intravenously[4]. Studies have also shown that macrophages residing within the reticuloendothelial system, in particular the liver, are highly efficient at removing nanoparticles from the systemic circulation thereby minimizing their potential to cause toxicity[5,6]. For these reasons, PEG-R—Si—Au—NPs are being initially designed by our group to target colon cancer in the hope that they will not significantly cross the bowel-wall when administered rectally. However, if they manage to enter the systemic circulation, they would primarily be directed to the liver by the portal venous system where they would be entrapped. Hence, in the present study, we have examined whether intrarectally administered PEG-R—Si—Au—NPs would cause any toxicity to the bowel and whether these nanoparticles would cross the bowel-wall. We have also examined the biodistribution and acute systemic effects of these nanoparticles after direct administration into the circulation via the IV route.

In this study R—Si—Au—NPs were PEGylated, but not further functionalized (e.g. using targeting peptides), in order to study the core nanoparticle which will likely be used in many future medical applications (FIG. 2.1). The dose of PEG-R—Si—Au—NPs ($9.6 \times 10^{10}$ nanoparticles in 200 µl of saline) administered to mice in both the IV and PR experiments is a 1,000-fold higher dose than the minimum dose that can be currently detected in vivo using a Raman microscope[1]. This dose was deemed to be large enough to assess any potential toxicity that PEG-R—Si—Au—NPs may cause in living subjects, and yet not so low that it could not be eventually imaged in clinical applications. Furthermore, 200 µl of either saline (for control animals) or PEG-R—Si—Au—NPs was thought to be a small enough volume of fluid to have minimal impact on the animal's cardiovascular system. Male and female FVB mice were chosen to assess the response to PEG-R—Si—Au—NPs within an animal model with a fully competent immune system.

Male (n=60) and female (n=60) mice were followed daily for 2 weeks after either IV or PR PEG-R—Si—Au—NP administration. During this time, there were no deaths and no effect was observed on the physical appearance (fur, eyes, mucous membranes, secretions, stool, gait, posture, breathing pattern), behavior (gait, posture, stereotypes, vocalizations) or social interactions of all mice. In addition, no ECG (FIG. 2.8), blood pressure or heart rate (FIG. 2.12) changes occurred following either IV or PR PEG-R—Si—Au—NP administration. All mice receiving PEG-R—Si—Au—NPs demonstrated similar increases in body weight over 2 weeks compared to control mice, with female mice being slightly lighter than their male counterparts at the start of the study (FIG. 2.12). In both sexes, plasma biochemical and hematological indices remained within their respective normal ranges following IV and PR PEG-R—Si—Au—NP administration (FIG. 2.13). These results suggest that PEG-R—Si—Au—NPs have no acute effect on basal cardiovascular function or hematological parameters for either of the two routes of administration studied in mice.

Detailed necropsy by a mouse pathologist did not reveal any gross organ abnormality in any of the animals studied. As the nanoparticle core is made from gold (FIG. 2.1), its biodistribution can be determined by measuring the concentration of gold within tissue samples. All samples were digested with hydrofluoric acid to dissolve the outer silica shell of the PEG-R—Si—Au—NP, thereby freeing the elemental gold core for measurement by inductively coupled plasma-mass spectrometry (ICP-MS)[7]. After IV PEG-R—Si—Au—NP administration, gold was detected in the blood of only one female and two male animals at 5 min post injection. No gold was detected in blood samples at later time points but significant concentrations of gold were found in the liver and spleen from all animals (FIG. 2.2), suggesting that the reticuloendothelial system (RES) was able to effectively and efficiently remove PEG-R—Si—Au—NPs from the systemic circulation. Histological analysis of liver samples after IV PEG-R—Si—Au—NP administration support the ICP-MS data and demonstrate uniform, very fine (<1 micron diameter), black, extracellular pigment within the peri-sinusoidal space (space of Disse) in both male and female mice (FIGS. 2.3, 2.7 and 2.13). This pigment did not histochemically react with the Prussian blue methods, or the Fontana-Masson method, respectively implying that the pigment was not ferrous-based or melanin based (data not shown). Coupled with its uniformly fine diameter and its extracellular location, the pigment was therefore thought to represent the PEG-R—Si—Au—NPs. After 2 hours, similar pigment was also seen intracellularly within resident macrophages of the liver. As the amount of pigment within macrophages increased over 24 hours, less was observed in the sinusoids, suggesting that PEG-R—Si—Au—NPs were being extracted by the macrophages. By 2 weeks, pigment was only observed within the macrophages, with none present within the liver sinusoids (FIGS. 23, 2.7, and 2.9). Immuohistochemical analysis of liver and spleen samples was therefore undertaken to verify the co-localization of PEG-R—Si—Au—NPs with macrophages. However despite two separate attempts by independent laboratories, control and experimental tissues did not react with the monoclonal antibody against the F4/80 macrophage specific antigen. The failure of the F4/80 antibody to immunoreact with the macrophages in the tissues of our control and experimental mice could be due to significant alterations in the epitope structure of the F4/80 macrophage antigen (e.g., inappropriate fixation or inherent differences in the F4/80 epitope in this group of mice), incorrect methodology (e.g., not following manufacturer's instructions), or issues with the antibody used itself (e.g., incorrect generation of the appropriate antibody, incorrect storage/transport of the antibody). However, we feel that incorrect methodology is unlikely since manufacturer's instructions were followed originally (with subsequent attempts to make the antibody "work" deviating from manufacturer's instructions based on the laboratory's experience). Transmission electron microscopy (TEM) of liver samples was also performed to further evaluate the intracellular location of PEG-R—Si—Au—NPs within liver samples following IV administration. The results demonstrate the presence of PEG-R—Si—Au—NPs within macrophages at each time point of interest. After 5 minutes, majority of PEG-R—Si—Au—NPs were seen within the peri-sinusoidal space with only a small number located within the vesicles of resident macrophages located adjacent to the sinusoids. By 2 hours, the number of nanoparticles internalized by resident macrophages had increased, and by 24 hours, TEM demonstrated large numbers of PEG-R—Si—Au—NPs within the vesicles of macrophages with no PEG-R—Si—Au—NPs detected within the peri-sinusoidal space. Since PEG-R—Si—Au—NPs were mainly located within the sinusoids at the early time points, and not trapped by cellular material, it is possible that there may have been some PEG-R—Si—Au—NP loss during the sample preparation for TEM analysis at these times (FIGS. 2.3 and 2.9). Histological assessment of the spleen for the presence and amount of PEG-R—Si—Au—NPs was inconclusive, primarily due to the presence of the iron-containing hemosiderin pigment found within splenic macrophages (hemosiderophages). In all mice in this study, there was a moderate amount of splenic hemosiderophages, most likely representing normal physiologic extramedullary hematopoiesis in murine spleens. However, the amount and appearance of the hemosiderin (dense, goldern-brown, variably-sized, coarse intracytoplasmic pigment granules on H&E) appeared to greatly overwhelm the inherent very fine, black, granular appearance of the PEG-R—Si—Au—NPs on H&E sections. Prussian-blue staining did not alleviate this problem, since the intense dark blue nature of the positive-staining hemosiderin also overwhelmed inherent very fine, black, granular appearance of the PEG-R—Si—Au—NPs (data not shown).

Although PEGylation of nanoparticles increases their bioavailability by reducing their interaction and uptake by macrophages[5], our results show that PEG-R—Si—Au—NPs with a 5:1 ratio of Mal-PEG$_{2000}$-OME to Mal-PEG$_{5000}$-NHS are still efficiently taken up by the RES. This would be ideal for PEG-R—Si—Au—NPs applied into the bowel lumen, since any nanoparticles that do manage to enter the systemic circulation will be rapidly removed by the RES thereby limiting the potential for them to cause toxicity. Future alternative clinical applications which may require IV administration of PEG-R—Si—Au—NPs will therefore require a different PEG ratio tailored to prolong their bioavailability.

Despite there being no pigment within hepatocytes at any time after IV PEG-R—Si—Au—NP administration, a mild degree of hepatocyte apoptosis was seen in all animals after 24-hours post injection (FIGS. 2.3, 2.7, and 2.9). Interestingly, this also coincided with the time when the most pigment, and thus PEG-R—Si—Au—NPs, was seen in macrophages. We therefore hypothesize and offer indirect support for a potential mechanism by which macrophages can signal neighboring hepatocytes to undergo apoptosis. As PEG-R—Si—Au—NPs are known to cause an increase in free radical formation, one possibility is that they induce an increase in cellular oxidative stress within hepatocytes and macrophages. Our data support this and show an increase in the gene-expression of phase-2 antioxidant enzymes within the liver. Despite an early increase in glutathione peroxidase and hemoxygenase transcription (FIG. 2.4), the initial antioxidant defenses were probably overwhelmed since hepatocytes still increased their Bax:Bcl-2 ratio, which is known to cause activation of cellular pro-apoptotic mechanisms[8]. As a result, expression of inflammatory (TNF-α and IL-6) and apoptotic (caspase) genes was increased by 24 hours (FIG. 2.5), which resulted in hepatocyte apoptosis, as seen histologically and confirmed by TUNEL assay (FIGS. 2.3. 2.7, and 2.14). However, no apoptosis was seen by 1 week post injection, which can be explained by an increase in gene expression of catalase and superoxide dismutase (FIG. 2.4), both of which have been shown to inhibit apoptosis by removing superoxide free radicals and hydrogen peroxide respectively[9]. Taken together, these results suggest the liver initiates a well-controlled apoptotic response to PEG-R—Si—Au—NPs in the acute phase after exposure. Given the regenerative capacity of the liver and its role as a "filter" within the RES, this acute phase response seems intuitive if the liver is to eliminate foreign material that it extracts from the circulation in a controlled and regulated manner.

Examination of the bone marrow, colon, small intestine, kidney, lung, brain, gonads and feces with ICP-MS demonstrated no detectable gold after IV PEG-R—Si—Au—NP administration in all mice at all times after injection. Histological examination of these organs, as well as the pancreas, kidney and heart also revealed no PEG-R—Si—Au—NPs or any signs of toxicity.

After PR PEG-R—Si—Au—NP administration, gold was detected in the feces of both male and female mice at 5 min after exposure. Histological analysis confirmed these findings demonstrating a large amount of pigment within the colon lumen of all animals as early as 5 min after exposure, with no pigment seen in the bowel by 2 hours. Furthermore, no pigment was seen at any time point within the enterocytes of the bowel-wall after PR PEG-R—Si—Au—NP administration. A single female mouse demonstrated a trace concentration of gold within the blood at 5 min and 2 hours after exposure. However, this was probably owing to a slightly traumatic colonic catheterization in this animal that could have resulted in a small breach in the integrity of the colonic epithelium thereby allowing PEG-R—Si—Au—NPs to enter the circulation. Another possibility may have been increased absorption of nanoparticles by colonic macrophages within the gut-associated lymphoid tissue in this animal. Despite this, no gold or pigmentation was detected in any other organ either by ICP-MS or histological analysis. In particular, liver tissue from all animals revealed no pigment within the sinusoids, macrophages or hepatocytes at all times examined after administration, which was also confirmed by TEM (FIGS. 2.6, 2.7 and 2.14). Taken together, these results suggest that non-targeted PEG-R—Si—Au—NPs remain in the bowel lumen, do not cross the bowel-wall, and are effectively eliminated from animals by defecation.

Although long-term studies are still necessary to examine the fate of PEG-R—Si—Au—NPs in the body, our encouraging results so far support the use of this nanoparticle as a molecular imaging probe with potential translation into clinical practice. Currently, we are testing PEG-R—Si—Au—NPs that have been functionalized with ligands to detect molecular markers up-regulated in human dysplastic colonic lesions[10]. Further studies will be necessary to examine if functionalized nanoparticles are processed differently, especially since recent studies have shown that functionalized or coupled nanoparticles are taken up by colon cancer cells significantly more readily when compared to uncoupled nanoparticles[11]. The objective of our future studies is to apply targeted PEG-R—Si—Au—NPs locally within the bowel lumen to detect early colon cancer with a uniquely designed Raman colonoscope. This will have the potential to provide clinicians with a powerful biologically driven imaging technique and an accompanying specifically designed device to detect early colon cancer, including flat lesions[12], in real time.

Methods

Animals

All animal experiments were conducted in compliance with the relevant guidelines and regulations approved by the Stanford Administrative Panel on Laboratory Animal Care (APLAC). A total of one hundred and twenty (120) 5 week-old male and female FVB mice were obtained from a pathogen-free colony (Charles Rivers Laboratory). FVB mice were chosen in order to assess the response to nanoparticles within an immunocompetent animal model. Mice were housed in same-sex groups with three animals per cage. Water and food were available to all mice ad libitum. The environmental conditions were carefully monitored and maintained within an acceptable range throughout the study (temperature 66±2° F.; relative humidity 39±1%; 12-h light/dark cycle). All animals were quarantined for 7-days prior to the commencement of any experimental studies.

Nanoparticle Characteristics

The R—Si—Au—NPs were obtained from Oxonica Materials Inc (Mountain View, Calif.) and consisted of a 60 nm gold nanocore, a Raman-active organic molecule and a 30 nm silica shell, making the entire nanoparticle on the order of 120 nm in diameter (FIG. 2.1). This arrangement dramatically increases the incident electromagnetic field of the Raman active organic molecule, thereby significantly amplifying its Raman signal intensity. Recent studies by our group have shown that these R—Si—Au—NPs have ultra-high picomolar sensitivity in vivo[1]. In addition, as the bound Raman active organic molecule can be altered between different nanoparticles, different R—Si—Au—NPs are therefore able to provide different spectral signatures. Accordingly, we have shown the ability of Raman spectroscopy to separate the spectral signature of at least 5 different R—Si—Au—NPs in a living mouse following IV injection[13]. The particular lot used in this study was the 5440 batch which consists of a unique Raman active, material layer (Trans-1,2-Bis(4-pyridyl)-ethylene) and its associated spectrum which is detailed in previous work[1]. Two different sized PEG molecules, Mal-PEG$_{2000}$-OME and Mal-PEG$_{5000}$-NHS, were added to the surface of the R—Si—Au—NP in a 5:1 ratio, respectively. The smaller Mal-PEG$_{2000}$-OME was added to improve nanoparticle biocompatibility while the larger Mal-PEG$_{5000}$-NHS was added to provide a functional group for potential ligand attachment. Both surface-PEG chains were added to the surface of these nanoparticles in a two-step process. Initially, thiol groups were introduced into the silica shell of the nanoparticle using 3-mercaptopropyltrimethoxysilane. This was followed by conjugation with malemide activated mPEGs, where the malemide group reacted with the thiol group on the nanoparticle surface at neutral pH. In order to ensure consistency between the experiments, all PEG-R—Si—Au—NPs were created at the same time from the same batch of stock nanoparticles received from Oxonica Materials Inc. All nanoparticles were stored at 4° C. between experiments.

Experimental Protocol

To assess the effect of IV and PR R—Si—Au—NP administration, mice were randomly allocated into two experimental groups each containing sixty mice with an equal male-to-female sex ratio (FIG. 2.11). In the IV group, three male and three female mice for each time point were given a 200 µl IV injection (via the tail vein) of either sterile saline or PEG-R—Si—Au—NPs. Mice in the PR group were fasted overnight in special metabolic cages with wire floors which allowed any feces produced to drop into a waste container. This prevented mice from having access to their feces during the fasting period thereby ensuring their large bowel was completely evacuated and prepared prior to any PEG-R—Si—Au—NP administration. The following day, three male and three female mice for each time point were given a 200 µl PR injection of either sterile saline or PEG-R—Si—Au—NPs using a 24-gauge angiocatheter. All mice were euthanized by carbon dioxide asphyxiation at specific time points: 5 min, 2 hours, 24 hours, 1 week and 2 weeks post PEG-R—Si—Au—NP administration (FIG. 2.11).

Mice which were euthanized at 2 weeks post PEG-R—Si—Au—NP administration were carefully monitored throughout the study. For each mouse, their physical appearance (fur, eyes, mucous membranes, secretions, stool, gait, posture, breathing pattern), behavior (gait, posture, stereotypes, vocalizations) and interactions towards other animals were assessed and recorded daily. The body weight and cardiovascular status (ECG measurements using subcutaneous electrodes and blood pressure and heart rate measurements using a tail vein cuff device (Coda 6, Kent Scientific Corporation)) for each mouse were also recorded weekly. In addition, 200 µl of blood was collected from each mouse via retro-orbital bleeding through a heparin coated glass tube 1 week prior to PEG-R—Si—Au—NP administration to determine the baseline complete blood count (CBC), chemistry and electrolyte panels (Veterinary Service Centre of the Department of Comparative Medicine at Stanford University). Since APLAC protocol restricted subsequent blood withdrawal to <200 µl for each animal, only CBC and chemistry panels were determined at the beginning of the second week following PEG-R—Si—Au—NP administration. Blood samples for electrolytes were subsequently taken at the end of the second week immediately after euthanasia via cardiopuncture. However, it was not possible to analyze chemistry panels from samples collected via cardiopuncture due to the well described phenomenon of muscle tissue contamination encountered with this particular blood collection procedure[14]. Prior to any blood sample collection all mice were fasted overnight.

Pathologic Evaluation

A complete post mortem examination was performed on each mouse at all time points, and examined for gross changes. Samples of all major organs and tissues were collected and fixed in neutral-buffered 10% formalin for 48 hours. Fixed samples of liver, spleen, colon, small intestine, heart, kidneys, lungs, brain, and gonads were then routinely processed and stained with hematoxylin and eosin (H&E; Histotec Laboratories, Hayward, Calif.) for light microscopy. Histopathological examination was performed by a veterinary pathologist blinded to other findings. Histopathologic diagnosis was performed according to the Standardized System of Nomenclature and Diagnostic Criteria (SSNDC).

Immunohistochemistry

To assess the co-localization of PEG-R—Si—Au—NPs and macrophages, paraffin-embedded, formalin-fixed liver and spleen tissues from a representative male and female administered with PEG-R—Si—Au—NP from each time point were chosen and immunostained with a rat anti-mouse purified monoclonal antibody against the F4/80 macrophage specific membrane antigen (AbD Serotec). Tissues were cut 4 mm thick by a microtome and stained using a StreptAvidin-HRP immunoperoxidase method. Endogenous peroxidase activity was inhibited by 3% hydrogen peroxide for 10 min followed by enzyme digestion in trypsin for 15 min at room temperature. Sections were then incubated for 2 hours with the primary F4/80 antibody. A saline treated animal was used as a positive control and an animal which had both received PEG-R—Si—Au—NPs and been incubated without the primary antibody was used as a negative control. After three washes with PBS for 5 min each, the sections were incubated for 30 min with a goat-anti rat-biotinylated secondary antibody for 30 min. StreptAvidin-HRP was applied for 30 min and reacted with diaminobenzidine hydrochloride and counterstained with hematoxylin. Immunostained sections were then evaluated by a veterinary pathologist.

TUNEL Assay

To assess the co-localization of PEG-R—Si—Au—NPs and apoptoic cells, paraffin-embedded, formalin-fixed liver and spleen tissues from a representative male and female animal from each time point which had received PEG-R—Si—Au—NPs were chosen and stained with an in situ terminal deoxynucleotidyl transferase-mediated dUTP nick end-labeling (TUNEL) kit (Millipore), following the manufacturer's protocol for paraffin sections. Using a light microscope, the number of positively stained cells per 100 cells was counted by a veterinary pathologist.

Transmission Electron Microscopy

During gross pathologic examination, samples of liver, spleen, colon, small intestine, kidneys, lungs, brain and gonads (measuring approximately 1 mm$^3$) were collected in a 2:1:1 solution of 0.2 M sodium cacodylate buffer: 10% glutaraldehyde: 8% paraformaldehye (EMSdiasum). Samples were then stored at 4° C. before being stained en bloc with uranyl acetate and embedded in epoxy resin. A representative male and female from each time point that had received PEG-R—Si—Au—NPs were chosen and ultra-thin (60 nm) sections of each organ were cut and examined by transmission electron microscopy (TEM) in order to determine the intracellular location of PEG-R—Si—Au—NPs.

Inductively Coupled Plasma-mass Spectrometry

During gross pathologic examination, samples of liver, spleen, colon, small intestine, kidneys, lungs, brain and gonads (measuring approximately 1 mm$^3$) were collected to determine concentrations of gold in each of these tissues by ICP-MS analysis. Samples were prepared by microwave-assisted acid digestion using a mixture of trace metal grade 70% nitric acid (HNO$_3$; Fisher Sci), 37% hydrochloric acid (HCl; Fisher Sci), and 48% hydrofluoric acid (HF; Fisher Sci). Samples were then air-dried and re-suspended in 5× dilution aqua regia. ICP-MS was undertaken using a JA IRIS Advantage/1000 Radial ICAP Spectrometer which was calibrated using a 2 ppm [Au] high standard and a 1 ppm [Au] QC standard in dilute aqua regia matrix. The reproducibility of the spectrometer was determined by measuring a series of different [Au] standards in triplicate: 1.0 ppm [Au] was measured to an accuracy of 0.9869±0.0058, 0.1 ppm [Au] was measured to an accuracy of 0.0012±0.0014, 0.01 ppm [Au] was measured to an accuracy of 0.0103±0.0010.

Assessment of antioxidant enzyme and inflammatory gene expression using q-RT-PCR During gross pathologic examination, a sample of liver was collected and stored at −80° C. The change in gene expression in liver samples from animals which had been administered IV PEG-R—Si—Au—NPs were evaluated and compared with control animals which had received IV saline according to methods described previously[15]. Total ribonucleic acid (RNA) was extracted from sonicated liver tissue using RNeasy Plus Mini Kit (Qiagen) which contained gDNA eliminator spin columns to effectively remove genomic DNA. The RNA concentration in each sample was then calculated using the Qbit system (Invitrogen). Using 1 µg of RNA, cDNA was synthesized using reverse transcription (RT) by incubating samples at 25° C. for 5 min followed by 42° C. for 45 min with qScript cDNA Supermix (Quanta Biosciences) which contained buffer, dNTPs, MgCl$_2$, random primers, RNase inhibitor and Reverse Transcriptase. Quantitative reverse transcription polymerase chain reaction (q-RT-PCR) was then undertaken using the Realplex Mastercycler machine (Eppendorf) with PerfeCTa SYBR Green FastMix which contained AccuFast Taq DNA polymerase (Quanta Biosciences). All samples were run in triplicate in a 20 µL reaction volume using cDNA of 100 ng RNA equivalent with an initial pre-heating phase of 95° C. for 2 min followed by 60 cycles consisting of 95° C. for 30 sec, 55° C. for 30 sec and 68° C. for 30 sec. Melting curve analysis was performed for each reaction to exclude non-specific PCR side products. The primer sequences for antioxidant enzyme genes (catalase, superoxide dismutase, haemoxygenase and glutathione peroxidase) and inflammatory genes (Bax, Bcl-2, Capase-3, IL-6 and TNF-α) along with the internal control (β-actin) are shown in FIG. 2.15. As the RNA extraction for some liver samples did not generate sufficient quantities of RNA to run q-RT-PCR, male and female samples for the PEG-R—Si—Au—NP and control groups were analyzed together at each time point. Statistical analysis using a two-way RM ANOVA was therefore performed comparing the effect of time (5 min, 2 hours, 24 hours, 1 week and 2 weeks) and treatment (saline vs. intravenous or per rectum).

Statistical Analysis

All quantitative variables are expressed as mean±standard eror of the mean (S.E.M). When possible, a three-way RM ANOVA was performed comparing the effect of time (5 min, 2 hours, 24 hours, 1 week and 2 weeks), treatment (saline vs. intravenous vs. per rectum) and sex (male vs. female). Where a significant effect of time, group or sex was indicated, the post hoc Student-Newman-Keuls test was used to isolate the statistical differences. For all comparisons, statistical significance was accepted when $P<0.05$.

Additional Discussions

As the concentration of gold, as determined by ICP-MS, within the liver following IV administration slowly declined after 2 weeks, it suggests that some PEG-R—Si—Au—NPs are probably being removed from the animal via heptobillary excretion. However, as PEG-R—AuNPs do not cross the bowel-wall and are not absorbed by intestinal cells, the only way to confirm this would have been to collect, separate and analyze all the feces and urine produced by all IV injected mice over the two weeks. Although we did collect samples of feces and, when possible, urine for analysis by ICP-MS, this is only a snapshot representation of a dynamic excretory process and hence it is not surprising that no gold was detected in these samples. Interestingly, there was a peak in gold concentration within the spleen at 24 hours suggesting that up to this time, PEG-R—Si—Au—NPs were still being redistributed within animals. In a single male animal, a small concentration of gold (1.31 ppm/g) was detected in a lung sample at 5 min. In this case, it is likely that the some of the PEG-R—Si—Au—NPs in this animal bypassed the macrophages in the liver and spleen but were subsequently removed from the circulation by macrophages within the lung, which is another organ of the RES.

A mild degree of mitosis was also seen in male and female mice at 24 hours and 1 week following both IV saline and PEG-R—Si—Au—NP administration. This phenomenon has been previously observed and can be attributed to stretch-induced localized proliferation of hepatocytes due to swelling of liver sinusoids following a tail vein injection[16]. The stretching of cells has been shown to increase DNA synthesis and cell proliferation by activating tyrosine kinases and protein kinase C[17]. In addition, the release of other growth factors and stimuli from the neighboring cells which have undergone apoptosis may also contribute to the local mitotic response[16].

References for Example 2, each of which is incorporated herein by reference

1. Keren, S., et al. Noninvasive molecular imaging of small living subjects using Raman spectroscopy. *Proc. Natl. Acad. Sci. USA.* 105, 5844-5849 (2008).
2. Shvedova, A. A., et al. Unusual inflammatory and fibrogenic pulmonary responses to single-walled carbon nanotubes in mice. *Am. J. Physiol. Lung Cell Mol. Physiol.* 289, L698-708 (2005).
3. Lam, C. W., James, J. T., McCluskey, R. & Hunter, R. L. Pulmonary toxicity of single-wall carbon nanotubes in mice 7 and 90 days after intratracheal instillation. *Toxicol. Sci.* 77, 126-134 (2004).
4. Schipper, M. L., et al. A pilot toxicology study of single-walled carbon nanotubes in a small sample of mice. *Nat. Nanotechnol.* 3, 216-221 (2008).
5. Schipper, M. L., et al. Particle size, surface coating, and PEGylation influence the biodistribution of quantum dots in living mice. *Small.* 5, 126-134 (2009).
6. Cho, M., et al. The impact of size on tissue distribution and elimination by single intravenous injection of silica nanoparticles. *Toxicol. Lett.* 189, 177-183 (2009).
7. Makishima, A., Tanaka, R. & Nakamura, E. Precise elemental and isotopic analyses in silicate samples employing ICP-MS: application of hydrofluoric acid solution and analytical techniques. *Anal. Sci.* 25, 1181-1187 (2009).

8. Korsmeyer, S. J., Shutter, J. R., Veis, D. J., Merry, D. E. & Oltvai, Z. N. Bcl-2/Bax: a rheostat that regulates an anti-oxidant pathway and cell death. *Semin. Cancer Biol.* 4, 327-332 (1993).
9. Haddad, J. J. Redox and oxidant-mediated regulation of apoptosis signaling pathways: immuno-pharmaco-redox conception of oxidative siege versus cell death commitment. *Int. Immunopharmacol.* 4 , 475-493 (2004):
10. Hsiung, P. L., et al. Detection of colonic dysplasia in vivo using a targeted heptapeptide and confocal microendoscopy. *Nat. Med.* 14, 454-458 (2008).
11. Jain, A. & Jain, S. K. In vitro and cell uptake studies for targeting of ligand anchored nanoparticles for colon tumors. *Eur. J. Pharm. Sci.* 35, 404-416 (2008).
12. Wallace, M. B. & Kiesslich, R. Advances in endoscopic imaging of colorectal neoplasia. *Gastroenterology.* 138, 2140-2150.
13. Zavaleta, C. L., et al. Multiplexed imaging of surface enhanced Raman scattering nanotags in living mice using noninvasive Raman spectroscopy. *Proc. Natl. Acad. Sci. USA.* 106, 13511-13516 (2009).
14. Wallace Hayes, A. *Principles and methods of toxicology*, (New York, 2008).
15. Pfaffl, M. W. A new mathematical model for relative quantification in real-time RT-PCR. *Nucleic Acids Res.* 29, e45 (2001).
16. Budker, V. G., et al. Mechanism of plasmid delivery by hydrodynamic tail vein injection. II. Morphological studies. *J. Gene Med.* 8, 874-888 (2006).
17. Yamamoto, H., Teramoto, H., Uetani, K., Igawa, K. & Shimizu, E. Stretch induces a growth factor in alveolar cells via protein kinase. *Respir. Physiol.* 127, 105-111 (2001).

Example 3

Brief Introduction

Raman spectroscopy continues to prove itself as a powerful non-invasive molecular imaging tool to evaluate nanoparticle delivery in preclinical models. Its pM sensitivity and multiplexing capabilities are unsurpassed. However, its limited depth of light penetration hinders direct clinical translation. Therefore, a more suitable way to harness its attributes in a clinical setting would be to couple Raman spectroscopy with endoscopy. It was recently reported that flat lesions in the colon were five times more likely to contain cancerous tissue than polyps detected by conventional colonoscopy. The use of an accessory Raman endoscope in conjunction with locally administered tumor targeting Raman nanoparticles during a routine colonoscopy could offer a new way to sensitively detect these dysplastic flat lesions. In this study we evaluated the natural biodistribution of gold surface enhanced Raman scattering (SERS) nanoparticles by radiolabeling them with $^{64}$Cu and imaging their localization over time using microPET. Mice were injected either intravenously (IV) or intrarectally (IR) with approximately 100 µCi of $^{64}$Cu-SERS nanoparticles and imaged with microPET at various time points: immediately, 30 m, 2, 5, and 24 h post injection (See FIG. 3.1). Three mice from each group (IV and IR) were sacrificed at 2, 5 and 24 h and their organs were collected, weighed and counted in a gamma counter to determine % injected dose per gram (% ID/g). Quantitative biodistribution data obtained from each organ correlated well with the corresponding microPET images, revealing that mice injected IV had significantly higher uptake (p<0.05) in the liver (5 h=18.9% ID/g) (24 h=4.8% ID/g), as opposed to mice injected IR (5 h=1.27% ID/g) (24 h=0.3% ID/g). Mice injected IR showed localized uptake in the large intestine (5 h=9% ID/g) (24 h=4.3% ID/g) with minimal uptake in other organs. Raman imaging of the excised tissues confirmed the presence of SERS nanoparticles within tissues of interest. These results suggest that topical application of SERS nanoparticles in the colon appears to minimize their systemic distribution, thus avoiding potential toxicity and supporting the clinical translation of Raman spectroscopy as an endoscopic imaging tool.

Introduction

Colon cancer remains one of the deadliest cancers in the world with more than 940,000 cases reported annually worldwide, from which nearly 500,000 people die each year. Although the mortality rate is slowly decreasing, largely due to prevention through routine colonoscopy screening, more sensitive techniques are needed to detect dysplasia, particularly precancerous flat lesions that cannot be detected with conventional white light endoscopy. We have recently developed a new clinical imaging strategy utilizing a customized Raman endoscope in conjunction with locally administered tumor targeting Raman nanoparticles, to be applied during routine colonoscopy. This strategy could offer a new way to sensitively detect and characterize dysplastic flat lesions, which often go undetected within the colon using conventional white light endoscopy. In this study, we evaluated the ability of our surface enhanced Raman scattering (SERS) gold nanoparticles to effectively target fresh human colon cancer tissue after being covalently conjugated with a heptapeptide (VRPMPLQ) sequence previously shown by our group to bind to dysplastic colonocytes in humans.

This Example describes the characterization of a newly developed Raman endoscope. In addition, this Example evaluates the targeting efficiency of our heptapeptide-SERS nanoparticles on human colon cancer tissue.

Methods

The SERS nanoparticles were conjugated with a tumor targeting heptapeptide (FIG. 3.2). Fresh human colon tissue samples, both malignant and normal adjacent tissue (NAT), were provided to us through our university's tissue bank. Tissues sets (malignant and NAT) from each patient (n=4) were analyzed independently. Each of the malignant and NAT samples were cut into two pieces where one was exposed for 10 min to SERS nanoparticles (0.05 nM) conjugated with the tumor targeting (+) heptapeptide sequence and the other SERS nanoparticles (0.05 nM) conjugated with a (−) random heptapeptide sequence (control). The tissue samples were then rinsed with 3% bovine serum albumin (BSA) for a few seconds and mapped luminal side up using our optimized Raman microscope to evaluate binding.

Results

FIG. 3.2a illustrates the conjugation process of our SERS nanoparticles with tumor targeting heptapeptide. FIG. 3.2b illustrates TEM image of a derivatized SERS nanoparticle. Notice the dark 60 nm gold core encapsulated in glass making the total size of the SERS nanoparticle on the order of 120 nm.

FIG. 3.3a illustrates a schematic of our newly developed Raman endoscope. Notice how the Raman component would be inserted through the 6 mm accessory channel of a conventional clinical colonoscope. The endoscope would be comprised of a fiber optic bundle with a single excitation fiber and a bundle of collection fibers for maximum signal collection. Tumor targeted SERS nanoparticles would be locally administered to suspicious polyps and then rinsed with water. Light would then be shined on the polyp to determine specific binding to dysplastic lesions. FIG. 3.3b illustrates the newly developed prototype Raman endoscopic probe for early detection of colorectal cancer.

FIG. 3.4 illustrates the binding efficiency of (+) heptapeptide SERS nanoparticles on tumor vs. normal colon tissue. In particular, FIG. 3.4a illustrates a digital photo of malignant tumor tissue and normal adjacent tissue. FIG. 3.4b illustrates each tissue exposed to (+) heptapeptide SERS nanoparticles for 10 min. FIG. 3.4c illustrates a Raman image of the tissues using our Raman mapping system. FIG. 3.4d illustrates an overlay of Raman intensity map over digital photo of fresh tissue samples. Notice the increased binding of the (+) heptapeptide SERS nanoparticles throughout the entire tumor tissue as opposed to the decreased localized non-specific binding seen in the normal adjacent tissue.

FIG. 3.5 illustrates the targeting efficiency ratios post-processed from Raman images. The left bar depicts the effective binding ratio of the (+) heptapeptide SERS to tumor tissue vs normal tissue. Whereas the right bar depicts the effective binding ratio of (+) SERS to (−) SERS in tumor tissue samples.

Discussion

Our newly developed Raman endoscope was able to detect 10 pM concentrations of SERS particles on colon tissue surface with an integration time of 10 ms (100 spectra/sec). These tests utilized 20 mW of laser radiation with a 1 mm spot size, however we plan to increase the laser illumination power to ~175 mW, therefore, our detection limit should be ~1 pM. Raman imaging revealed a consistent trend where more binding of (+) heptapeptide SERS nanoparticles was seen in malignant versus NAT samples, with an average of 4 times more binding in malignant versus NAT samples of the (+) heptapeptide SERS conjugated nanoparticles ($p=0.04$). Within the malignant tissue samples themselves, there was also 2 times more binding of the (+) heptapeptide SERS nanoparticles versus the (−) random SERS nanoparticles ($p=0.07$).

Conclusion

These results support the idea of using these heptapeptide labeled SERS nanoparticles as tumor targeting beacons for the detection of colon cancer. In addition, these results support the clinical translation of Raman spectroscopy as an endoscopic imaging technique.

Example 4

Brief Introduction

Raman imaging offers unsurpassed sensitivity and multiplexing capabilities. However, its limited depth of light penetration makes direct clinical translation challenging. Therefore, a more suitable way to harness its attributes in a clinical setting would be to couple Raman spectroscopy with endoscopy. The use of an accessory Raman endoscope in conjunction with topically administered tumor targeting Raman nanoparticles during a routine colonoscopy could offer a new way to sensitively detect dysplastic lesions while circumventing Raman's limited depth of penetration and avoiding systemic toxicity. In this study we evaluated the natural biodistribution of gold surface enhanced Raman scattering (SERS) nanoparticles by radiolabeling them with $^{64}$Cu and imaging their localization over time using microPET. Mice were injected either intravenously (IV) or intrarectally (IR) with approximately 100 μCi (3.7 MBq) of $^{64}$Cu-SERS nanoparticles and imaged with microPET at various time points post injection. Quantitative biodistribution % injected dose per gram (% ID/g) data obtained from each organ correlated well with the corresponding micro-PET images, revealing that mice injected IV had significantly higher uptake ($p<0.05$) in the liver (5 h=8.96% ID/g; 24 h=8.27% ID/g), as opposed to mice injected IR (5 h=0.09% ID/g; 24 h=0.08% ID/g). Mice injected IR showed localized uptake in the large intestine (5 h=10.37% ID/g; 24 h=0.42% ID/g) with minimal uptake in other organs. Raman imaging of excised tissues correlated well with biodistribution data. These results suggest that topical application of SERS nanoparticles in the mouse colon appears to minimize their systemic distribution, thus avoiding potential toxicity and supporting the clinical translation of Raman spectroscopy as an endoscopic imaging tool.

Introduction

Since its discovery, Raman spectroscopy has proven to be a powerful analytical tool offering many advantages including excellent sensitivity to small structural and chemical changes, its ability to multiplex, and its resistance to both autofluorescence and photobleaching. More recently, biomedical researchers have harnessed these unique properties associated with Raman spectroscopy for analysis of cell populations, excised tissue samples, intact preclinical animal models, and even clinical diagnosis.

The principle by which this novel diagnostic approach operates is based on the Raman effect. When light is scattered from a molecule most photons are elastically scattered. However, a small fraction of light is inelastically scattered at optical frequencies different from and usually lower than the frequency of the incident photons. The process leading to this inelastic scatter is termed the Raman effect. However, this effect is very weak, only producing one inelastically scattered photon for every 10 million elastically scattered photons.[1]

Thus far, several researchers have been able to utilize the intrinsic Raman scattering signatures of tissue samples both ex vivo and in vivo to differentiate malignant from normal tissues.[2-5] Due to the low depth of penetration associated with most optical techniques, a Raman endoscope consisting of a flexible optical fiber bundle is often utilized for acquiring these intrinsic Raman spectra from inside the body. Although, this technique has shown to be clinically useful, the weak effect associated with intrinsic Raman scattering remains a problem leading to long exposure times, poor signal, and as a result suboptimal sensitivity.

We intend to overcome this limitation by utilizing surface enhanced Raman scattering (SERS) nanoparticles as tumor targeting contrast agents. SERS is a plasmonic effect where small molecules adsorbed onto a nano-roughened noble metal surface (e.g., gold) experience a dramatic increase in the incident electromagnetic field resulting in several orders of magnitude higher Raman effect, which has recently given us the capability to detect pM concentrations of SERS Raman active nanoparticles when injected in living mice.[6]

Several different kinds of SERS nanoparticles have been recently developed for various in vitro applications including evaluation of cell-cell interactions, tracking and imaging of apoptosis, immunoassay platforms, and even anti-counterfeiting measures.[7-9] However, only a select few have been utilized as tumor targeting beacons in living animal models.[6, 10, 11] Based on the results and experiences gained from our previous studies, we have decided to evaluate the biodistribution properties of the Nanoplex Biotags manufactured by Oxonica. These SERS nanoparticles have ideal properties for clinical translation, including an inert gold composition, excellent Raman signal strength for ultrasensitive detection and multiplexing characteristics with up to 10 unique spectral fingerprints.

Briefly, our clinical diagnostic strategy would involve chemically modifying these SERS nanoparticles with tumor targeting ligands and then topically administering them to the area of interest (i.e. colon) during endoscopic, laparoscopic or surgical procedures, in the hope of avoiding adverse toxicity effects (that may arise from systemic exposure) and also increasing targeting efficiency. After enough time has passed for sufficient binding to occur and rinsing of the unbound nanoparticles has been completed, a Raman endoscope will be used to acquire spectra from the area of interest within the body in order to determine effective tumor targeting.

We intend to use colon cancer to demonstrate this general approach as the first target for reasons of tumor targeted peptide availability, reduced toxicity and a need for improved detection. It was recently reported that flat lesions in the colon were five times more likely to contain cancerous tissue than polyps detected by conventional colonoscopy.[12] In addition, we believe that by administering these gold nanoparticles directly into the bowel we will be able to avoid the systemic system and thus any adverse toxicity effects.

Before proceeding with tumor targeting studies, however, it is first important to fully characterize the localization and accumulation of these SERS Raman nanoparticles in small living subjects. In this study, we have radiolabeled our SERS nanoparticles with $^{64}$Cu in order to assess their natural biodistribution using both microPET imaging and gamma counting followed by Raman imaging and TEM of removed tissues for confirmation of their localization. Two routes of administration were evaluated to compare the differences in distribution between systemic administration and topical application, either intravenous (IV) or intrarectal (IR) injections were given. After IV injection, we would be able to follow the natural distribution of these SERS nanoparticles once they have been introduced into the blood stream. IR administration, on the other hand, would give us a better idea of what happens to these nanoparticles once they have been topically applied, in this case to the colon.

Results

SERS Raman Nanoparticles

All experiments described herein were conducted using SERS nanotags (Oxonica Materials Inc., Mountain View, Calif.).[13, 14] The SERS nanoparticles we used to evaluate biodistribution in this study consisted of a unique Raman active molecular layer, Trans-1,2-Bis(4-pyridyl)-ethylene, adsorbed onto a 60-nm diameter Au core coated with silica, making the entire diameter of the nanoparticle on the order of 120 nm (FIG. 4.5, Supporting Information).[15] The Au nanoparticle core acts as a substrate for SERS and can increase the effective Raman scattering efficiency by several orders of magnitude[16], allowing for more sensitive detection and making it ideal for early detection diagnostic imaging. Upon excitation with a 785-nm laser, the SERS nanoparticles display a unique spectrum based on the inelastic Raman scattering of the incident laser light that comes from interacting with the molecular structure of the adsorbed Raman active layer Trans-1,2-Bis(4-pyridyl)-ethylene.[15] Like most optical techniques, this strategy is depth limited, which is why we intend to eventually utilize a fiber optic based endoscopic approach to overcome this depth issue while still taking full advantage of Raman's ultrasensitive properties and multiplexing characteristics. However, before we can implement this unique strategy for patient studies, we must first thoroughly understand the distribution and localization of our SERS nanoparticles after being administered in the body, preferably by using an imaging modality such as PET that is invulnerable to depth. In order to fully assess the biodistribution properties of these SERS nanoparticles both longitudinally and non-invasively, we conjugated a relatively long-lived (half life=12 h) positron emitting radioisotope, $^{64}$Cu, to their surface (FIG. 4.6, Supporting Information, see Experimental Section for more details), enabling us to monitor/localize them using microPET.

MicroPET Imaging

A series of dynamic microPET images were acquired over the first 13 minutes post IV injection (see SI Video), and revealed immediate uptake of SERS nanoparticles within the liver and spleen, the two major organs that comprise the reticuloendothelial system (RES) and are responsible for breaking down nanoparticles on the order of 120 nm. Rapid accumulation of SERS nanoparticles was observed within the first two minutes post IV injection in both the liver and spleen followed by continuous localization for the remainder of the 13 minute dynamic imaging series (FIG. 4.7, Supporting Information). Although the majority of accumulation was seen in the liver and spleen, the lungs also showed minimal accumulation of SERS nanoparticles with a maximum uptake at approximately 15 seconds post injection, most likely due to the first pass of the SERS nanoparticles encountering the lungs after being administered as a bolus IV.

Static microPET images acquired at various time points post injection over 24 hours revealed clear differences in the distribution patterns of SERS nanoparticles injected IV versus IR (FIG. 4.1). Mice injected IV showed immediate accumulation of $^{64}$Cu-SERS nanoparticles in the liver and spleen after IV injection with continuous localization in the liver and spleen over 24 hours (spleen not visible in coronal slices shown in FIG. 4.1). In contrast, the mice receiving an IR injection, displayed an initial uptake of $^{64}$Cu-SERS nanoparticles localized in the colon, followed by a rapid decrease in uptake over the 24 hour period (see FIG. 4.8, Supporting Information), where the majority of the SERS nanoparticles appear to have cleared the colon and thus the body, likely via fecal excretion.

Biodistribution Data

Tissues were harvested from mice for gamma counting at necropsy 2, 5, and 24 h either post IV or IR injection to quantitatively assess the biodistribution of SERS nanoparticles within various organs and to correlate their localization with their respective microPET images. Quantitative biodistribution (% ID/g) data obtained from each organ correlated well with the corresponding microPET images, and revealed significant uptake of SERS nanoparticles in several organs of mice injected IV as opposed to those injected IR as seen in FIG. 4.2. For instance, mice injected IV had significantly higher uptake (p<0.05) in the liver (2 h=11.35% ID/g; 5 h=8.96% ID/g; 24 h=8.27% ID/g), as opposed to mice injected IR (2 h=0.55% ID/g; 5 h=0.09% ID/g; 24 h=0.08% ID/g). This significant increase in SERS nanoparticle uptake in mice receiving IV injections as opposed to IR injections was also seen in several other organs including the spleen, kidneys, stomach, and lungs.

Mice injected IR, however, showed localized SERS nanoparticle uptake in the large intestine (2 h=123.72% ID/g) (5 h=10.37% ID/g) (24 h=0.42% ID/g) with minimal uptake (less than 0.13% ID/g) in every other organ at 24 h. Quantitative microPET analysis also reveals that this minimal uptake seen in other organs (i.e. liver) after IR injection correlates well with free $^{64}$Cu as seen over the 24 hour period thus suggesting the activity is likely due to the dissociation of the $^{64}$Cu from the SERS nanoparticles (FIG. 4.9, Supporting Information). SERS nanoparticle uptake was also observed in the cecum at 2 and 5 h post IR injection. This was likely due to the slight size variability between mice and the volume of SERS nanoparticles that was estimated to fill the entire colon, therefore during IR injection slight overflow from the large intestine into the cecum may have occurred.

Overall, SERS nanoparticles appear to be retained in several organs, even at 24 hours post IV injection, whereas mice receiving "topical" IR injections showed localized accumulation initially in the cecum/colon with minimal retention at 24 hours and no signs of SERS nanoparticle accumulation in any other organs throughout the entire study.

Serum Stability of SERS Nanoparticles and Raman Imaging of Excised Tissues

Serum stability studies on the SERS nanoparticles revealed consistent Raman signal associated with the active molecular layer, Trans-1,2-Bis(4-pyridyl)-ethylene on the SERS nanoparticle over 24 hour incubation. The spectral fingerprint was found to be unaffected and no differences in signal intensity were observed as compared to SERS nanoparticles incubated with distilled water or PBS (more details provided in SI Text). Raman maps were acquired of various excised tissues, particularly those mentioned above displaying an increased $^{64}$Cu uptake, to confirm the presence of SERS nanoparticles injected. Raman imaging revealed the exact spectral fingerprint associated with the SERS nanoparticles administered IV within the liver, spleen, lungs, and kidneys across all time points (FIG. 4.3). However, mice injected IR only displayed enough SERS nanoparticle accumulation in the colon to produce an adequate Raman signal at 2 and 5 hours post injection with no other detectable accumulation in the liver, spleen, lungs or kidneys over the entire 24 hours.

Histopathology Via Transmission Electron Microscopy (TEM) Imaging of SERS Accumulation Another group of mice were evaluated separately where mice were injected either IV or IR using the same administration technique implemented above. The mice were sacrificed at 5 min and 2 weeks post injection in order to microscopically assess the presence or absence of these SERS nanoparticles within the liver, the main organ responsible for the trapping and degradation of these size nanoparticles. TEM of fixed liver tissues revealed several clusters of our gold SERS nanoparticles within the liver at both 5 min and 2 weeks post IV injection, whereas mice that were administered IR injections revealed no trace of gold SERS nanoparticles at either 5 min or 2 weeks post injection (FIG. 4.4). Of the hundreds of cell sections within the 81000 μm$^2$ area examined for each tissue, not a single SERS nanoparticle was found in the liver after IR injection.

Discussion

SERS nanoparticles possess extraordinary spectral properties, including their ability to be sensitively detected and multiplexed, making them ideal to be utilized as tumor targeting molecular imaging agents. Several novel nanoparticle constructs with great potential for either diagnostic or therapeutic applications are currently being investigated.[17-20] However, two major obstacles have kept most of them from being clinically translated 1) effective delivery to tumor site 2) toxicity issues. Since most nanomedicines, to date, are administered systemically, several factors (e.g., size, surface charge, hydrophobicity) need to be considered during their development in order to help overcome these obstacles. Size, for instance, plays an important role in determining where these nanoparticles will accumulate in the body over time and how they will be broken down and eventually cleared (via liver/spleen or kidney). Nanoparticle size has also shown to significantly influence both circulation half life and their ability to extravasate into the tumor space, both of which determine tumor targeting efficiency. Although most nanocarriers rely on the enhanced permeability and retention (EPR) effect to extravasate through leaky tumor vasculature and selectively accumulate in the tumor tissue, it has recently been reported that not all tumors display the same degree of "leakiness"[21], making it even more difficult to effectively deliver these nanoparticles out of the vasculature to their targets within a tumor. With this in mind, we have devised a way to circumvent these obstacles of delivery and toxicity by topically administering our nanoparticles to an area of interest (i.e. colon). That way the nanoparticles won't have to extravasate out of the vasculature in order to find their target, since they will be directly applied to the area of interest (i.e. colon) and adverse systemic toxicity affects could potentially be avoided as well by avoiding IV administration.

In this study, we have evaluated the biodistribution of our SERS nanoparticles (~120 nm) after both IV and IR administration. The SERS nanoparticles were radio-labeled with $^{64}$Cu using a DOTA chelator (FIG. 4.6, Supporting Information). These studies were performed under the assumption that the DOTA-SERS nanoparticles behave identically to SERS nanoparticles alone, in terms of biodistribution, and that the DOTA, being a small entity, does not contribute significantly to the natural biodistribution of the nanoparticle as previously described by Schipper et al.[22] In addition, our results show a different biodistribution pattern than that of free $^{64}$Cu (mostly accumulating in the kidney and bladder due to its natural route of excretion) suggesting minimal dissociation of the $^{64}$Cu from the SERS nanoparticles. Furthermore, the minimal % ID/g uptake seen in other organs (FIG. 4.2) besides the cecum/large intestine after IR administration is most likely due to the dissociation of $^{64}$Cu from the SERS nanoparticles. The distribution patterns of free $^{64}$Cu behave similarly to $^{64}$Cu-labled SERS nanoparticles in other organs outside the large intestine (i.e. liver) (FIG. 4.9, Supporting Information) suggesting that the uptake represents the free dissociated $^{64}$Cu and not the accumulation of the actual SERS nanoparticles themselves.

After thorough microPET and tissue uptake analysis, the results clearly show a difference in nanoparticle distribution after administration between the IV and IR groups, where mice receiving a "topical" IR administration showed localized accumulation of our SERS nanoparticles within the colon and its neighboring organ, the cecum. No absorption of the SERS nanoparticles was observed within any other organ over the 24 hour microPET imaging sequence, and the liver was clear of SERS nanoparticles out to two weeks post IR administration via TEM imaging. Additionally, the SERS nanoparticles cleared the colon relatively quickly (FIG. 4.8, Supporting Information) where less than 1% ID/g was left in the large intestine after 24 hours post IR injection. Mice injected IV, on the other hand, revealed immediate accumulation of our SERS nanoparticles, in the lungs, liver and spleen, with continued uptake in both the liver and spleen over the entire 24 hour microPET imaging sequence. TEM imaging also confirmed the presence of our SERS nanoparticles within the liver at both early and late stage time points post IV injection (FIG. 4.4). These results support the use of these SERS nanoparticles as a topically applied contrast agent within the colon for the potential earlier detection of colon cancer.

Thus far, the use of Raman nanoparticles as imaging contrast agents for clinical utility has never been demonstrated before, predominantly due to the weak signal generally associated with Raman spectroscopy and the limited depth of penetration that comes from using an optical technique. With this in mind, we propose to exploit the SERS effect, a metal based phenomenon that utilizes surface plasmon resonance, to significantly enhance the Raman signal coming from our contrast agent (i.e. SERS nanoparticles). In addition, we will employ an endoscopic imaging device, modified for acquiring Raman spectra within the colon, to localize the accumulation of our tumor targeting SERS nanoparticles in order to overcome the limited depth of penetration issue.

Other localized routes of administration have recently been investigated including the fate of various sized gold nanoparticles after either intratracheal instillation or inhalation into the lungs.[23, 24] Their finding suggest no detectable amounts of gold on the order of 40 and 100 nm in diameter get translocated from the lungs to the systemic circulation in mice, and that only trace amounts of gold nanoparticles on the order of 2 nm are found in the blood when instilled directly into the trachea.[23] However a larger degree of nanoparticles, on the order of 20 nm, get translocated into the blood stream when inhaled by rats.[24] These studies show promise for our Raman nanoparticles (~120 nm) to be directly instilled into the lung for tumor targeting and detection during bronchoscopy without causing adverse systemic toxicity effects.

The issue of nanoparticle induced toxicity has generated quite a bit of interest amongst the biomedical community, especially now with the approval of several nanoparticle constructs for clinical use.[25] Several reports have recently been published discussing the toxicity effects of various nanoparticles after being administered intravenously[18, 25-30], all with similar concerns as to exactly how long these nanoparticles seem to stay in the body (i.e. liver, spleen and kidneys), with some reports claiming up to several months post IV injection.[27, 31-33] A huge advantage to administering these nanoparticles topically is their ability to be cleared without crossing into the systemic circulation and thus avoiding the issue of prolonged retention in vital organs like the liver, spleen and kidneys.

Another major advantage to utilizing SERS nanoparticles as tumor targeting contrast agents is their unique ability to multiplex. We currently have 10 different batches of SERS nanoparticles, each displaying a unique spectral fingerprint when imaged, thus giving us the capability to interrogate several different targets simultaneously.[15] Several colon cancer biomarkers have recently been identified along with their associated tumor targeting ligands.[34, 35] If one were to conjugate each batch of SERS nanoparticles with different colon cancer targeting ligands this multiplexing technique could enable us to evaluate the targeting efficiency of several tumor targeting SERS nanoparticles simultaneously, thus offering us increased specificity as to which biomarker is overexpressed on different regions of the diseased colon. No other imaging modality has the capability of offering this kind of multiplexed information to the degree of being able to spectrally unmix and identify 10 unique individually dispersed nanoparticles.

Although we intend to initially interrogate colon cancer to demonstrate this novel approach, for reasons of tumor targeted ligand availability, reduced toxicity, and the need for improved detection, this technique is in no way limited to diseases of the colon. In fact, several tissues could be interrogated for cancer detection utilizing this procedure including skin, bladder, lungs, esophagus, cervix and vagina; all of which are easily accessible and can be imaged with a Raman endoscopic device.

Conclusions

In conclusion, this novel endoscopic approach which utilizes the ultrasensitive detection and multiplexing properties of Raman spectroscopy in conjunction with SERS nanoparticles has great potential for clinical utility, not only for colon assessment but also for other endoscopic applications (i.e., esophagus, cervix, and bladder). Although more thorough toxicity testing needs to be performed on these SERS nanoparticles, and is currently ongoing in our lab, these initial biodistribution results hold significant promise in translating this novel technique to the clinic, with the hope of improving early cancer detection and thus the prognosis for cancer patients.

Experimental Section

SERS Nanoparticles.

SERS nanotags were provided by Oxonica Materials Inc. (Mountain View, Calif.) and comprised a 60-nm diameter Au core coated with a monolayer of Raman-active organic molecule, Trans-1,2-Bis(4-pyridyl)-ethylene, and encapsulated with a 30-nm diameter silica shell, making the entire particle on the order of ~120 nm. The particular lot used in this study was the S440 batch which consists of a unique Raman active material and its associated spectrum which can be seen in our previous work.[15] Reproducibility of these SERS nanoparticles was previously evaluated in our lab which revealed a 1.9% coefficient of variance among multiple sample measurements.[6]

Chemical Conjugation and Radio-labeling of SERS Nanoparticles.

Preparation of Pegylated SERS Nanoparticles.

To stabilize the gold nanospheres against aggregation under various conditions both long and short chain polyethylene glycol (PEG) molecules were conjugated to the nanosphere's silica surface (in a molar ratio of 1:5, long:short). Specifically: a solution of Maleimide-$PEG_{5000}$-N-hydroxysuccinimide ester (Mal-$PEG_{5000}$-NHS, 2 mg, 0.4 µM) and Maleimide-$PEG_{2000}$-methoxy (Mal-$PEG_{2000}$-OCH3, 4 mg, 2 µM) in 2-morpholinoethanesulfonic acid (MES) buffer (pH=7.2) was added to thiolated SERS particles (0.5 mL, 0.02 nM) and stirred at room temperature for 1 hour. Excess PEG molecules were separated from pegylated nanoparticles by three rounds of centrifugation (10,000 RPM, 4 min), and resuspension in MES buffer (pH=7.2). Conjugation with DOTA.

Pegylated gold nanospheres were functionalized with DOTA to enable chelation of radioactive metal ions (in this case Copper-64, half life=12.7 h). Specifically: primary amine-DOTA was covalently conjugated to NHS ester terminated long chain PEG molecules on gold nanoparticles via the addition of p-$NH_2$-Bn-DOTA (0.9 mg, 1.3 µmol in 0.5 mL MES buffer (pH=7.2) to pelleted pegylated particles. Solution was stirred at room temperature overnight. Excess DOTA was separated from functionalized nanoparticles by three rounds of centrifugation (10,000 RPM, 4 min), and resuspension in MES buffer (pH=7.2). DOTA-functionalized nanoparticles were finally suspended in deionized water (0.5 mL) for radiolabeling.

Protocol of SERS Copper-64 Labeling.

The SERS nanoparticles were radiolabeled with $^{64}$Cu by addition of 185-259 MBq (5~7 mCi)$^{64}$CuCl$_2$ [1 pmol SERS nanoparticles per 1.62 GBq $^{64}$Cu] in 0.01 N NaOAc (pH 5.0) buffer followed by a 1 h incubation at 37° C. with gentle shaking. SERS nanoparticles were centrifuged and washed with deionized sterile water three times to remove non-chelated copper. Labeling yield is ~20-30% therefore the resulting specific activity was 324-486 MBq per 1 pmol SERS nanoparticles (8.76-13.14 mCi/pmol). Rinsed SERS nanoparticle were resuspended in 400 μl of PBS by sonicating and vortexing. According to N-succinimidyl-3-(2-pyridyldithio)propionate (SPDP) spectrographic analysis[36] of our $^{64}$Cu-tagged SERS nanoparticles this method attaches ~60,000 $^{64}$Cu molecules per nanoparticle (~1 $^{64}$Cu molecule per 3 nm$^2$ surface area).

Animal Experiments.

Female 8 week old nude mice (Charles River) were used for all biodistribution studies. All procedures performed on the animals were approved by the University's Institutional Animal Care and Use Committee, and were within the guidelines of humane care of laboratory animals.

Animal Injections.

Mice were divided into two injection groups to evaluate differences in biodistribution between administering SERS nanoparticles intravenously (IV) versus intrarectally (IR). Each group contained subgroups where mice were further separated to evaluate biodistribution at various time points post injection. Three mice from each group were sacrificed at 2 hr, 5 hr and 24 hr to evaluate accumulation of SERS nanoparticles within specific organs of interest. Mice in the IV group were given a 200 μl injection of approximately 100 μCi of $^{64}$Cu-SERS nanoparticles via the tail vein using a 26 gauge needle. Mice in the IR group also received a 200 μl injection of approximately 100 μCi of $^{64}$Cu-SERS nanoparticles using the hollow flexible portion of a 25 gauge angiocatheter inserted via the rectum.

MicroPET Imaging.

On the day of imaging, each mouse was anesthetized with 2.5-3% isoflurane delivered by 100% oxygen as the carrier gas at 2 liters per minute through an isoflurane vaporizer. MicroPET imaging commenced immediately after injection of the $^{64}$Cu-SERS nanoparticles. The mice were placed prone on the microPET bed and imaged with a Rodent R4 MicroPET system manufactured by CTI Concorde Microsystems (Knoxville, Tenn.). Five minute static images were acquired at various time points post injection: Immediately, 30 min, 2 h, 5 h, and 24 h. The images were then reconstructed using a two dimensional ordered subset expectation maximization (2D-OSEM) algorithm with a spatial resolution of 1.66 to 1.85 mm[37] and analyzed using both Amide [38] and AsiPRO image processing software. No attenuation correction or partial volume correction were applied.

Biodistribution.

After imaging, mice were then euthanized by cervical dislocation under deep isoflurane anesthesia. In each injection group (IV and IR) mice were sacrificed at 2 h (n=3), 5 h (n=3), and 24 h (n=3). Tissues were harvested, weighed and placed in scintillation vials for gamma counting. Organs of interest such as the liver spleen and colon were placed in vials containing a 2:1:1 solution of 0.2M sodium cacodylate buffer: 10% glutaraldehyde: 8% paraformaldehyde (EMSdiasum) for transmission electron microscopy (TEM) analysis. All tissues harvested were counted for 1 min in a Cobra II γ-counter (Packard/Perkin Elmer). Results in FIG. 4.2 are expressed as % injected dose per gram tissue (% ID/g).

TEM Analysis.

Organs of interest such as the liver spleen and colon were fixed and prepared for TEM analysis in order to verify the microscopic location of the SERS nanoparticles after either IV or IR administration. Ten grid spacings corresponding to a 81000 μm$^2$ area were examined. Each section was 150 nm thick corresponding to a total of 12500 μm$^3$ of material examined for each tissue sample. More details on the methods of sample preparation are provided in SI Text.

Raman Spectroscopic Imaging in Excised Tissues.

Raman measurements on excised tissues were performed with a Renishaw microscope system to verify the presence of SERS nanoparticles within specific organs of interest. A semiconductor diode near-infrared laser operating at λ=785 nm was used as the excitation source with a laser power of 60 mW measured at the surface of the tissues. Raman images were obtained by using a Raman point mapping method. A computer-controlled x-y translation stage was used to rasterscan the tissues creating a spectral image by measuring the Raman spectrum of each individual pixel in the area of interest with a 750 μm or 1 mm step size. Integration times of 3 seconds per step were acquired for each tissue Raman map. The objective lens used was a 12× open field in a dimly lit room.

Spectral Analysis.

The direct classical least squares (DCLS) method, also called linear un-mixing and K-matrix methods, was used in this work to perform analysis of Raman spectroscopy.[39, 40] For more details see SI Text.

Statistical Analysis.

The data collected from these experiments were analyzed for statistical differences using a 95% confidence interval (p<0.05). More details provided in below Supplemental information to Example 4

SI Text

Serum Stability

SERS nanoparticles were incubated with 100% mouse serum over a period of 24 hours at 37° C. After incubation, SERS nanoparticles were taken for Raman analysis to determine stability of the Raman signal associated with the active molecular layer, Trans-1,2-Bis(4-pyridyl)-ethylene on the SERS nanoparticle. The spectral fingerprint was found to be stable over the 24 hour incubation period with mouse serum and showed no differences in signal intensity or spectral signature as compared to SERS nanoparticles incubated with distilled water or PBS.

TEM Analysis

Samples collected in the fixing solution mentioned above for TEM analysis were stored at 4° C. before being stained en bloc in 1% osmium tetroxide in water at 4° C. for 2 hours. Samples were rinsed twice in cold deionized water and then stained in 1% uranyl acetate in water at 4° C. overnight. Samples were then dehydrated in increasing concentrations of ethanol at 4° C.; 50, 75, and 95%. After dehydration in 95% ethanol, samples were warmed to room temperature for further processing. Samples were dehydrated twice in 100% ethanol followed by further dehydration three times in propylene oxide. Samples were suspended in a 1:1 solution of Embed 812 epoxy resin (EMSdiasum): propylene oxide for 1 hour, followed by a suspension in a 2:1 solution of Embed 812 epoxy resin: propylene oxide overnight. Sample were resuspended in Embed 812 epoxy resin for 1 hour before being placed in flat embedding molds and cured at 60° C. overnight. The cured epoxy blocks were removed from the mold and trimmed with a razor to reveal the tissue sample embedded within. Thin (150 nm) sections of each organ were cut using a Leica Ultracut S microtome and placed on a 200 mesh bare copper grid. These sections were examined using a Tecnai F20 (FEI company) transmission electron microscope operating at 120 kV. Scanning transmission electron microscopy (STEM) was utilized to analyze each sample in order to determine the microscopic location of the SERS nanoparticles. 10 grid spacings corresponding to a 81000 μm$^2$ area were examined. Each section was 150 nm thick corresponding to a total of 12500 μm$^3$ of material examined for each tissue sample.

Spectral Analysis

DCLS finds the linear combination of spectra from the pure components contained in the sample that most closely matches the Raman spectrum of the sample. A pure component spectrum of the SERS nanoparticles used in this study was acquired from a pure 3 µl sample aliquoted onto a piece of quartz under the microscope and used as the reference spectrum for the Raman analysis of the tissues.

Statistical Analysis

A student's t-test was used to compare the data of the IV group to the data of the IR group. An equality of variances test was performed and revealed little variance between the groups. Therefore, a one-tailed t-test assuming equal variances was performed to determine statistical significance because it was hypothesized that the IR group would have localized uptake in the large intestine and perhaps some leakage into the cecum with little to no uptake in any other organ, where as the IV group would have higher uptake in all organs subjected to systemic delivery. The values reported appear as mean±standard error of mean (SEM). A Bonferroni correction was not performed because it was too conservative since the data from each of the time points correlated well with each other, and there was little chance of getting a significant result from multiple t-testing.

References for Example 4, Each of Which is Incorporated Herein by Reference

[1] D. C. Harris; M. D. Bertolucci, *Symmetry and Spectroscopy: An Introduction to Vibrational and Electronic Spectroscopy* Dover Publications: Mineola, N.Y., 1989; p 550.

[2] A. S. Haka; K. E. Shafer-Peltier; M. Fitzmaurice; J. Crowe; R. R. Dasari; M. S. Feld, *PNAS* 2005, 102, 12371-6.

[3] E. M. Kanter; E. Vargis; S. Majumder; M. D. Keller; E. Woeste; G. G. Rao; A. Mahadevan-Jansen, *J Biophotonics* 2009, 2, 81-90.

[4] K. Maheedhar; R. A. Bhat; R. Malini; N. B. Prathima; P. Keerthi; P. Kushtagi; C. M. Krishna, *Photomed Laser Surg* 2008, 26, 83-90.

[5] J. T. Motz; S. J. Gandhi; O. R. Scepanovic; A. S. Haka; J. R. Kramer; R. R. Dasari; M. S. Feld, *J Biomed Opt* 2005, 10, 031113.

[6] S. Keren; C. Zavaleta; Z. Cheng; A. de la Zerda; O. Gheysens; S. S. Gambhir, *Proc Natl Acad Sci USA* 2008, 105, 5844-9.

[7] C. M. Shachaf; S. V. Elchuri; A. L. Koh; J. Zhu; L. N. Nguyen; D. J. Mitchell; J. Zhang; K. B. Swartz; L. Sun; S. Chan; R. Sinclair; G. P. Nolan, *PLoS One* 2009, 4, e5206.

[8] C. Song; Z. Wang; R. Zhang; J. Yang; X. Tan; Y. Cui, *Biosens Bioelectron* 2009, 25, 826-31.

[9] K. N. Yu; S. M. Lee; J. Y. Han; H. Park; M. A. Woo; M. S. Noh; S. K. Hwang; J. T. Kwon; H. Jin; Y. K. Kim; P. J. Hergenrother; D. H. Jeong; Y. S. Lee; M. H. Cho, *Bioconjug Chem* 2007, 18, 1155-62.

[10] X. Qian; X. H. Peng; D. O. Ansari; Q. Yin-Goen; G. Z. Chen; D. M. Shin; L. Yang; A. N. Young; M. D. Wang; S. Nie, *Nat Biotechnol* 2008, 26, 83-90.

[11] C. Zavaleta; A. de la Zerda; Z. Liu; S. Keren; Z. Cheng; M. Schipper; X. Chen; H. Dai; S. S. Gambhir, *Nano Lett* 2008, 8, 2800-5.

[12] R. M. Soetikno; T. Kaltenbach; R. V. Rouse; W. Park; A. Maheshwari; T. Sato; S. Matsui; S. Friedland, *Jama* 2008, 299, 1027-35.

[13] W. E. Doering; M. E. Piotti; M. J. Natan; R. G. Freeman, *Adv Materials* 2007, 19, 3100-3108.

[14] M. Y. Sha; H. Xu; M. J. Natan; R. Cromer, *J Am Chem Soc* 2008, 130, 17214-5.

[15] C. L. Zavaleta; B. R. Smith; I. Walton; W. Doering; G. Davis; B. Shojaei; M. J. Natan; S. S. Gambhir, *Proc Natl Acad Sci USA* 2009, 106, 13511-6.

[16] M. Fleischmann; P. J. Hendra; A. J. McQuillan, *Chem Phys Lett* 1974, 26, 163-166.

[17] P. Debbage; W. Jaschke, *Histochem Cell Biol* 2008, 130, 845-75.

[18] S. E. McNeil, *Wiley Interdiscip Rev Nanomed Nanobiotechnol* 2009, 1, 264-71.

[19] I. L. Medintz; H. Mattoussi; A. R. Clapp, *Int J Nanomedicine* 2008, 3, 151-67.

[20] A. C. Powell; G. F. Paciotti; S. K. Libutti, *Methods Mol Biol* 624, 375-84.

[21] B. R. Smith; Z. Cheng; A. De; J. Rosenberg; S. S. Gambhir, *Small*.

[22] M. L. Schipper; Z. Cheng; S. W. Lee; L. A. Bentolila; G. Iyer; J. Rao; X. Chen; A. M. Wu; S. Weiss; S. S. Gambhir, *J Nucl Med* 2007, 48, 1511-1518.

[23] E. Sadauskas; N. R. Jacobsen; G. Danscher; M. Stoltenberg; U. Vogel; A. Larsen; W. Kreyling; H. Wallin, *Chem Cent J* 2009, 3, 16.

[24] L. E. Yu; Y. L.L.; C. N. Ong; Y. Tan; K. S. Balasubramaniam; D. Hartono; G. Shui; M. R. Wenk; W. Y. Ong, *Nanotoxicology* 2007, 1, 235-242.

[25] P. P. Adiseshaiah; J. B. Hall; S. E. McNeil, *Wiley Interdiscip Rev Nanomed Nanobiotechnol* 2, 99-112.

[26] M. A. Dobrovolskaia; S. E. McNeil, *Nat Nanotechnol* 2007, 2, 469-78.

[27] M. L. Schipper; N. Nakayama-Ratchford; C. R. Davis; N. W. Kam; P. Chu; Z. Liu; X. Sun; H. Dai; S. S. Gambhir, *Nat Nanotechnol* 2008, 3, 216-21.

[28] S. T. Stern; S. E. McNeil, *Toxicol Sci* 2008, 101, 4-21.

[29] G. Xie; J. Sun; G. Zhong; L. Shi; D. Zhang, *Arch Toxicol* 2009.

[30] K. T. Yong; I. Roy; H. Ding; E. J. Bergey; P. N. Prasad, *Small* 2009, 5, 1997-2004.

[31] S. K. Balasubramanian; J. Jittiwat; J. Manikandan; C. N. Ong; L. E. Yu; W. Y. Ong, *Biomaterials* 31, 2034-42.

[32] R. Goel; N. Shah; R. Visaria; G. F. Paciotti; J. C. Bischof, *Nanomedicine (Lond)* 2009, 4, 401-10.

[33] P. Lin; J. W. Chen; L. W. Chang; J. P. Wu; L. Redding; H. Chang; T. K. Yeh; C. S. Yang; M. H. Tsai; H. J. Wang; Y. C. Kuo; R. S. Yang, *Environ Sci Technol* 2008, 42, 6264-70.

[34] A. Cappellani; M. Di Vita; A. Zanghi; P. Veroux; A. Cavallaro; E. Lo Menzo; B. Cacopardo; V. Canzonieri; P. Murabito; U. Tirelli; M. Berretta, *Front Biosci (Schol Ed)* 2, 422-31.

[35] P. L. Hsiung; J. Hardy; S. Friedland; R. Soetikno; C. B. Du; A. P. Wu; P. Sahbaie; J. M. Crawford; A. W. Lowe; C. H. Contag; T. D. Wang, *Nat Med* 2008, 14, 454-8.

[36] T. T. Ngo, *J Biochem Biophys Methods* 1986, 12, 349-54.

[37] C. Knoess; S. Siegel; A. Smith; D. Newport; N. Richerzhagen; A. Winkeler; A. Jacobs; R. N. Goble; R. Graf; K. Wienhard; W. D. Heiss, *Eur J Nucl Med Mol Imaging* 2003, 30, 737-47.

[38] A. M. Loening; S. S. Gambhir, *Mol Imaging* 2003, 2, 131-7.

[39] D. M. Haaland; R. G. Easterling, *Appl Spec* 1980, 34, 539-548.

[40] M. J. Pelletier, *Appl Spect* 2003, 57, 20A-42A.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. In an embodiment, the term "about" can include traditional rounding according to significant figures of the numerical value. In addition, the phrase "about 'x' to 'y'" includes "about 'x' to about 'y'".

It should be emphasized that the above-described embodiments of the present disclosure are merely possible examples of implementations, and are set forth only for a clear understanding of the principles of the disclosure. Many variations and modifications may be made to the above-described embodiments of the disclosure without departing substantially from the spirit and principles of the disclosure. All such modifications and variations are intended to be included herein within the scope of this disclosure.

We claim:

1. A method of imaging, comprising:
   administering at least two types of Raman agents to a subject, wherein at least one of the two types of Raman agents has a specific affinity for a specific target;
   introducing a Raman imaging device into the subject;
   positioning the Raman imaging device adjacent the specific target inside the subject;
   exposing the specific target inside the subject to a light beam from the Raman imaging device, wherein the light beam is scattered by the first type of Raman agent that associated with the specific target, wherein the light beam that is scattered is referred to as a Raman scattered light energy; and
   detecting the Raman scattered light inside the subject using the Raman imaging device, using the Raman scattered light energy to form an image; and
   analyzing the scattered light to determine the type of Raman agent, wherein the type of Raman agent determines the specific target detected,
   wherein one of the at least two types of Raman agent is not target-specific, and wherein the method further comprises analyzing the scattered light to determine the ratio of the specific binding Raman agent to non-specific binding Raman agent, wherein the ratio provides an estimate of the bound Raman agents.

2. The method of claim 1, wherein the Raman agent is selected from the group consisting of: a Raman nanoparticle and a Raman compound.

3. The method of claim 1, wherein the specific target is selected from the group consisting of: cancer, tumor, precancerous cells or tissue, atherosclerosis, and fibrosis.

4. The method of claim 1, wherein introducing the Raman imaging device includes introducing into the subject the Raman imaging device to an anatomical region of the subject, wherein the anatomical region of the subject is selected from the group consisting of: cervix, bladder, bronchioles, esophagus, stomach, colon, and rectum.

5. The method of claim 4, further comprising, mapping of at least a portion of the subject using the Raman scattered light, wherein mapping includes collecting Raman scattered light and correlating the Raman scattered light to a position in at least a portion of the inside of the subject, wherein the portion of the subject is selected from the group consisting of: cervix, bladder, bronchioles, esophagus, stomach, colon, and rectum.

6. The method of claim 1, wherein administering includes administering, locally to the colon, a gold nanoparticle Raman agent having a targeting agent specific for a dysplastic flat lesion in the colon, wherein the specific target is a dysplastic flat lesion, and wherein introducing includes introducing into the colon.

7. The method of claim 1, wherein administering includes administering, locally to the colon, a polyethylene glycol (PEG)-ylated Raman active silica-gold nanoparticle Raman agent having a targeting agent specific for colorectal cancer, wherein the specific target is a colorectal cancer, and wherein introducing includes introducing into the colon.

8. A method of imaging, comprising:
   administering a plurality of types of Raman agents to a subject, wherein at least two types of Raman agents have a specific affinity for a different target;
   positioning inside the subject a Raman imaging device adjacent an area that includes one or more of the different targets;
   exposing the area inside the subject to a light beam from the Raman imaging device, wherein if one or more of the plurality of Raman agents is present, the light beam is scattered, wherein the light beam that is scattered is referred to as a Raman scattered light energy, wherein each different type of Raman agent has a detectably different Raman scattered light energy;
   detecting inside the subject the Raman scattered light using the Raman imaging device; and
   analyzing the scattered light to determine the type of Raman agent, wherein the type of Raman agent determines a target detected,
   wherein at least one of the plurality of Raman agents is not target-specific, and wherein the method further comprises analyzing the scattered light to determine the ratio of the specific binding Raman agent to non-specific binding Raman agent, wherein the ratio provides an estimate of the bound Raman agents.

9. The method of claim 8, wherein each target is selected from the group consisting of: cancer, tumor, precancerous cells or tissue, atherosclerosis, fibrosis, and a combination thereof.

10. The method of claim 8, wherein introducing the Raman imaging device includes introducing inside the subject the Raman imaging device to an anatomical region of the subject, wherein the anatomical region of the subject is selected from the group consisting of: cervix, bladder, bronchioles, esophagus, stomach, colon, and rectum.

11. The method of claim 10, further comprising, mapping of at least a portion of the subject using the Raman scattered light, wherein mapping includes collecting Raman scattered light and correlating the Raman scattered light to a position in at least a portion of the inside of the subject, wherein the portion of the subject is selected from the group consisting of: cervix, bladder, bronchioles, esophagus, stomach, colon, and rectum.

12. A method of imaging, comprising:
- administering at least two types of Raman agents to a subject, wherein at least one of the two types of the Raman agents has a specific affinity for a specific target;
- introducing a Raman imaging device into the subject;
- positioning the Raman imaging device adjacent the specific target inside the subject;
- exposing the specific target inside the subject to a light beam from the Raman imaging device, wherein the light beam is scattered by the first type of Raman agent that associated with the specific target, wherein the light beam that is scattered is referred to as a Raman scattered light energy;
- detecting the Raman scattered light inside the subject using the Raman imaging device, using the Raman scattered light energy to form an image; and
- wherein administering includes administering, locally to the colon, a gold nanoparticle Raman agent having a targeting agent specific for a dysplastic flat lesion in the colon, wherein the specific target is a dysplastic flat lesion, and wherein introducing includes introducing into the colon; and
- analyzing the scattered light to determine the type of Raman agent, wherein the type of Raman agent determines the specific target detected,
- wherein one of the at least two types of Raman agent is not target-specific, and wherein the method further comprises analyzing the scattered light to determine the ratio of the specific binding Raman agent to non-specific binding Raman agent, wherein the ratio provides an estimate of the bound Raman agents.

13. The method of claim 12, wherein administering includes administering, locally to the colon, a polyethylene glycol (PEG)-ylated Raman active silica-gold nanoparticle Raman agent having a targeting agent specific for colorectal cancer, wherein the specific target is a colorectal cancer, and wherein introducing includes introducing into the colon.

14. The method of claim 12, wherein introducing the Raman imaging device includes introducing into the subject the Raman imaging device to an anatomical region of the subject, wherein the anatomical region of the subject is selected from the group consisting of: cervix, bladder, bronchioles, esophagus, stomach, colon, and rectum.

15. The method of claim 14, further comprising, mapping of at least a portion of the subject using the Raman scattered light, wherein mapping includes collecting Raman scattered light and correlating the Raman scattered light to a position in at least a portion of the inside of the subject, wherein the portion of the subject is selected from the group consisting of: cervix, bladder, bronchioles, esophagus, stomach, colon, and rectum.

* * * * *